US007928200B1

(12) United States Patent
Keith et al.

(10) Patent No.: US 7,928,200 B1
(45) Date of Patent: Apr. 19, 2011

(54) HUMAN GENES RELATING TO RESPIRATORY DISEASES AND OBESITY

(75) Inventors: Tim Keith, Bedford, MA (US); Randall Little, Newtonville, MA (US); Paul Van Eerdewegh, Weston, MA (US); Josèe Dupuis, Newton, MA (US); Richard Del Mastro, Norfolk, MA (US); Jason Simon, Westfield, NJ (US); Kristina Allen, Hopkinton, MA (US); Sunil Pandit, Gaithersburg, MD (US)

(73) Assignee: Oscient Pharmaceuticals Corporation, Waltham, MA (US)

( * ) Notice: Subject to any disclaimer, the term of this patent is extended or adjusted under 35 U.S.C. 154(b) by 0 days.

(21) Appl. No.: 12/180,184

(22) Filed: Jul. 25, 2008
(Under 37 CFR 1.47)

Related U.S. Application Data

(62) Division of application No. 10/743,704, filed on Dec. 22, 2003, now Pat. No. 7,407,804, which is a division of application No. 09/627,465, filed on Jul. 28, 2000, now Pat. No. 6,737,519.

(60) Provisional application No. 60/146,336, filed on Jul. 30, 1999, provisional application No. 60/211,749, filed on Jun. 14, 2000.

(51) Int. Cl.
*C07K 16/00* (2006.01)
(52) U.S. Cl. ............... 530/387.1; 530/388.1; 530/391.1; 530/387.3
(58) Field of Classification Search .................. None
See application file for complete search history.

(56) References Cited

U.S. PATENT DOCUMENTS

| 5,011,912 A * | 4/1991 | Hopp et al. ................. 530/387.9 |
| 5,304,640 A | 4/1994 | Laskey et al. |
| 5,731,192 A | 3/1998 | Reeders et al. |
| 5,773,249 A | 6/1998 | Cappello et al. |
| 5,773,577 A | 6/1998 | Cappello |
| 5,830,713 A | 11/1998 | Ferrari et al. |
| 6,150,081 A | 11/2000 | Van Heerde et al. |
| 6,319,716 B1 | 11/2001 | Tikoo et al. |

FOREIGN PATENT DOCUMENTS

| FR | 2 748 479 | 11/1997 |
| WO | WO 85/02610 | 6/1985 |
| WO | WO 95/23611 | 9/1995 |
| WO | WO 98/10063 | 3/1998 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Chothia et al (The EMBO Journal, 1986, 5/4:823-26).*
Greenspan et al (Nature Biotechnology 7: 936-937, 1999.*
Shankar et al (Biochem. J. 300:295-298.1994).*
P. Labhart et al., "DNA sequences for typical ribosomal gene spacers from *Xenopus laevis* and *Xenopus borealis*", 1987, Nucleic Acids Research, vol. 15, 8:3623-3624.
T. Moss et al., "More ribosomal spacer sequences from *Xenopus laevis*", 1980, Nucleic Acid Research, vol. 8, 3:467-485.
S. De V. Pepper et al., "Murine Gammaherpesvirus-68 Encodes Homologues of Thymidine Kinase and Glycoprotein H:Sequence, Expression, and Characterization of Pyrimidine Kinase Activity", 1996, Virology, vol. 219, 2:475-479.
H.W. Virgin, IV et al., "Complete Sequence and Genomic Analysis of Murine Gammaherpesvirus 68" 1997, Journal of Virology, vol. 71, 8:5894-5904.
V. Shankar et al., "A novel human airway mucin cDNA encodes a protein with unique tandem-repeat organization" Journal of Biochemistry, vol. 300, p. 295-298, 1994.
J.P. Stewart et al., 1996, "Identification and Characterization of Murine Gammaherpesvirus 68 gp 150: a Virion Membrane Glycoprotein", Journal of Virology, vol. 70, 6:3528-3535.
J.P. Stewart et al., 1994, "Characterization of Murine Gammaherpesvirus 68 Glycoprotein B (gB) Homolog: Similarity to Epstein-Barr Virus gB (gp 110)", Journal of Virology, vol. 68, 10:6496-6504.
R.J. Bowden et al., 1997, "Murine gammaherpesvirus 68 encodes tRNA-like sequences which ar expressed during latency", Journal of General Virology, vol. 78, 7:1675-1687.
M. Mackett et al., 1997, "Genetic content and preliminary transcriptional analysis of a representative region of murine gammaherpesvirus 68", Journal of General Virology, vol. 78, 6:1425-1433.
V. Shankar et al., 1994, "A novel human airway mucin cDNA encodes a protein with unique tandem-repeat organization", Biochemical Journal, vol. 300, 2:295-298.
NCI-CGAP, http://www.ncbi.nlm.nih.gov/ncicgap, GenBank Accession No. AI126846. NCBI website, Oct. 26, 1998.
GenBank Accession No. HSU14383. NCBI website, Dec. 31, 1994.
BACPAC Resources Home Page, http://www.chori.org/bacpac/bottom.htm.
S.P. Iadonato et al., "Large-scale MCD Mapping and Sequencing of Human Chromosome 7", (Unpublished) 1996, GenBank Accession No. AC000367.
Soares et al., Total fetus Nb2HF8_9w—Nucleotide, GenBank Accession No. AA463832.

* cited by examiner

*Primary Examiner* — Jennifer E Graser
(74) *Attorney, Agent, or Firm* — Locke Lord Bissell & Liddell, LLP

(57) ABSTRACT

This invention relates to isolated nucleic acids comprising genes of human chromosome 12q23-qter and the proteins encoded by these genes. Expression vectors and host cells containing such genes or fragments thereof, as well as antibodies to the proteins encoded by these nucleic acids are also included herein.

26 Claims, 24 Drawing Sheets

```
                10                          30                         50
                 .                           .                          .
        TCACGAGCTGCCCACGTCCTCTCCAGGAAGGGACCCCGGGTTCACGAGCTGCCCACGTCG
         T  S  C  P  R  P  L  Q  E  G  T  P  G  S  R  A  A  H  V  V 70                          90                        110
                 .                           .                          .
        TCTCCAGGAAGGGACCCGGGTCCACGAGCTGCCCACGTCCTCTCCAGGAAAGGACCCGGG
         S  R  K  G  P  G  S  T  S  C  P  R  P  L  Q  E  R  T  R  V 130                         150                        170
                 .                           .                          .
        TCCACGAGCTGGCCACGTCCTCTGCAGGAAGGGACCCCGGGTCCACGAGCTGCCCACGTC
         H  E  L  A  T  S  S  A  G  R  D  P  G  S  T  S  C  R  P 190                         210                        230
                 .                           .                          .
        CTCTCCAGGAAGGGACCCCGGGTTCACGAGCTGCCCACGTCCTCTCCAGGAAGGGACCCC
         L  Q  E  G  T  P  G  S  R  A  A  H  V  L  S  R  K  G  P  R 250                         270                        290
                 .                           .                          .
        GGGTCCACGAGCTGCCCACGTCCTCTCCAGGAAGGGACCCCGGGTCCACGAACTGCCCAC
         V  H  E  L  P  T  S  S  P  G  R  D  P  G  S  T  N  C  P  R 310                         330                        350
                 .                           .                          .
        GTCCTCTCCAGGAAGGGACCCCGGGTTCACGAGCTGCCCACGTCCTCTCCAGGAGGGGAC
         P  L  Q  E  G  T  P  G  S  R  A  A  H  V  L  S  R  R  G  H 370                         390                        410
                 .                           .                          .
        ACCGGGTTCACGAGCTGCCCACGCCCTCTCCAGGAAGGGACCCCGGGTTCATGAGCTGCC
         R  V  H  E  L  P  T  P  S  P  G  R  D  P  G  F  M  S  C  P 430                         450                        470
                 .                           .                          .
        CACGTCCTCTCCAGGAAGGGACCCGGGTCCACGAACTGCCCACGCCCTCTCCAGGAGGGG
         R  P  L  Q  E  G  T  R  V  H  E  L  P  T  P  S  P  G  G  D 490                         510                        530
                 .                           .                          .
        ACCCGGGTCCACGAGCTGCCCACGTCGTCAACGGGAAGGGACCCGGGTCCACGAGCTGCC
         P  G  P  R  A  A  H  V  V  N  G  K  G  P  G  S  T  S  C  P
```

Figure 3A

```
         550                    570                    590
          .                      .                      .
CACGTCCTCTCCAGGAAGGGACCCGGGTCCACGAACTGCCCACGCGCTCTCCAGGAGGGG
  R  P  L  Q  E  G  T  R  V  H  E  L  P  T  R  S  P  G  G  D 610                    630                    650
          .                      .                      .
ACACCGGGTTCACGAGCTGCCCACGCCCTCTCCAGGAAGGGACCCCGGGTTCACGAGCTG
  T  G  F  T  S  C  P  R  P  L  Q  E  G  T  P  G  S  R  A  A 670                    690                    710
          .                      .                      .
CCCACGTCCTCTCCAGGAGGGGACACCGGGTTCACGAGCTGCCCACGTCCTCTCCAGGAG
  H  V  L  S  R  R  G  H  R  V  H  E  L  P  T  S  S  P  G  G 730                    750                    770
          .                      .                      .
GGGACACCGGGTTCACGAGCTGCCCACGCCCTCTCCAGGAGGGGACACCGGGTTCACGAG
  D  T  G  F  T  S  C  P  R  P  L  Q  E  G  T  P  G  S  R  A 790                    810                    830
          .                      .                      .
CTGCCCACGTCCTCTCCAGGAAGGGACCCGGGTCCACGAGCTGCCCACGTCCTCTCCAGG
  A  H  V  L  S  R  K  G  P  G  S  T  S  C  P  R  P  L  Q  E 850                    870                    890
          .                      .                      .
AGGGGACACCGGGTTCACGAGCTGCCCACGCACTTTCCAGGAAGGGACCCCGGGTTCAGG
  G  T  P  G  S  R  A  A  H  A  L  S  R  K  G  P  R  V  Q  V 910                    930                    950
          .                      .                      .
TCTCCTGCCGGCCCACATCGTGCCTTTGTGTAAATCAGAAGAAAGATGAGGAACAGGCCC
  S  R  P  T  S  C  L  C  V  N  Q  K  K  D  E  E  Q  A  L 970                    990                   1010
          .                      .                      .
TCCTCTCTCTCCAGGCAGGCTTTGGTGGAGGGGCTGGATCTCCTGCCGCACCTTCCCTGG
  L  S  L  Q  A  G  F  G  G  G  A  G  S  P  A  A  P  S  L  A 1030                   1050                   1070
          .                      .                      .
CAGGGCACCCTGTGCTTGAGCCCCAGAACTGCAGGCGGCCGGCAGAGAAGGGGTCCATGA
  G  H  P  V  L  E  P  Q  N  C  R  R  P  A  E  K  G  S  M  M
```

Figure 3B

```
         1090                1110                1130
           .                   .                   .
TGGCGCCTCGGTGCGCAGCCTTGGACCTGCCCCCATGGACCTGGGAACCTCCCGGCTCTT
  A  P  R  C  A  A  L  D  L  P  P  W  T  E  P  P  G  S  S 1150                1170                1190
           .                   .                   .
CCCACTCGGGAAAGGAAGGCTCTGGGCATGGAGGTCGGCCAGGCCCCATCCCCGTACCCT
  H  S  G  K  E  G  S  G  H  G  G  R  P  G  P  I  P  V  P  W 1210                1230                1250
           .                   .                   .
GGCCCTTCTTCCTGCTTCCTGTTTGTCACTGCCCCGGGGCCTTTGCACCTGCATTCCCTC
  P  F  F  L  L  P  V  C  H  C  P  G  A  F  A  P  A  F  P  L 1270                1290                1310
           .                   .                   .
TCTCTAGACAGGGTTTCTCCTCATTGGCCAGGCTGGTCTCGAACTCCTGACCTCAGACGA
  S  R  Q  G  F  S  S  L  A  R  L  V  S  N  S  *

1330                1350                1370
           .                   .                   .
TCCACCTGCCTCAGCCTCCCGAAGTGTTGGGATTACAGGCACGAGCCACTGTGCCCGGCC 1390                1410                1430
           .                   .                   .
ATCATTCCTTTTTACTGCTGACTAATAGTCTGCTGTGTGAATCCACCGCTAGAAACCCAC 1450                1470                1490
           .                   .                   .
TCATCAGTTGATGGTCATGTGGGTTGCTTCTGCTATTCGCTTATTATGAACAGTGCTGGA 1510                1530                1550
           .                   .                   .
ATAAACGTTCCTGTGCACTCTTGGGCATACGCCTAGGAGTGGAACTGCTGGGTCAAAAAA

1570
           .
AAAAAAAAAAAAAAAAAAAAAA
```

Figure 3C

```
           10                  30                    50
            .                   .                     .
TCACGAGCTGCCCACGTCCTCTCCAGGAAGGGACCCCGGGTTCACGAGCTGCCCACGTCG
  T  S  C  P  R  P  L  Q  E  G  T  P  G  S  R  A  A  H  V  V 70                  90                   110
            .                   .                     .
TCTCCAGGAAGGGACCCGGGTCCACGAGCTGCCCACGTCCTCTCCAGGAAAGGACCCGGG
  S  R  K  G  P  G  S  T  S  C  P  R  P  L  Q  E  R  T  R  V 130                 150                   170
            .                   .                     .
TCCACGAGCTGGCCACGTCCTCTGCAGGAAGGGACCCCGGGTCCACGAGCTGCCCACGTC
  H  E  L  A  T  S  S  A  G  R  D  P  G  S  T  S  C  P  R  P 190                 210                   230
            .                   .                     .
CTCTCCAGGAAGGGACCCCGGGTTCACGAGCTGCCCACGTCCTCTCCAGGAAGGGACCCC
  L  Q  E  G  T  P  G  S  R  A  A  H  V  L  S  R  K  G  P  R 250                 270                   290
            .                   .                     .
GGGTCCACGAGCTGCCCACGTCCTCTCCAGGAAGGGACCCCGGGTCCACGAACTGCCCAC
  V  H  E  L  P  T  S  S  P  G  R  D  P  G  S  T  N  C  P  R 310                 330                   350
            .                   .                     .
GTCCTCTCCAGGAAGGGACCCCGGGTTCACGAGCTGCCCACGTCCTCTCCAGGAGGGGAC
  P  L  Q  E  G  T  P  G  S  R  A  A  H  V  L  S  R  R  G  H 370                 390                   410
            .                   .                     .
ACCGGGTTCACGAGCTGCCCACGCCCTCTCCAGGAAGGGACCCCGGGTTCATGAGCTGCC
  R  V  H  E  L  P  T  P  S  P  G  R  D  P  G  F  M  S  C  P 430                 450                   470
            .                   .                     .
CACGTCCTCTCCAGGAAGGGACCCGGGTCCACGAACTGCCCACGCCCTCTCCAGGAGGGG
  R  P  L  Q  E  G  T  R  V  H  E  L  P  T  P  S  P  G  G  D 490                 510                   530
            .                   .                     .
ACCCGGGTCCACGAGCTGCCCACGTCGTCAACGGGAAGGGACCCGGGTCCACGAGCTGCC
  P  G  P  R  A  A  H  V  V  N  G  K  G  P  G  S  T  S  C  P 550                 570                   590
```

Figure 4A

```
CACGTCCTCTCCAGGAAGGGACCCGGGTCCACGAACTGCCCACGCGCTCTCCAGGAGGGG
  R  P  L  Q  E  G  T  R  V  H  E  L  P  T  R  S  P  G  G  D 610                 630                 650
ACACCGGGTTCACGAGCTGCCCACGCCCTCTCCAGGAAGGGACCCCGGGTTCACGAGCTG
  T  G  F  T  S  C  P  R  P  L  Q  E  G  T  P  G  S  R  A  A 670                 690                 710
CCCACGTCCTCTCCAGGAGGGGACACCGGGTTCACGAGCTGCCCACGTCCTCTCCAGGAG
  H  V  L  S  R  R  G  H  R  V  H  E  L  P  T  S  S  P  G  G 730                 750                 770
GGGACACCGGGTTCACGAGCTGCCCACGCCCTCTCCAGGAGGGGACACCGGGTTCACGAG
  D  T  G  F  T  S  C  P  R  P  L  Q  E  G  T  P  G  S  R  A 790                 810                 830
CTGCCCACGTCCTCTCCAGGAAGGGACCCGGGTCCACGAGCTGCCCACGTCCTCTCCAGG
  A  H  V  L  S  R  K  G  P  G  S  T  S  C  P  R  P  L  Q  E 850                 870                 890
AGGGGACACCGGGTTCACGAGCTGCCCACGCACTTTCCAGGAAGGGACCCCGGGTTCAGG
  G  T  P  G  S  R  A  A  H  A  L  S  R  K  G  P  R  V  Q  V 910                 930                 950
TCTCCTGCCGGCCCACATCGTGCCTTTGTGTAAATCAGAAGAAAGATGAGGAACAGGCCC
  S  C  R  P  T  S  C  L  C  V  N  Q  K  K  D  E  E  Q  A  L 970                 990                1010
TCCTCTCTCTCCAGGCAGGCTTTGGTGGAGGGGCTGGATCTCCTGCCGCACCTTCCCTGG
  L  S  L  Q  A  G  F  G  G  A  G  S  P  A  A  P  S  L  A 1030                1050                1070
CAGGGCACCCTGTGCTTGAGCCCCAGAACTGCAGGCGGCCGGCAGAGAAGGGGTCCATGA
  G  H  P  V  L  E  P  Q  N  C  R  R  P  A  E  K  G  S  M  M 1090                1110                1130
TGGCGCCTCGGTGCGCAGCCTTGGACCTGCCCCCATGGACCTGGAGACAGGGTTTCTCCT
  A  P  R  C  A  A  L  D  L  P  P  W  T  W  R  Q  G  F  S  S
```

Figure 4B

```
          1150                1170                1190
           .                   .                   .
CATTGGCCAGGCTGGTCTCGAACTCCTGACCTCAGACGATCCACCTGCCTCAGCCTCCCG
   L    A    R    L    V    S    N    S    *

1210                1230                1250
           .                   .                   .
AAGTGTTGGGATTACAGGCACGAGCCACTGTGCCCGGCCATCATTCCTTTTTACTGCTGA 1270                1290                1310
           .                   .                   .
CTAATAGTCTGCTGTGTGAATCCACCGCTAGAAACCCACTCATCAGTTGATGGTCATGTG 1330                1350                1370
           .                   .                   .
GGTTGCTTCTGCTATTCGCTTATTATGAACAGTGCTGGAATAAACGTTCCTGTGCACTCT 1390                1410                1430
           .                   .                   .
TGGGCATACGCCTAGGAGTGGAACTGCTGGGTCAAAAAAAAAAAAAAAAAAAAAAAAAAA
```

```
            10                      30                      50
             .                       .                       .
TCACGAGCTGCCCACGTCCTCTCCAGGAAGGGACCCCGGGTTCACGAGCTGCCCACGTCG
 T  S  C  P  R  P  L  Q  E  G  T  P  G  S  R  A  A  H  V  V 70                      90                     110
             .                       .                       .
TCTCCAGGAAGGGACCCGGGTCCACGAGCTGCCCACGTCCTCTCCAGGAAAGGACCCGGG
 S  R  K  G  P  G  S  T  S  C  P  R  P  L  Q  E  R  T  R  V 130                     150                     170
             .                       .                       .
TCCACGAGCTGGCCACGTCCTCTGCAGGAAGGGACCCCGGGTCCACGAGCTGCCCACGTC
 H  E  L  A  T  S  S  A  G  R  D  P  G  S  T  S  C  P  R  P 190                     210                     230
             .                       .                       .
CTCTCCAGGAAGGGACCCCGGGTTCACGAGCTGCCCACGTCCTCTCCAGGAAGGGACCCC
 L  Q  E  G  T  P  G  S  R  A  A  H  V  L  S  R  K  G  P  R 250                     270                     290
             .                       .                       .
GGGTCCACGAGCTGCCCACGTCCTCTCCAGGAAGGGACCCCGGGTCCACGAACTGCCCAC
 V  H  E  L  P  T  S  S  P  G  R  D  P  G  S  T  N  C  P  R 310                     330                     350
             .                       .                       .
GTCCTCTCCAGGAAGGGACCCCGGGTTCACGAGCTGCCCACGTCCTCTCCAGGAGGGGAC
 P  L  Q  E  G  T  P  G  S  R  A  A  H  V  L  S  R  R  G  H 370                     390                     410
             .                       .                       .
ACCGGGTTCACGAGCTGCCCACGCCCTCTCCAGGAAGGGACCCCGGGTTCATGAGCTGCC
 R  V  H  E  L  P  T  P  S  P  G  R  D  P  G  F  M  S  C  P 430                     450                     470
             .                       .                       .
CACGTCCTCTCCAGGAAGGGACCCGGGTCCACGAACTGCCCACGCCCTCTCCAGGAGGGG
 R  P  L  Q  E  G  T  R  V  H  E  L  P  T  P  S  P  G  G  D 490                     510                     530
             .                       .                       .
ACCCGGGTCCACGAGCTGCCCACGTCGTCAACGGGAAGGGACCCGGGTCCACGAGCTGCC
 P  G  P  R  A  A  H  V  V  N  G  K  G  P  G  S  T  S  C  P
```

Figure 5A

```
       550                  570                  590
        .                    .                    .
CACGTCCTCTCCAGGAAGGGACCCGGGTCCACGAACTGCCCACGCGCTCTCCAGGAGGGG
 R  P  L  Q  E  G  T  R  V  H  E  L  P  T  R  S  P  G  G  D 610                  630                  650
        .                    .                    .
ACACCGGGTTCACGAGCTGCCCACGCCCTCTCCAGGAAGGGACCCCGGGTTCACGAGCTG
 T  G  F  T  S  C  P  R  P  L  Q  E  G  T  P  G  S  R  A  A 670                  690                  710
        .                    .                    .
CCCACGTCCTCTCCAGGAGGGGACACCGGGTTCACGAGCTGCCCACGTCCTCTCCAGGAG
 H  V  L  S  R  R  G  H  R  V  H  E  L  P  T  S  S  P  G  G 730                  750                  770
        .                    .                    .
GGGACACCGGGTTCACGAGCTGCCCACGCCCTCTCCAGGAGGGGACACCGGGTTCACGAG
 D  T  G  F  T  S  C  P  R  P  L  Q  E  G  T  P  G  S  R  A 790                  810                  830
        .                    .                    .
CTGCCCACGTCCTCTCCAGGAAGGGACCCGGGTCCACGAGCTGCCCACGTCCTCTCCAGG
 A  H  V  L  S  R  K  G  P  G  S  T  S  C  P  R  P  L  Q  E 850                  870                  890
        .                    .                    .
AGGGGACACCGGGTTCACGAGCTGCCCACGCACTTTCCAGGAAGGGACCCCGGGTTCAGG
 G  T  P  G  S  R  A  A  H  A  L  S  R  K  G  P  R  V  Q  V 910                  930                  950
        .                    .                    .
TCTCCTGCCGGCCCACATCGTGCCTTTGTGTAAATCAGAAGAAAGATGAGGAACAGGCCC
 S  C  R  P  T  S  C  L  C  V  N  Q  K  K  D  E  E  Q  A  L 970                  990                  1010
        .                    .                    .
TCCTCTCTCTCCAGGCAGGCTTTGGTGGAGGGGCTGGATCTCCTGCCGCACCTTCCCTGG
 L  S  L  Q  A  G  F  G  G  G  A  G  S  P  A  A  P  S  L  A 1030                 1050                 1070
        .                    .                    .
CAGGGCACCCTGTGCTTGAGCCCCAGAACTGCAGGCGGCCGGCAGAGAAGGGGTCCATGA
 G  H  P  V  L  E  P  Q  N  C  R  R  P  A  E  K  G  S  M  M
```

Figure 5B

```
          1090                1110                1130
           .                   .                   .
TGGCGCCTCGGTGCGCAGCCTTGGACCTGCCCCCATGGACCTGGGAACCTCCCGGCTCTT
 A   P   R   C   A   A   L   D   L   P   P   W   T   E   P   P   G   S   S 1150                1170                1190
           .                   .                   .
CCCACTCGGGAAAGGAAGGCTCTGGGCATGGAGCTTTATTGAGGTATAGTTGACAATTCA
 H   S   G   K   E   G   S   G   H   G   A   L   L   R   Y   S   *

1210                1230                1250
           .                   .                   .
GGACGGTGTGCACTCAAGGTATGCAGCATCACAACCTGACACACGTAGGCATTGTGAAAT 1270                1290                1310
           .                   .                   .
GAGTCCCACAATTGGGCTAATTAACACACCCATCACCTTACATGGTTACTTCTTTCTGTG 1330                1350                1370
           .                   .                   .
GTGAGAACACTAAATTTTAAATAGAGGACACACAGCCTGGGCAACATAGTGAGACCCTGT 1390                1410                1430
           .                   .                   .
CTCTACAAATATAAAAAAATTATCTGGACGTGGTGGTGCACACCTGTGGTCCCAGCTACT 1450                1470                1490
           .                   .                   .
TGGGAAGCTGAGGCTGGAGAATCACTTGAGCCTGGGAGGCGGAGGTTGCGGTGCACTCCA 1510                1530                1550
           .                   .                   .
GCCTGGGCGACAGAGGGAGGCCCTATCTCAAAATAAATAAATAAAGGACACATTCTTATC

1570
           .
AAAAAAAAAAAAAAAA
```

Figure 5C

```
          10                      30                      50
           .                       .                       .
TCACGAGCTGCCCACGTCCTCTCCAGGAAGGGACCCCGGGTTCACGAGCTGCCCACGTCG
 T  S  C  P  R  P  L  Q  E  G  T  P  G  S  R  A  A  H  V  V 70                      90                     110
           .                       .                       .
TCTCCAGGAAGGGACCCGGGTCCACGAGCTGCCCACGTCCTCTCCAGGAAAGGACCCGGG
 S  R  K  G  P  G  S  T  S  C  P  R  P  L  Q  E  R  T  R  V 130                     150                     170
           .                       .                       .
TCCACGAGCTGGCCACGTCCTCTGCAGGAAGGGACCCCGGGTCCACGAGCTGCCCACGTC
 H  E  L  A  T  S  S  A  G  R  D  P  G  S  T  S  C  P  R  P 190                     210                     230
           .                       .                       .
CTCTCCAGGAAGGGACCCCGGGTTCACGAGCTGCCCACGTCCTCTCCAGGAAGGGACCCC
 L  Q  E  G  T  P  G  S  R  A  A  H  V  L  S  R  K  G  P  R 250                     270                     290
           .                       .                       .
GGGTCCACGAGCTGCCCACGTCCTCTCCAGGAAGGGACCCCGGGTCCACGAACTGCCCAC
 V  H  E  L  P  T  S  S  P  G  R  D  P  G  S  T  N  C  P  R 310                     330                     350
           .                       .                       .
GTCCTCTCCAGGAAGGGACCCCGGGTTCACGAGCTGCCCACGTCCTCTCCAGGAGGGGAC
 P  L  Q  E  G  T  P  G  S  R  A  A  H  V  L  S  R  R  G  H 370                     390                     410
           .                       .                       .
ACCGGGTTCACGAGCTGCCCACGCCCTCTCCAGGAAGGGACCCCGGGTTCATGAGCTGCC
 R  V  H  E  L  P  T  P  S  P  G  R  D  P  G  F  M  S  C  P 430                     450                     470
           .                       .                       .
CACGTCCTCTCCAGGAAGGGACCCGGGTCCACGAACTGCCCACGCCCTCTCCAGGAGGGG
 R  P  L  Q  E  G  T  R  V  H  E  L  P  T  P  S  P  G  G  D 490                     510                     530
           .                       .                       .
ACCCGGGTCCACGAGCTGCCCACGTCGTCAACGGGAAGGGACCCGGGTCCACGAGCTGCC
 P  G  P  R  A  A  H  V  V  N  G  K  G  P  G  S  T  S  C  P
```

Figure 6A

```
            550                   570                    590
              .                     .                      .
CACGTCCTCTCCAGGAAGGGACCCGGGTCCACGAACTGCCCACGCGCTCTCCAGGAGGGG
  R  P  L  Q  E  G  T  R  V  H  E  L  P  T  R  S  P  G  G  D 610                   630                    650
              .                     .                      .
ACACCGGGTTCACGAGCTGCCCACGCCCTCTCCAGGAAGGGACCCCGGGTTCACGAGCTG
  T  G  F  T  S  C  P  R  P  L  Q  E  G  T  P  G  S  R  A  A 670                   690                    710
              .                     .                      .
CCCACGTCCTCTCCAGGAGGGGACACCGGGTTCACGAGCTGCCCACGTCCTCTCCAGGAG
  H  V  L  S  R  R  G  H  R  V  H  E  L  P  T  S  S  P  G  G 730                   750                    770
              .                     .                      .
GGGACACCGGGTTCACGAGCTGCCCACGCCCTCTCCAGGAGGGGACACCGGGTTCACGAG
  D  T  G  F  T  S  C  P  R  P  L  Q  E  G  T  P  G  S  R  A 790                   810                    830
              .                     .                      .
CTGCCCACGTCCTCTCCAGGAAGGGACCCGGGTCCACGAGCTGCCCACGTCCTCTCCAGG
  A  H  V  L  S  R  K  G  P  G  S  T  S  C  P  R  P  L  Q  E 850                   870                    890
              .                     .                      .
AGGGGACACCGGGTTCACGAGCTGCCCACGCACTTTCCAGGAAGGGACCCCGGGTTCAGG
  G  T  P  G  S  R  A  A  H  A  L  S  R  K  G  P  R  V  Q  V 910                   930                    950
              .                     .                      .
TCTCCTGCCGGCCCACATCGTGCCTTTGTGTAAATCAGAAGAAAGATGAGGAACAGGCCC
  S  C  R  P  T  S  C  L  C  V  N  Q  K  K  D  E  E  Q  A  L 970                   990                   1010
              .                     .                      .
TCCTCTCTCTCCAGGCAGGCTTTGGTGGAGGGGCTGGATCTCCTGCCGCACCTTCCCTGG
  L  S  L  Q  A  G  F  G  G  G  A  G  S  P  A  A  P  S  L  A 1030                  1050                   1070
              .                     .                      .
CAGGGCACCCTGTGCTTGAGCCCCAGAACTGCAGGCGGCCGGCAGAGAAGGGGTCCATGA
  G  H  P  V  L  E  P  Q  N  C  R  R  P  A  E  K  G  S  M  M

Figure 6B
```

```
         1090                1110                1130
             .                  .                   .
TGGCGCCTCGGTGCGCAGCCTTGGACCTGCCCCCATGGACCTGGATGCCAGTGATGCCTG
 A  P  R  C  A  A  L  D  L  P  P  W  T  W  M  P  V  M  P  E 1150                1170                1190
             .                  .                   .
AGGTCTGCAGGGCAGTGCATACGCTCACCGCCTGGCCGCTCAGGAGCCTGTGCTTGACCC
 V  C  R  A  V  H  T  L  T  A  W  P  L  R  S  L  C  L  T  P 1210                1230                1250
             .                  .                   .
CCAAATCCGCCCCCCAACTCCCTGTTACCGGCTCACTCCTTCCATGAGGGGCCTTCCCCA
 K  S  A  P  Q  L  P  V  T  G  S  L  L  P  *

1270                1290                1310
             .                  .                   .
GGGACAGCCGATGCTCTCCTGATGGCTCCTGCCCTTGCAGAGTGCTGCCCCCGCCTGCCC 1330                1350                1370
             .                  .                   .
ACCTGGCCTGGACCCTCGCCTGAGCCCCCTCAGGGCTCTGCGCCACCTCAACCCAGGCGT 1390                1410                1430
             .                  .                   .
TTGTTCCGCAGGAACCTCCCGGCTCTTCCCACTCGGGAAAGGAAGGCTCTGGGCATGGAG 1450                1470                1490
             .                  .                   .
GTCGGCCAGGCCCCATCCCCGTACCCTGGCCCTTCTTCCTGCTTCCTGTTTGTCACTGCC 1510                1530                1550
             .                  .                   .
CCGGGGCCTTTGCACCTGCATTCCCTCTCTCTGTGAGTGTCCTGGGGCCCGTTACCCACG 1570                1590                1610
             .                  .                   .
TCACCGTCCCAGGATACCTTTTCTTTTCTTTCTCTCTCCAGCTTTATTGAGGTATAGT 1630                1650                1670
             .                  .                   .
TGACAATTCAGGACGGTGTGCACTCAAGGTATGCAGCATCACAACCTGACACACGTAGGC 1690                1710                1730
             .                  .                   .
ATTGTGAAATGAGTCCCACAATTGGGCTAATTAACACACCCATCACCTTACATGGTTACT
```

Figure 6C

```
         1750              1770              1790
           .                 .                 .
TCTTTCTGTGGTGAGAACACTAAATTTTAAATAGAGGACACACAGCCTGGGCAACATAGT 1810              1830              1850
           .                 .                 .
GAGACCCTGTCTCTACAAATATAAAAAAATTATCTGGACGTGGTGGTGCACACCTGTGGT 1870              1890              1910
           .                 .                 .
CCCAGCTACTTGGGAAGCTGAGGCTGGAGAATCACTTGAGCCTGGGAGGCGGAGGTTGCG 1930              1950              1970
           .                 .                 .
GTGCACTCCAGCCTGGGCGACAGAGGGAGGCCCTATCTCAAAATAAATAAATAAAGGACA 1990              2010
           .                 .
CATTCTTATCAAAAAAAAAAAAAAAAAAAA
```

Figure 6D

```
              10                      30                      50
              .                       .                       .
TCACGAGCTGCCCACGTCCTCTCCAGGAAGGGACCCCGGGTTCACGAGCTGCCCACGTCG
 T  S  C  P  R  P  L  Q  E  G  T  P  G  S  R  A  A  H  V  V 70                      90                     110
              .                       .                       .
TCTCCAGGAAGGGACCCGGGTCCACGAGCTGCCCACGTCCTCTCCAGGAAAGGACCCGGG
 S  R  K  G  P  G  S  T  S  C  P  R  P  L  Q  E  R  T  R  V 130                     150                     170
              .                       .                       .
TCCACGAGCTGGCCACGTCCTCTGCAGGAAGGGACCCCGGGTCCACGAGCTGCCCACGTC
 H  E  L  A  T  S  S  A  G  R  D  P  G  S  T  S  C  P  R  P 190                     210                     230
              .                       .                       .
CTCTCCAGGAAGGGACCCCGGGTTCACGAGCTGCCCACGTCCTCTCCAGGAAGGGACCCC
 L  Q  E  G  T  P  G  S  R  A  A  H  V  L  S  R  K  G  P  R 250                     270                     290
              .                       .                       .
GGGTCCACGAGCTGCCCACGTCCTCTCCAGGAAGGGACCCCGGGTCCACGAACTGCCCAC
 V  H  E  L  P  T  S  S  P  G  R  D  P  G  S  T  N  C  P  R 310                     330                     350
              .                       .                       .
GTCCTCTCCAGGAAGGGACCCCGGGTTCACGAGCTGCCCACGTCCTCTCCAGGAGGGGAC
 P  L  Q  E  G  T  P  G  S  R  A  A  H  V  L  S  R  R  G  H 370                     390                     410
              .                       .                       .
ACCGGGTTCACGAGCTGCCCACGCCCTCTCCAGGAAGGGACCCCGGGTTCATGAGCTGCC
 R  V  H  E  L  P  T  P  S  P  G  R  D  P  G  F  M  S  C  P 430                     450                     470
              .                       .                       .
CACGTCCTCTCCAGGAAGGGACCCGGGTCCACGAACTGCCCACGCCCTCTCCAGGAGGGG
 R  P  L  Q  E  G  T  R  V  H  E  L  P  T  P  S  P  G  G  D 490                     510                     530
              .                       .                       .
ACCCGGGTCCACGAGCTGCCCACGTCGTCAACGGGAAGGGACCCGGGTCCACGAGCTGCC
 P  G  P  R  A  A  H  V  V  N  G  K  G  P  G  S  T  S  C  P
```

Figure 7A

```
                550                         570                       590
                 .                           .                         .
     CACGTCCTCTCCAGGAAGGGACCCGGGTCCACGAACTGCCCACGCGCTCTCCAGGAGGGG
       R  P  L  Q  E  G  T  R  V  H  E  L  P  T  R  S  P  G  G  D 610                         630                       650
                 .                           .                         .
     ACACCGGGTTCACGAGCTGCCCACGCCCTCTCCAGGAAGGGACCCCGGGTTCACGAGCTG
       T  G  F  T  S  C  P  R  P  L  Q  E  G  T  P  G  S  R  A  A 670                         690                       710
                 .                           .                         .
     CCCACGTCCTCTCCAGGAGGGGACACCGGGTTCACGAGCTGCCCACGTCCTCTCCAGGAG
       H  V  L  S  R  R  G  H  R  V  H  E  L  P  T  S  S  P  G  G 730                         750                       770
                 .                           .                         .
     GGGACACCGGGTTCACGAGCTGCCCACGCCCTCTCCAGGAGGGGACACCGGGTTCACGAG
       D  T  G  F  T  S  C  P  R  P  L  Q  E  G  T  P  G  S  R  A 790                         810                       830
                 .                           .                         .
     CTGCCCACGTCCTCTCCAGGAAGGGACCCGGGTCCACGAGCTGCCCACGTCCTCTCCAGG
       A  H  V  L  S  R  K  G  P  G  S  T  S  C  P  R  P  L  Q  E 850                         870                       890
                 .                           .                         .
     AGGGGACACCGGGTTCACGAGCTGCCCACGCACTTTCCAGGAAGGGACCCCGGGTTCAGG
       G  T  P  G  S  R  A  A  H  A  L  S  R  K  G  P  R  V  Q  V 910                         930                       950
                 .                           .                         .
     TCTCCTGCCGGCCCACATCGTGCCTTTGTGTAAATCAGAAGAAAGATGAGGAACAGGCCC
       S  C  R  P  T  S  C  L  C  V  N  Q  K  K  D  E  E  Q  A  L 970                         990                      1010
                 .                           .                         .
     TCCTCTCTCTCCAGGCAGGCTTTGGTGGAGGGGCTGGATCTCCTGCCGCACCTTCCCTGG
       L  S  L  Q  A  G  F  G  G  G  A  G  S  P  A  A  P  S  L  A 1030                        1050                      1070
                 .                           .                         .
     CAGGGCACCCTGTGCTTGAGCCCCAGAACTGCAGGCGGCCGGCAGAGAAGGGGTCCATGA
       G  H  P  V  L  E  P  Q  N  C  R  R  P  A  E  K  G  S  M  M

Figure 7B
```

```
       1090                  1110                 1130
         .                    .                    .
TGGCGCCTCGGTGCGCAGCCTTGGACCTGCCCCCATGGACCTGGGAACCTCCCGGCTCTT
 A  P  R  C  A  A  L  D  L  P  P  W  T  W  E  P  P  G  S  S 1150                  1170                 1190
         .                    .                    .
CCCACTCGGGAAAGGAAGGCTCTGGGCATGGAGGTCGGCCAGGCCCCATCCCCGTACCCT
 H  S  G  K  E  G  S  G  H  G  G  R  P  G  P  I  P  V  P  W 1210                  1230                 1250
         .                    .                    .
GGCCCTTCTTCCTGCTTCCTGTTTGTCACTGCCCCGGGGCCTTTGCACCTGCATTCCCTC
 P  F  F  L  L  P  V  C  H  C  P  G  A  F  A  P  A  F  P  L 1270                  1290                 1310
         .                    .                    .
TCTCTGTGAGTGTCCTGGGGCCCGTTACCCACGTCACCGTCCCAGGATACCTTTTCTTTT
 S  V  S  V  L  G  P  V  T  H  V  T  V  P  G  Y  L  F  F  S 1330                  1350                 1370
         .                    .                    .
CTTTCTCTCTCCAGCTTTATTGAGGTATAGTTGACAATTCAGGACGGTGTGCACTCAA
 F  S  L  S  S  F  I  E  V  *

1390                  1410                 1430
         .                    .                    .
GGTATGCAGCATCACAACCTGACACACGTAGGCATTGTGAAATGAGTCCCACAATTGGGC 1450                  1470                 1490
         .                    .                    .
TAATTAACACACCCATCACCTTACATGGTTACTTCTTTCTGTGGTGAGAACACTAAATTT 1510                  1530                 1550
         .                    .                    .
TAAATAGAGGACACACAGCCTGGGCAACATAGTGAGACCCTGTCTCTACAAATATAAAAA 1570                  1590                 1610
         .                    .                    .
AATTATCTGGACGTGGTGGTGCACACCTGTGGTCCCAGCTACTTGGGAAGCTGAGGCTGG 1630                  1650                 1670
         .                    .                    .
AGAATCACTTGAGCCTGGGAGGCGGAGGTTGCGGTGCACTCCAGCCTGGGCGACAGAGGG
```

Figure 7C

```
            1690              1710              1730
             .                 .                 .
AGGCCCTATCTCAAAATAAATAAATAAAGGACACATTCTTATCAAAAAAAAAAAAAAAA

AAAA
```

Figure 7D

Alternatively Spliced Variants from Gene 214

Alternatively Spliced Variants from Gene 214

Northern blot analysis of Gene 214

>Gene 214 Exon_A
TCACGAGCTGCCCACGTCCTCTCCAGGAAGGGACCCCGGGTTCACGAGCTGCCCACGTCG
TCTCCAGGAAGGGACCCGGGTCCACGAGCTGCCCACGTCCTCTCCAGGAAAGGACCCGGG
TCCACGAGCTGGCCACGTCCTCTGCAGGAAGGGACCCCGGGTCCACGAGCTGCCCACGTC
CTCTCCAGGAAGGGACCCCGGGTTCACGAGCTGCCCACGTCCTCTCCAGGAAGGGACCCC
GGGTCCACGAGCTGCCCACGTCCTCTCCAGGAAGGGACCCCGGGTCCACGAACTGCCCAC
GTCCTCTCCAGGAAGGGACCCCGGGTTCACGAGCTGCCCACGTCCTCTCCAGGAGGGGAC
ACCGGGTTCACGAGCTGCCCACGCCCTCTCCAGGAAGGGACCCCGGGTTCATGAGCTGCC
CACGTCCTCTCCAGGAAGGGACCCGGGTCCACGAACTGCCCACGCCCTCTCCAGGAGGGG
ACCCGGGTCCACGAGCTGCCCACGTCGTCAACGGGAAGGGACCCGGGTCCACGAGCTGCC
CACGTCCTCTCCAGGAAGGGACCCGGGTCCACGAACTGCCCACGCGCTCTCCAGGAGGGG
ACACCGGGTTCACGAGCTGCCCACGCCCTCTCCAGGAAGGGACCCCGGGTTCACGAGCTG
CCCACGTCCTCTCCAGGAGGGGACACCGGGTTCACGAGCTGCCCACGTCCTCTCCAGGAG
GGGACACCGGGTTCACGAGCTGCCCACGCCCTCTCCAGGAGGGGACACGGGTTCACGAG
CTGCCCACGTCCTCTCCAGGAAGGGACCCGGGTCCACGAGCTGCCCACGTCCTCTCCAGG
AGGGGACACCGGGTTCACGAGCTGCCCACGCACTTTCCAGGAAGGGACCCCGGGTTCAGG
TCTCCTGCCGGCCCACATCGTGCCTTTGTGTAAATCAGAAGAAAGATGAGGAACAGGCCC
TCCTCTCTCTCCAGGCAGGCTTTGGTGGAGGGGCTGGATCTCCTGCCGCACCTTCCCTGG
CAGGGCACCCTGTGCTTGAGCCCCAGAACTGCAGGCGGCCGGCAGAGAAGGGGTCCATGA
TGGCGCCTCGGTGCGCAGCCTTGGACCTGCCCCATGGACCTGG >Gene 214 Exon_B
AGACAGGGTTTCTCCTCATTGGCCAGGCTGGTCTCGAACTCCTGACCTCAGACGATCCAC
CTGCCTCAGCCTCCCGAAGTGTTGGGATTACAGGCACGAGCCACTGTGCCCGGCCATCAT
TCCTTTTTACTGCTGACTAATAGTCTGCTGTGTGAATCCACCGCTAGAAACCCACTCATC
AGTTGATGGTCATGTGGGTTGCTTCTGCTATTCGCTTATTATGAACAGTGCTGGAATAAA
CGTTCCTGTGCACTCTTGGGCATACGCCTAGGAGTGGAACTGCTGGGTC >Gene 214 Exon C
GAACCTCCCGGCTCTTCCCACTCGGGAAAGGAAGGCTCTGGGCATGGAGGTCGGCCAGGC
CCCATCCCCGTACCCTGGCCCTTCTTCCTGCTTCCTGTTTGTCACTGCCCCGGGGCCTTT
GCACCTGCATTCCCTCTCTCT >Gene 214 Exon C.2
GAACCTCCCGGCTCTTCCCACTCGGGAAAGGAAGGCTCTGGGCATGGAG >Gene 214 Exon E.1
ATGCCAGTGATGCCTGAGGTCTGCAGGGCAGTGCATACGCTCACCGCCTGGCCGCTCAGG
AGCCTGTGCTTGACCCCAAATCCGCCCCCAACTCCCTGTTACCGGCTCACTCCTTCCA
TGAGGGGCCTTCCCCAGGGACAGCCGATGCTCTCCTGATGGCTCCTGCCCTTGCAGAGTG
CTGCCCCCGCCTGCCCACCTGGCCTGGACCCTCGCCTGAGCCCCCTCAGGGCTCTGCGCC
ACCTCAACCCAGGCGTTTGTTCCGCAGGAACCTCCCGGCTCTTCCCACTCGGGAAAGGAA
GGCTCTGGGCATGGAGGTCGGCCAGGCCCCATCCCCGTACCCTGGCCCTTCTTCCTGCTT
CCTGTTTGTCACTGCCCCGGGGCCTTTGCACCTGCATTCCCTCTCTCTGTGAGTGTCCTG
GGGCCCGTTACCCACGTCACCGTCCCAGGATACCTTTTCTTTTCTTTCTCTCTCTCCAGC
TTTATTGAGGTATAGTTGACAATTCAGGACGGTGTGCACTCAAGGTATGCAGCATCACAA
CCTGACACACGTAGGCATTGTGAAATGAGTCCCACCAATTGGGCTAATTAACACACCCATC
ACCTTACATGGTTACTTCTTTCTGTGGTGAGAACACTAAATTTTAAATAGAGGACACACA
GCCTGGGCAACATAGTGAGACCCTGTCTCTACAAATATAAAAAAATTATCTGGACGTGGT
GGTGCACACCTGTGGTCCCAGCTACTTGGGAAGCTGAGGCTGGAGAATCACTTGAGCCTG
GGAGGCGGAGGTTGCGGTGCACTCCAGCCTGGGCGACAGAGGGAGGCCCTATCTCAAAAT
AAATAAATAAAGGACACATTCTTATC

FIGURE 10A

>Gene 214 Exon E.2
CTTTATTGAGGTATAGTTGACAATTCAGGACGGTGTGCACTCAAGGTATGCAGCATCACA
ACCTGACACACGTAGGCATTGTGAAATGAGTCCCACAATTGGGCTAATTAACACACCCAT
CACCTTACATGGTTACTTCTTTCTGTGGTGAGAACACTAAATTTTAAATAGAGGACACAC
AGCCTGGGCAACATAGTGAGACCCTGTCTCTACAAATATAAAAAAATTATCTGGACGTGG
TGGTGCACACCTGTGGTCCCAGCTACTTGGGAAGCTGAGGCTGGAGAATCACTTGAGCCT
GGGAGGCGGAGGTTGCGGTGCACTCCAGCCTGGGCGACAGAGGGAGGCCCTATCTCAAAA
TAAATAAATAAAGGACACATTCTTATC >Gene 214 Exon E.3
GAACCTCCCGGCTCTTCCCACTCGGGAAAGGAAGGCTCTGGGCATGGAGGTCGGCCAGGC
CCCATCCCCGTACCCTGGCCCTTCTTCCTGCTTCCTGTTTGTCACTGCCCCGGGGCCTTT
GCACCTGCATTCCCTCTCTCTGTGAGTGTCCTGGGGCCCGTTACCCACGTCACCGTCCCA
GGATACCTTTTCTTTTCTTTCTCTCTCCAGCTTTATTGAGGTATAGTTGACAATTCAG
GACGGTGTGCACTCAAGGTATGCAGCATCACAACCTGACACACGTAGGCATTGTGAAATG
AGTCCCACAATTGGGCTAATTAACACACCCATCACCTTACATGGTTACTTCTTTCTGTGG
TGAGAACACTAAATTTTAAATAGAGGACACACAGCCTGGGCAACATAGTGAGACCCTGTC
TCTACAAATATAAAAAAATTATCTGGACGTGGTGGTGCACACCTGTGGTCCCAGCTACTT
GGGAAGCTGAGGCTGGAGAATCACTTGAGCCTGGGAGGCGGAGGTTGCGGTGCACTCCAG
CCTGGGCGACAGAGGGAGGCCCTATCTCAAAATAAATAAATAAAGGACACATTCTTATC >Gene 214 Exon F
CGGGCGTGTATATCTCTTCATAGAGAGCGCTCAGACAGCGTGCGTTAATCTGCGTCGATA
TATAGAGATCTTTATCACTGAGTAGATAGAACGTACATGAATGTACGAACAGTCCAGACG
AGTAACTTGACTAGGATAAGATAGACAGTACCAACTAATGAGACAAGAAGAGGGAATCAT
ATAGAATCATGTAGTCTGAGTCTAGCGAGTGTCGACATGATCACAAGCGAAATACAGACT
ATGAGAAGAGGTAGAAATAATAAGTANACTGAGAAGAGAGGTCATATGTACATACAAATC
AGTAAAGCAATAGAAATTGAATACATTATAAGCCACAGTTACAGAATTAGCCTAATTTAA
CAACCATGGCAAGCGAGTTATATCAAACATAGAAGAGTAAACTCTATCGACCATGGGTAG
GAACGAATAAAGGCGTCGAGAAGACAATAAGAATGCGTGTTAAACAGCAATACAAGAGAA
TAGCACCACTGAAGCAGACCAAAGGCGTCACCGGGGAAGTAGGGAAGAGGCACCTCACAA
GGAGAGGAAAGGGCAGTCCTGATTTTGAAAATTTCAGTGAAAAGACAGTGTTGTTCCCGG
AGGCAGCTTAGTGATCCCGCATCGACTCTGAAGAGGACCCTGAGGGTAGGGATTTTTGG
GCCTGACCGGCCTATGCTGAACGCCCACCGGGAATTCAGGGAGAAACACGGGGCCCCGGC
TTCCAGGAGAGCAGCCAGGCCACAGCCCTGAGGACGGGCAAACCCCACCCAGGCACGGTG
AGAGGGAGGCCGCCCAGGCCTGGGGCCTGGCGGCAGGGGATGAAGTGGACCAGAGCCCCG
CAAATCCTAACGTGGGTGAGCAGTGAGCCTGTGTGGCTGCGAGTGGCTCCGTTTTGGGGC
TGTTTGTTCCTGCAGCAAATGATGCCAGCCCTGACGGAACCAGTGCACGTCCACCACGAG
CTGCCCACGTCCTCTCCAGGAAGGGACCCGGGTCCACGAGCTGCCCACGTCCTCTCCAGG
AAGGGACC

FIGURE 10B

HUMAN GENES RELATING TO RESPIRATORY DISEASES AND OBESITY

RELATED APPLICATIONS

This application is a divisional application of U.S. patent application Ser. No. 10/743,704, now U.S. Pat. No. 7,407,804, filed on Dec. 22, 2003, which is a divisional application of U.S. patent application Ser. No. 09/627,465, now U.S. Pat. No. 6,737,519, filed on Jul. 28, 2000, which claims the benefit of U.S. Provisional Application Ser. No. 60/146,336 filed Jul. 30, 1999 and U.S. Provisional Application Ser. No. 60/211,749 filed Jun. 14, 2000, the entire teachings of all are incorporated herein by reference.

FIELD OF THE INVENTION

The present invention relates generally to isolated nucleic acids and the classification of the same. The invention more particularly relates to a novel gene and novel nucleic acids related to asthma and other respiratory diseases and the classification and therapeutic and diagnostic uses of this gene.

BACKGROUND

Wilkinson et al. showed linkage of asthma to markers on human chromosome 12 (*Genomics*, 53: 251-259 (1998)). In addition, Wilson et al. has shown that obesity may be linked to asthma (*Arch. Intern. Med.* 159: 2513-14 (1999)). In particular chromosomal region 12q23-qter has been linked to a variety of genetic disorders including male germ cell tumors, histidinemia, growth retardation with deafness and mental retardation, deficiency of Acyl-CoA dehydrogenase, spinal muscular atrophy, Darier disease, cardiomyopathy, Spinocerebellar ataxia-2, brachydactyl), Mevalonicaciduria, Hyperimmunoglobulinemia D, Noonan syndrome-1, Cardiofaciocutaneous syndrome, spinal muscular atrophy-4, tyrosinemia, phenylketonuria, B-cell non-Hodgkin lymphoma, Ulnar-mammary syndrome, Holt-Oram syndrome, Scapuloperoneal spinal muscular atrophy, alcohol intolerance, MODY, Diabetes mellitus, noninsulin-dependent, 2 and diabetes mellitus insulin-dependent (See National Center for Biotechnology Information: at the website of: (hypertext transfer protocol, (i.e., http), world wide web (i.e., www), National Center for Biotechnology Information (ncbi). National Library of Medicine (nlm). National Institutes of Health (NIH). Government (gov)/omim.). Although this region appears to contain genes affecting these disorders few genes have been discovered. There is a need in the art for identifying specific genes for such disorders because they are also associated with obesity and lung disease, particularly inflammatory lung disease phenotypes such as Chronic Obstructive Lung Disease (COPD), Adult Respiratory Distress Syndrome (ARDS), and asthma. Identification and characterization of such genetic compositions will make possible the development of effective diagnostics and therapeutic means to treat lung related disorders as well as the other diseases described herein.

SUMMARY OF THE INVENTION

This invention relates to Gene 214 located on chromosome 12q23-qter. Nucleic acids comprising all or a part of, or complementary fragments of Gene 214 and cDNA are described in various embodiments. Vectors and host cells containing the nucleic acids herein described are also included in this invention. These nucleic acids can be used in therapeutic applications for a multitude of diseases either through the overexpression of a recombinant nucleic acid comprising all or a portion of a Gene 214 gene, or by the use of these oligonucleotides and genes to modulate the expression of an endogenous gene or the activity of an endogenous gene product. Examples of therapeutic approaches include anti-sense inhibition of gene expression, gene therapy, monoclonal antibodies that specifically bind to the gene products, and the like. In vitro expression of the recombinant gene products can also be obtained.

Diagnostic methods are also described which utilize all or part of the nucleic acids of this invention. Such nucleic acids can be used, for example, as part of diagnostic methods to identify Gene 214 nucleic acids to screen for a predisposition to various genetic diseases. In addition, nucleic acids described herein can be used to identify chromosomal abnormalities within the chromosomal region 12q23-qter.

Further, this invention identifies various single nucleotide polymorphisms (SNPs) within several of the nucleic acids described herein. Some of these polymorphisms also comprise changes to the polypeptides of the present invention. The SNPs, together with the wild-type alleles can be used to prepare specific probes for detection of various disease states in an individual. Thus, in one embodiment, this invention provides a method of detecting chromosome abnormalities on chromosome 12q23-qter.

Proteins, polypeptides, and peptides encoded by all or a part of the nucleic acids comprising Gene 214 are included in this invention. Such amino acid sequences are useful for diagnostic and therapeutic purposes. Further, antibodies can be raised against all or a part of these amino acid sequences for specific diagnostic and therapeutic methods requiring such antibodies. These antibodies can be polyclonal, monoclonal, or antibody fragments.

In a further embodiment, vectors and host cells containing vectors which comprise all or a portion of the nucleic acid sequences of this invention can be constructed for nucleic acid preparations, including anti-sense, and/or for expression of encoded proteins and polypeptides. Such host cells can be prokaryotic or eukaryotic cells.

Still another embodiment of the invention comprises a method of identifying a protein which is a candidate for being involved in asthma (a "candidate protein"). Candidate proteins are identified by a process comprising (i) identifying a protein in a first individual having the asthma phenotype; (ii) identifying a protein in a second individual not having the asthma phenotype; comparing the protein of the first individual to the protein of the second individual, wherein (a) the protein that is present in the second individual but not the first individual is the candidate protein or (b) the protein that is present in a higher amount in the second individual than in the first individual is the candidate protein or (c) the protein that is present in a lower amount in the second individual than in the first individual is the candidate protein.

This invention also includes nonhuman transgenic animals containing one or more of the nucleic acids of this invention for screening and other purposes. Further, knockout nonhuman transgenic animals can be produced wherein one or more endogenous genes or portions of such genes corresponding to the nucleic acids of this invention are replaced by marker genes or are deleted.

BRIEF DESCRIPTION OF THE FIGURES

FIGS. 3A-3C depict the nucleotide (SEQ ID NO: 2) and amino acid sequence (SEQ ID NO: 3) of Gene 214a.

FIGS. 4A-4C depict the nucleotide (SEQ ID NO: 4) and amino acid sequence (SEQ ID NO: 5) of Gene 214b.

FIGS. 5A-5C depict the nucleotide (SEQ ID NO: 6) and amino acid sequence (SEQ ID NO: 7) of Gene 214c.

FIGS. 6A-6D depict the nucleotide (SEQ ID NO: 8) and amino acid sequence (SEQ ID NO: 9) of Gene 214d.

FIGS. 7A-7D depict the nucleotide (SEQ ID NO: 10) and amino acid sequence (SEQ ID NO: 11) of Gene 214e.

FIGS. 10A-10B depict the nucleic acid sequence of the exons of Gene 214: Exon A—SEQ ID NO: 38; Exon B—SEQ ID NO: 39; Exon C—SEQ ID NO: 40; Exon C.2—SEQ ID NO: 41; Exon E.1—SEQ ID NO: 42; Exon E.2—SEQ ID NO: 43; Exon E.3—SEQ ID NO: 44; Exon F—SEQ ID NO: 45.

DETAILED DESCRIPTION OF THE INVENTION

Figure 1:
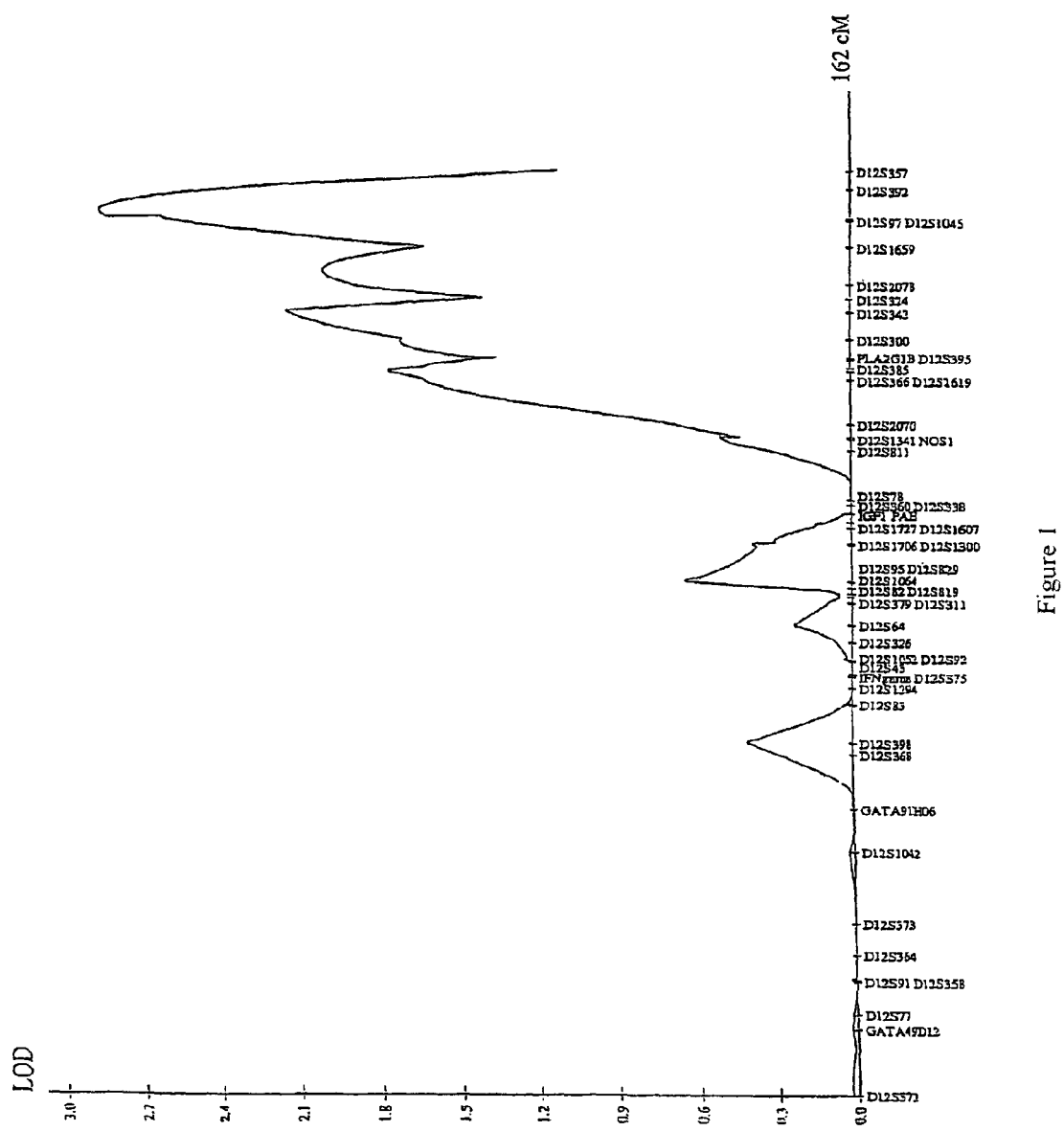
FIG. 1 shows the plot of multipoint LOD score against the map location of the markers along chromosome 12.

The present invention relates to Gene 214 nucleic acids comprising genomic DNA within BAC RP11-0702C13, the corresponding cDNA sequences, RNA, fragments of the genomic, cDNA, or RNA nucleic acids comprising 20, 40, 60, 100, 200, 500 or more contiguous nucleotides, and the complements thereof. Closely related variants are also included as part of this invention, as well as recombinant nucleic acids comprising at least 50, 60, 70, 80, or 90% of the nucleic acids described above which would be identical to a Gene 214 nucleic acids except for one or a few substitutions, deletions, or additions.

Further, the nucleic acids of this invention include the adjacent chromosomal regions of Gene 214 required for accurate expression of the respective gene. In a preferred embodiment, the present invention is directed to at least 15 contiguous nucleotides of the nucleic acid sequence of any of SEQ ID NO:2 (FIGS. 3A-3C), SEQ ID NO:4 (FIGS. 4A-4C), SEQ ID NO:6 (FIGS. 5A-5C), SEQ ID NO: 8 (FIGS. 6A-6D), and SEQ ID NO:10 (FIGS. 7A-7D). More particularly, embodiments of this invention include the BAC clone containing segments of Gene 214 including RP11-0702C13. A preferred embodiment is the nucleotide sequence of the BAC clones consisting of SEQ ID NO:1.

This invention further relates to methods using isolated and/or recombinant nucleic acids (DNA or RNA) that are characterized by their ability to hybridize to (a) a nucleic acid encoding a protein or polypeptide, such as a nucleic acid having any of the sequences of SEQ ID NO:2, SEQ ID NO:4, SEQ ID NO:6, SEQ ID NO: 8, and SEQ ID NO:10 or (b) a portion of the foregoing (e.g., a portion comprising the minimum nucleotides of the Gene 214 nucleic acid code a functional Gene 214 protein or the minimum number to inhibit an endogenous Gene 214; or by their ability to encode a polypeptide having the amino acid sequence of SEQ ID NO:3, SEQ ID NO:5, SEQ ID NO:7, SEQ ID NO: 9 and SEQ ID NO: 11 or to encode functional equivalents thereof; e.g., a polypeptide which when incorporated into a cell, has all or part of the activity of a Gene 214 protein, or by both characteristics. A functional equivalent of a Gene 214 protein, therefore, would have a similar amino acid sequence (at least 65% sequence identity) and similar characteristics to, or perform in substantially the same way as Gene 214 protein. A nucleic acid which hybridizes to a nucleic acid encoding a Gene 214 protein or polypeptide, such as SEQ ID NO:2, SEQ ID NO:4, SEQ ID NO:6, SEQ ID NO: 8, and SEQ ID NO:10 can be double- or single-stranded. Hybridization to DNA such as DNA having the sequence SEQ ID NO:2, SEQ ID NO:4, SEQ ID NO:6, SEQ ID NO: 8, and SEQ ID NO:10 includes hybridization to the strand shown or its complementary strand.

In one embodiment, the percent amino acid sequence similarity between a Gene 214 polypeptide such as SEQ ID NO:3, SEQ ID NO:5, SEQ ID NO:7, SEQ ID NO: 9 and SEQ ID NO: 11, and functional equivalents thereof is at least about 50%. In a preferred embodiment, the percent amino acid sequence similarity between such a Gene 214 polypeptide and its functional equivalents is at least about 65%. More preferably, the percent amino acid sequence similarity between a Gene 214 polypeptide and its functional equivalents is at least about 75%, and still more preferably, at least about 80%. To determine percent nucleotide or amino acid sequence similarity, sequences can be compared to publicly available sequence databases (National Center for Biotechnology Information, National Library of Medicine, 38A, 8N905, 8600 Rockville Pike, Bethesda, Md. 20894; www.ncbi.nlm.nih.gov) using the blastn2 algorithm (Altsch, *Nucl. Acids Res.*, 25:3389-3402 (1997)). The parameters for a typical search are: E=0.05, v=50, B=50 (where E is the expected probability score cutoff, V is the number of database entries returned in the reporting of the results, and B is the number of sequence alignments returned in the reporting of the results (Altsch et al, *J. Mol. Biol.*, 215:403-410 (1990)).

Isolated and/or recombinant nucleic acids meeting these criteria comprise nucleic acids having sequences identical to sequences of naturally occurring Gene 214 genes such as Gene 214a, Gene 214b, Gene 214c, Gene 214d, Gene 214e, and portions thereof, or variants of the naturally occurring genes. Such variants include mutants differing by the addition, deletion or substitution of one or more nucleotides, modified nucleic acids in which one or more nucleotides are modified (e.g., DNA or RNA analogs), and mutants comprising one or more modified nucleotides including repeated fragments.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1-2.10.16 (see particularly 2.10.8-11) and pages 6.3.1-6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures (1) employ low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) employ during hybridization 50% (vol/vol) formamide with 5×Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5×SSC at 42° C.; or (3) employ hybridization with 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

By varying hybridization conditions from a level of stringency at which no hybridization occurs to a level at which hybridization is first observed, conditions which will allow a given sequence to hybridize with the most similar sequences in the sample can be determined. Preferably the hybridizing sequences will have 60-70% sequence identity, more preferably 70-85% sequence identity, and even more preferably 90-100% sequence identity.

Exemplary conditions are described in Krause, M. H. and S. A. Aaronson (1991) *Methods in Enzymology*, 200:546-556. Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ~17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding a Gene 214 polypeptide, such as the nucleic acids depicted as SEQ ID NO:2, SEQ ID NO:4, SEQ ID NO:6, SEQ ID NO: 8, and SEQ ID NO:10, b) the complement, (c) or a portion of (a) or (b) (e.g. under high or moderate stringency conditions), may further encode a protein or polypeptide having at least one function characteristic of a Gene 214 polypeptide, such as protective barrier of the respiratory epithelium activity, or binding of antibodies that also bind to non-recombinant Gene 214 protein or polypeptide. The catalytic or binding function of a protein or polypeptide encoded by the hybridizing nucleic acid may be detected by standard enzymatic assays for activity or binding (e.g., assays which measure the binding of a transit peptide or a precursor, or other components of the translocation machinery). Enzymatic assays, complementation tests, or other suitable methods can also be used in procedures for the identification and/or isolation of nucleic acids which encode a polypeptide such as a polypeptide of the amino acid sequences SEQ ID NO:3, SEQ ID NO:5, SEQ ID NO:7, SEQ ID NO: 9 and SEQ ID NO: 11, or a functional equivalent of these polypeptides. The antigenic properties of proteins or polypeptides encoded by hybridizing nucleic acids can be determined by immunological methods employing antibodies that bind to a Gene 214 polypeptide such as immunoblot, immunoprecipitation and radioimmunoassay. PCR methodology, including RAGE (Rapid Amplification of Genomic DNA Ends), can also be used to screen for and detect the presence of nucleic acids which encode Gene 214-like proteins and polypeptides, and to assist in cloning such nucleic acids from genomic DNA. PCR methods for these purposes can be found in Innis, M. A., et al. (1990) *PCR Protocols: A Guide to Methods and Applications*, Academic Press, Inc., San Diego, Calif., incorporated herein by reference.

It is understood that, as a result of the degeneracy of the genetic code, many nucleic acid sequences are possible which encode a Gene 214-like protein or polypeptide. Some of these will have little homology to the nucleotide sequences of any known or naturally-occurring Gene 214-like gene but can be used to produce the proteins and polypeptides of this invention by selection of combinations of nucleotide triplets based on codon choices. Such variants, while not hybridizable to a naturally-occurring Gene 214 gene, are contemplated within this invention.

The nucleic acids described herein are used in the methods of the present invention for production of proteins or polypeptides, through incorporation into cells, tissues, or organisms. In one embodiment, DNA containing all or part of the coding sequence for a Gene 214 polypeptide, or DNA which hybridizes to DNA having the sequence SEQ ID NO:2, SEQ ID NO:4, SEQ ID NO:6, SEQ ID NO: 8, and SEQ ID NO:10, is incorporated into a vector for expression of the encoded polypeptide in suitable host cells. The encoded polypeptide consisting of Gene 214, or its functional equivalent is capable of normal activity, such as protecting the respiratory epithelium. The term "vector" as used herein refers to a nucleic acid molecule capable of replicating another nucleic acid to which it has been linked. A vector, for example, can be a plasmid.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated", as used herein, refers to nucleic or amino acid sequences that are at least 60% free, preferably 75% free, and most preferably 90% free from other components with which they are naturally associated. "Isolated" nucleic acids (polynucleotides) include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial replication, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewmaker, et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO:2, SEQ ID NO:4, SEQ ID NO:6, SEQ ID NO: 8, and SEQ ID NO:10. For example, an antisense nucleic acid or oligonucleotide can be complementary to a target nucleic acid having the sequence shown as the strand of the open reading frame of SEQ ID NO:2, SEQ ID NO:4, SEQ ID NO:6, SEQ ID NO: 8, and SEQ ID NO:10 or nucleic acid encoding a functional equivalent of Gene 214, or to a portion of these nucleic acids sufficient to allow hybridization. A portion, for example a sequence of 16 nucleotides, could be sufficient to inhibit expression of the protein. Or, an antisense nucleic acid or oligonucleotide, complementary to 5' or 3' untranslated regions, or overlapping the translation initiation codon (5' untranslated and translated regions), of the Gene 214 gene, or a gene encoding a functional equivalent can also be effective. In another embodiment, the antisense nucleic acid is wholly or partially complementary to and can hybridize with a target nucleic acid which encodes a Gene 214 polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding Gene 214, or its functional equivalent (Frank-Kamenetskii, M.D. and Mirkin, S. M. (1995) *Ann. Rev. Biochem.* 64:65-95.) Such oligonucleotides of the invention are constructed using the base-pairing rules of triple helix formation and the nucleotide sequence of the gene or mRNA for Gene 214. These oligonucleotides can block Gene 214-type activity in a number of ways, including prevention of transcription of the Gene 214 gene or by binding to mRNA as it is transcribed by the gene.

The invention also relates to proteins or polypeptides encoded by the novel nucleic acids described herein. The proteins and polypeptides of this invention can be isolated and/or recombinant. Proteins or polypeptides referred to herein as "isolated" are proteins or polypeptides purified to a state beyond that in which they exist in cells. In a preferred embodiment, they are at least 10% pure; i.e., most preferably they are substantially purified to 80 or 90% purity. "Isolated" proteins or polypeptides include proteins or polypeptides obtained by methods described infra, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of a Gene 214 protein or polypeptide, for example, protective barrier to the respiratory epithelium activity in the case of Gene 214 analogs, and/or antigenic function (e.g., binding of antibodies that also bind to naturally occurring Gene 214 polypeptide). As such, these proteins are referred to as analogs, and include, for example, naturally occurring Gene 214, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues. The variant can have "conservative" changes, wherein a substituted amino acid has similar structural or chemical properties, e.g., replacement of leucine with isoleucine. More infrequently, a variant can have "nonconservative" changes, e.g., replacement of a glycine with a tryptophan. Guidance in determining which amino acid residues can be substituted, inserted, or deleted without abolishing biological or immunological activity can be found using computer programs well known in the art, for example, DNASTAR software (DNASTAR, Inc., Madison, Wis. 53715 U.S.A.).

A "portion" as used herein with regard to a protein or polypeptide, refers to fragments of that protein or polypeptide. The fragments can range in size from 5 amino acid residues to all but one residue of the entire protein sequence. Thus, a portion or fragment can be at least 5, 5-50, 50-100, 100-200, 200-400, 400-800, or more consecutive amino acid residues of a Gene 214 protein or polypeptide, for example, SEQ ID NO:3, SEQ ID NO:5, SEQ ID NO:7, SEQ ID NO: 9 and SEQ ID NO: 11, or a variant thereof.

The invention also relates to isolated, synthesized and/or recombinant portions or fragments of a Gene 214 protein or polypeptide as described above. Polypeptide fragments of the enzyme can be made which have full or partial function on their own, or which when mixed together (though fully, partially, or nonfunctional alone), spontaneously assemble with one or more other polypeptides to reconstitute a functional protein having at least one functional characteristic of a Gene 214 proteinof this invention.

The invention also concerns the use of the nucleotide sequence of the nucleic acids of this invention to identify DNA probes for Gene 214 genes, PCR primers to amplify Gene 214 genes, nucleotide polymorphisms in Gene 214 genes, and regulatory elements of the Gene 214 genes.

Gene 214 was isolated by narrowly defining the region of chromosome 12q23-qter 12q23-qter which was associated with airway hyperresponsiveness and asthma. Gene 214 is also important in other diseases such as obesity and thus, there was a need to identify and isolate the gene.

To aid in the understanding of the specification and claims, the following definitions are provided.

"Disorder region" refers to a portion of the human chromosome 12 bounded by the markers D12S2070 to the 12q telomere. A "disorder-associated" nucleic acid or "disorder-associated" polypeptide sequence refers to a nucleic acid sequence that maps to region 12q23-qter and polypeptides encoded therein. For nucleic acid sequences, this encompasses sequences that are homologous or complementary to the sequence, as well as "sequence-conservative variants" and "function-conservative variants." For polypeptide sequences, this encompasses "function-conservative variants." Included are naturally-occurring mutations causative of respiratory diseases or obesity, such as but not limited to mutations which cause inappropriate expression (e.g., lack of expression, over-expression, expression in an inappropriate tissue type). "Sequence-conservative" variants are those in which a change of one or more nucleotides in a given codon position results in no alteration in the amino acid encoded at that position. "Function-conservative" variants are those in which a change in one or more nucleotides in a given codon position results in a polypeptide sequence in which a given amino acid residue in a polypeptide has been changed without substantially altering the overall conformation and function of the native polypeptide, including, but not limited to, replacement of an amino acid with one having similar physico-chemical properties (such as, for example, acidic, basic, hydrophobic, and the like). "Function-conservative" variants also include analogs of a given polypeptide and any polypeptides that have the ability to elicit antibodies specific to a designated polypeptide.

"Nucleic acid or "polynucleotide" as used herein refers to purine- and pyrimidine-containing polymers of any length, either polyribonucleotides or polydeoxyribonucleotide or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" of a nucleic acid sequence as used herein refers to the "antisense" sequence that participates in Watson-Crick base-pairing with the original sequence.

A "probe" refers to a nucleic acid or oligonucleotide that forms a hybrid structure with a sequence in a target region due to complementarily of at least one sequence in the probe with a sequence in the target region.

Nucleic acids are "hybridizable" to each other when at least one strand of nucleic acid can anneal to another nucleic acid strand under defined stringency conditions. As is well known in the art, stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarily, variables well known in the art.

An "immunogenic component", is a moiety that is capable of eliciting a humoral and/or cellular immune response in a host animal.

An "antigenic component" is a moiety that binds to its specific antibody with sufficiently high affinity to form a detectable antigen-antibody complex.

A "sample" as used herein refers to a biological sample, such as, for example, tissue or fluid isolated from an individual (including without limitation plasma, serum, cerebrospinal fluid, lymph, tears, saliva, milk, pus, and tissue exudates and secretions) or from in vitro cell culture constituents, as well as samples obtained from e.g., a laboratory procedure.

"Gene" refers to a DNA sequence that encodes through its template or messenger RNA a sequence of amino acids characteristic of a specific peptide, polypeptide or protein. The term "gene" as used herein with reference to genomic DNA includes intervening, non-coding regions, as well as regulatory regions, and can include 5' and 3' ends.

"Gene sequence" refers to a DNA molecule, including both a DNA molecule which contains a non-transcribed or non-translated sequence. The term is also intended to include any combination of gene(s), gene fragment(s), non-transcribed sequence(s) or non-translated sequence(s) which are present on the same DNA molecule.

A gene sequence is "wild-type" if such sequence is usually found in individuals unaffected by the disease or condition of interest. However, environmental factors and other genes can also play an important role in the ultimate determination of the disease. In the context of complex diseases involving multiple genes ("oligogenic disease"), the "wild type" or normal sequence can also be associated with a measurable risk or susceptibility, receiving its reference status based on its frequency in the general population.

A gene sequence is a "mutant" sequence if it differs from the wild-type sequence. In some cases, the individual carrying such gene has increased susceptibility toward the disease or condition of interest. In other cases, the "mutant" sequence might also refer to a sequence that decreases the susceptibilty toward a disease or condition of interest, and thus acting in a protective manner. Also a gene is a "mutant" gene if too much ("overexpressed") or too little ("underexpressed") of such gene is expressed in the tissues in which such gene is normally expressed, thereby causing the disease or condition of interest.

A gene sequence is a "variant" sequence if it is substantially similar in structure to either the entire gene or to a fragment of the gene. Both wild-type genes and mutant genes have variant sequences.

The sequences of the present invention may be derived from a variety of sources including DNA, cDNA, synthetic DNA, synthetic RNA or combinations thereof. Such sequences may comprise genomic DNA which may or may not include naturally occurring introns. Moreover, such genomic DNA may be obtained in association with promoter regions or poly (A) sequences. The sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

"cDNA" refers to complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector or PCR amplified. This term includes genes from which the intervening sequences have been removed.

"Recombinant DNA" means a molecule that has been recombined by in vitro splicing/and includes cDNA or a genomic DNA sequence.

"Cloning" refers to the use of in vitro recombination techniques to insert a particular gene or other DNA sequence into a vector molecule. In order to successfully clone a desired gene, it is necessary to use methods for generating DNA fragments, for joining the fragments to vector molecules, for introducing the composite DNA molecule into a host cell in which it can replicate, and for selecting the clone having the target gene from amongst the recipient host cells.

"cDNA library" refers to a collection of recombinant DNA molecules containing cDNA inserts which together comprise the entire genome of an organism. Such a cDNA library can be prepared by methods known to one skilled in the art and described by, for example, Cowell and Austin, "cDNA Library Protocols," Methods in Molecular Biology (1997). Generally, RNA is first isolated from the cells of an organism from whose genome it is desired to clone a particular gene.

"Cloning vehicle" refers to a plasmid or phage DNA or other DNA sequence which is able to replicate in a host cell.

The cloning vehicle is characterized by one or more endonuclease recognition sites at which such DNA sequences may be cut in a determinable fashion without loss of an essential biological function of the DNA, which may contain a marker suitable for use in the identification of transformed cells.

"Expression control sequence" refers to a sequence of nucleotides that control or regulate expression of structural genes when operably linked to those genes. These include, for example, the lac systems, the trp system, major operator and promoter regions of the phage lambda, the control region of fd coat protein and other sequences known to control the expression of genes in prokaryotic or eukaryotic cells. Expression control sequences will vary depending on whether the vector is designed to express the operably linked gene in a prokaryotic or eukaryotic host, and may contain transcriptional elements such as enhancer elements, termination sequences, tissue-specificity elements and/or translational initiation and termination sites.

"Expression vehicle" refers to a vehicle or vector similar to a cloning vehicle but which is capable of expressing a gene which has been cloned into it, after transformation into a host. The cloned gene is usually placed under the control of (i.e., operably linked to) an expression control sequence.

"Operably linked" means that the promoter controls the initiation of expression of the gene. A promoter is operably linked to a sequence of proximal DNA if upon introduction into a host cell the promoter determines the transcription of the proximal DNA sequence(s) into one or more species of RNA. A promoter is operably linked to a DNA sequence if the promoter is capable of initiating transcription of that DNA sequence.

"Host" includes prokaryotes and eukaryotes. The term includes an organism or cell that is the recipient of a replicable expression vehicle.

"Amplification of nucleic acids" refers to methods such as polymerase chain reaction (PCR), ligation amplification (or ligase chain reaction, LCR) and amplification methods based on the use of Q-beta replicase. These methods are well known in the art and described, for example, in U.S. Pat. Nos. 4,683,195 and 4,683,202. Reagents and hardware for conducting PCR are commercially available. Primers useful for amplifying sequences from the disorder region are preferably complementary to, and preferably hybridize specifically to, sequences in the 12q23-qter region or in regions that flank a target region therein. Gene 214 generated by amplification may be sequenced directly. Alternatively, the amplified sequence(s) may be cloned prior to sequence analysis.

"Antibodies" refer to polyclonal and/or monoclonal antibodies and fragments thereof, and immunologic binding equivalents thereof, that can bind to asthma proteins and fragments thereof or to nucleic acid sequences from the 12q23-qter region, particularly from the asthma locus or a portion thereof. The term antibody is used both to refer to a homogeneous molecular entity, or a mixture such as a serum product made up of a plurality of different molecular entities. Proteins may be prepared synthetically in a protein synthesizer and coupled to a carrier molecule and injected over several months into rabbits. Rabbit sera is tested for immunoreactivity to the protein or fragment. Monoclonal antibodies may be made by injecting mice with the proteins, or fragments thereof. Monoclonal antibodies will be screened by ELISA and tested for specific immunoreactivity with protein or fragments thereof (Harlow et al, *Antibodies: A Laboratory Manual*, Cold Spring Harbor Laboratory, Cold Spring Harbor, N.Y. (1988.) These antibodies will be useful assays as well as pharmaceuticals.

A nucleic acid or fragment thereof is "substantially homologous" or "substantially similar" to another if, when optimally aligned (with appropriate nucleotide insertions and/or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or similarity exists when a nucleic acid or fragment thereof will hybridize, under selective hybridization conditions, to another nucleic acid (or a complementary strand thereof). Selectivity of hybridization exists when hybridization which is substantially more selective than total lack of specificity occurs. Typically, selective hybridization will occur when there is at least about 55% homology over a stretch of at least about nine or more nucleotides, preferably at least about 65%, more preferably at least about 75%, and most preferably at least about 90%. (See, M. Kanehisa, 1984, Nucleic Acids Res., 12(1 Pt 1):203-13; M. Kanehisa et al., 1984, Nucleic Acids Res., 12(1 Pt 1):149-58; M. Kanehisa et al., 1984, Nucleic Acids Res. 12(1 Pt 1):417-28). The length of homology comparison, as described, may be over longer stretches, and in certain embodiments will often be over a stretch of at least about 14 nucleotides, usually at least about 20 nucleotides, more usually at least about 24 nucleotides, typically at least about 28 nucleotides, more typically at least about 32 nucleotides, and preferably at least about 36 or more nucleotides.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., Molecular Cloning: A Laboratory Manual, 2d Ed., Cold Spring Harbor Laboratory Press, Planview, New York (1989); Kaufman, P. B., et al., Eds., Handbook of Molecular and Cellular Methods in Biology and Medicine, CRC Press, Boca Raton (1995); McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991); DNA Cloning, Volumes I and II (D. N Glover ed. 1985); Oligonucleotide Synthesis (M. J. Gait ed, 1984); Nucleic Acid Hybridization (B. D. Hames & S. J. Higgins eds. 1984); the series, Methods in Enzymology (Academic Press, Inc.), particularly Vol. 154 and Vol. 155 (Wu and Grossman, eds.); PCR-A Practical Approach (McPherson, Quirke, and Taylor, eds., 1991); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; Gene Transfer Vectors for Mammalian Cells, 1987 (J. H. Miller and M. P. Calos eds., Cold Spring Harbor Laboratory); Martin J. Bishop, ed., Guide to Human Genome Computing, 2d Edition, Academic Press, San Diego, Calif. (1998); and Leonard F. Peruski, Jr., and Anne Harwood Peruski, The Internet and the New Biology: Tools for Genomic and Molecular Research, American Society for Microbiology, Washington, D.C. (1997). Standard reference works setting forth the general principles of immunology include Sell, S., Immunology, Immunopathology & Immunity, 5th Ed., Appleton & Lange, Publ., Stamford, Conn. (1996); Male, D., et al., Advanced Immunology, 3d Ed., Times Mirror Int'l Publishers Ltd., Publ., London (1996); Stites, D. P., and Terr, A. I., Basic and Clinical Immunology, 7th Ed., Appleton & Lange, Publ., Norwalk, Conn. (1991); and Abbas, A. K., et al., Cellular and Molecular Immunology, W. B. Saunders Co., Publ., Philadelphia, Pa. (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

The nucleic acids of the invention may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The invention also provides vectors comprising the disorder-associated sequences or derivatives or fragments thereof and host cells for the production of purified proteins. A large number of vectors, including plasmid and fungal vectors, have been described for replication and/or expression in a variety of eukaryotic and prokaryotic hosts, and may be used for gene therapy as well as for simple cloning or protein expression.

Using the information provided in SEQ ID NO:2, SEQ ID NO:4, SEQ ID NO:6, SEQ ID NO: 8, and SEQ ID NO:10, one skilled in the art will be able to clone and sequence all representative nucleic acids of interest, including nucleic acids encoding complete protein-coding sequences. It is to be understood that non-protein-coding sequences contained within SEQ ID NO:2, SEQ ID NO:4, SEQ ID NO:6, SEQ ID NO: 8, and SEQ ID NO:10 and the genomic sequence of SEQ ID NO:1 are also within the scope of the invention. Such sequences include, without limitation, sequences important for replication, recombination, transcription and translation. Non-limiting examples include promoters and regulatory binding sites involved in regulation of gene expression, and 5'- and 3'-untranslated sequences (e.g., ribosome-binding sites) that form part of mRNA molecules.

The nucleic acids of the present invention find use as primers and templates for the recombinant production of disorder-associated peptides or polypeptides, for chromosome and gene mapping, to provide antisense sequences, for tissue distribution studies, to locate and obtain full length genes, to identify and obtain homologous sequences (wild-type and mutants), and in diagnostic applications.

Polypeptides according to the invention are at least five or more residues in length. Preferably, the polypeptides comprise at least about 12, more preferably at least about 20 and most preferably at least about 30 such residues. Nucleic acids comprising protein-coding sequences can be used to direct the expression of asthma-associated polypeptides in intact cells or in cell-free translation systems. The known genetic code, tailored if desired for more efficient expression in a given host organism, can be used to synthesize oligonucleotides encoding the desired amino acid sequences. The resulting oligonucleotides can be inserted into an appropriate vector and expressed in a compatible host organism.

The polypeptides of the present invention, including function-conservative variants, may be isolated from wild-type or mutant cells, or from heterologous organisms or cells (e.g., bacteria, fungi, yeast, insect, plant, and mammalian cells) in which a disorder-associated protein-coding sequence has been introduced and expressed. Furthermore, the polypeptides may be part of recombinant fusion proteins. The polypeptides can also, advantageously, be made using cell-free protein synthesis systems or by synthetic chemistry. Polypeptides may be chemically synthesized by commercially available automated procedures, including, without limitation, exclusive solid phase synthesis, partial solid phase methods, fragment condensation or classical solution synthesis.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the disorder-associated protein contains an additional sequence tag that facilitates purification. Alternatively, antibodies produced against an disorder-associated protein or against peptides derived therefrom can be used as purification reagents. Other purification methods are possible.

The present invention also encompasses derivatives and homologies of disorder-associated polypeptides. For some purposes, nucleic acid sequences encoding the peptides may be altered by substitutions, additions, or deletions that provide for functionally equivalent molecules, i.e., function-conservative variants. The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Both the naturally occurring and recombinant forms of the polypeptides of the invention can advantageously be used to screen compounds for binding activity. Many methods of screening for binding activity are known by those skilled in the art and may be used to practice the invention. Several methods of automated assays have been developed in recent years so as to permit screening of tens of thousands of compounds in a short period of time. Such high-throughput screening methods are particularly preferred. The use of high-throughput screening assays to test for inhibitors is greatly facilitated by the availability of large amounts of purified polypeptides, as provided by the invention. The polypeptides of the invention also find use as therapeutic agents as well as antigenic components to prepare antibodies.

The polypeptides of this invention find use as immunogenic components useful as antigens for preparing antibodies by standard methods. It is well known in the art that immunogenic epitopes generally contain at least about five amino acid residues, Ohno et al., 1985, *Proc. Natl. Acad. Sci. USA* 82:2945. Therefore, the immunogenic components of this invention will typically comprise at least five amino acid residues of the sequence of the complete polypeptide chains. Preferably, they will contain at least 7, and most preferably at least about 10 amino acid residues or more to ensure that they will be immunogenic. Whether a given component is immunogenic can readily be determined by routine experimentation Such immunogenic components can be produced by proteolytic cleavage of larger polypeptides or by chemical synthesis or recombinant technology and are thus not limited by proteolytic cleavage sites. The present invention thus encompasses antibodies that specifically recognize asthma-associated immunogenic components.

Antibodies according to the present invention include polyclonal and monoclonal antibodies. The antibodies may be elicited in an animal host by immunization with disorder-associated immunogenic components or may be formed by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including $Fab^1$ and $Fab(ab)^2$ fragments of antibodies.

These antibodies, whether polyclonal or monoclonal, can be used, e.g., in an immobilized form bound to a solid support by well known methods, to purify the immunogenic components and disorder-associated polypeptides by immunoaffinity chromatography. Antibodies against the immunogenic components can also be used, unlabeled or labeled by standard methods, as the basis for immunoassays, i.e., as diagnostic reagents.

Hybridomas of the invention used to make monoclonal antibodies against the immunogenic components of the invention are produced by well-known techniques. Usually, the process involves the fusion of an immortalizing cell line with a B-lymphocyte that produces the desired antibody. Alternatively, non-fusion techniques for generating immortal antibody-producing cell lines are possible, and come within the purview of the present invention, e.g., virally-induced transformation, Casali et al., 1986, *Science* 234:476. Immortalizing cell lines are usually transformed mammalian cells, particularly myeloma cells of rodent, bovine, and human origin. Most frequently, rat or mouse myeloma cell lines are employed as a matter of convenience and availability.

Hybridomas are selected by standard procedures, such as HAT (hypoxanthine-aminopterin-thymidine) selection. From among these hybridomas, those secreting the desired antibody are selected by assaying their culture medium by standard immunoassays, such as Western blotting, ELISA (enzyme-linked immunosorbent assay), RIA (radioimmunoassay), or the like. Antibodies are recovered from the medium using standard protein purification techniques, Tijssen, 1985, *Practice and Theory of Enzyme Immunoassays*, Elsevier, Amsterdam.

I. Localization of an Asthma Locus on Chromosome 12q23-qter and the Characterization of a Candidate Gene within the Region To identify genes in the region on 12q23-qter, a set of bacterial artificial chromosome (BAC) clones containing this chromosomal region was identified. The BAC clones served as a template for genomic DNA sequencing and serve as reagents for identifying coding sequences by direct cDNA selection. Genomic sequencing and direct cDNA selection were used to characterize DNA from 12q23-qter.

When a gene has been genetically localized to a specific chromosomal region, the genes in this region can be characterized at the molecular level by a series of steps that include: cloning of the entire region of DNA in a set of overlapping clones (physical mapping), characterization of genes encoded by these clones by a combination of direct cDNA selection, exon trapping and DNA sequencing (gene identification), and identification of mutations in these genes by comparative DNA sequencing of affected and unaffected members of the kindred and/or in unrelated affected individuals and unrelated unaffected controls (mutation analysis).

Physical mapping is accomplished by screening libraries of human DNA cloned in vectors that are propagated in a host such as *E. coli*, using hybridization or PCR assays from unique molecular landmarks in the chromosomal region of interest. To generate a physical map of the disorder region, a library of human DNA cloned in BACs was screened with a set of overgo markers that had been previously mapped to chromosome 12q23-qter by the efforts of the Human Genome Project. Overgos are unique molecular landmarks in the human genome that can be assayed by hybridization. Through the combined efforts of the Human Genome Project, the location of thousands of overgos on the twenty-two autosomes and two sex chromosomes has been determined. For a positional cloning effort, the physical map is tied to the genetic map because the markers used for genetic mapping can also be used as overgos for physical mapping. By screening a BAC library with a combination of overgos derived from genetic markers, genes, and random DNA fragments, a physical map comprised of overlapping clones representing all of the DNA in a chromosomal region of interest can be assembled.

BACs are cloning vectors for large (80 kilobase to 200 kilobase) segments of human or other DNA that are propagated in *E. coli*. To construct a physical map using BACs, a library of BAC clones is screened so that individual clones harboring the DNA sequence corresponding to a given overgo or set of overgos are identified. Throughout most of the human genome, the overgo markers are spaced approximately 20 to 50 kilobases apart, so that an individual BAC clone typically contains at least two overgo markers. In addition, the BAC libraries that were screened contain enough cloned DNA to cover the human genome twelve times over. Therefore, an individual overgo typically identifies more than one BAC clone. By screening a twelve-fold coverage BAC library with a series of overgo markers spaced approximately 50 kilobases apart, a physical map consisting of a series of overlapping contiguous BAC clones, i.e., BAC "contigs," can be assembled for any region of the human genome. This map is closely tied to the genetic map because many of the overgo markers used to prepare the physical map are also genetic markers.

When constructing a physical map, it often happens that there are gaps in the overgo map of the genome that result in the inability to identify BAC clones that are overlapping in a given location. Typically, the physical map is first constructed from a set of overgos identified through the publicly available literature and World Wide Web resources. The initial map consists of several separate BAC contigs that are separated by gaps of unknown molecular distance. To identify BAC clones that fill these gaps, it is necessary to develop new overgo markers from the ends of the clones on either side of the gap. This is done by sequencing the terminal 200 to 300 base pairs of the BACs flanking the gap, and developing a PCR or hybridization based assay. If the terminal sequences are demonstrated to be unique within the human genome, then the new overgo can be used to screen the BAC library to identify additional BACs that contain the DNA from the gap in the physical map. To assemble a BAC contig that covers a region the size of the disorder region (6,000,000 or more base pairs), it is necessary to develop new overgo markers from the ends of a number of clones.

After building a BAC contig, this set of overlapping clones serves as a template for identifying the genes encoded in the chromosomal region. Gene identification can be accomplished by many methods. Three methods are commonly used: (1) a set of BACs selected from the BAC contig to represent the entire chromosomal region can be sequenced, and computational methods can be used to identify all of the genes, (2) the BACs from the BAC contig can be used as a reagent to clone cDNAs corresponding to the genes encoded in the region by a method termed direct cDNA selection, or (3) the BACs from the BAC contig can be used to identify coding sequences by selecting for specific DNA sequence motifs in a procedure called exon trapping. The present invention includes Gene 214 identified by the first two methods.

To sequence the entire BAC contig representing the disorder region, a set of BACs can be chosen for subcloning into plasmid vectors and subsequent DNA sequencing of these subclones. Since the DNA cloned in the BACs represents genomic DNA, this sequencing is referred to as genomic sequencing to distinguish it from cDNA sequencing. To initiate the genomic sequencing for a chromosomal region of interest, several non-overlapping BAC clones are chosen. DNA for each BAC clone is prepared, and the clones are sheared into random small fragments which are subsequently cloned into standard plasmid vectors such as pUC18. The plasmid clones are then grown to propagate the smaller fragments, and these are the templates for sequencing. To ensure adequate coverage and sequence quality for the BAC DNA sequence, sufficient plasmid clones are sequenced to yield three-fold coverage of the BAC clone. For example, if the BAC is 100 kilobases long, then phagemids are sequenced to yield 300 kilobases of sequence. Since the BAC DNA was randomly sheared prior to cloning in the phagemid vector, the 300 kilobases of raw DNA sequence can be assembled by computational methods into overlapping DNA sequences termed sequence contigs. For the purposes of initial gene identification by computational methods, three-fold coverage of each BAC is sufficient to yield twenty to forty sequence contigs of 1000 base pairs to 20,000 base pairs.

The sequencing strategy employed in this invention was to initially sequence "seed" BACs from the BAC contig in the disorder region. The sequence of the "seed" BACs was then used to identify minimally overlapping BACs from the contig, and these were subsequently sequenced. In this manner, the entire candidate region can be sequenced, with several small sequence gaps left in each BAC. This sequence serves as the template for computational gene identification. One method for computational gene identification is to compare the sequence of BAC contig to publicly available databases of cDNA and genomic sequences, e.g. unigene, dbEST, genbank. These comparisons are typically done using the BLAST family of computer algorithms and programs (Altschul et al, *J. Mol. Biol.*, 215:403-410 (1990)). The BAC sequence can also be translated into protein sequence, and the protein sequence can be used to search publicly available protein databases, using a version of BLAST designed to analyze protein sequences (Altshul et al, *Nucl. Acids Res.*, 25:3389-3402 (1997)). Another method is to use computer algorithms such as MZEF (Zhang, *Proc. Natl. Acad. Sci.*, 94:565-568 (1997)), GRAIL (Uberbacher et al, *Methods Enzymol.*, 266:259-281 (1996)), and Genscan (Burge and Karlin, *J. Mol. Biol.*, 268:78-94) which predicts the location of exons in the sequence based on the presence of specific DNA sequence motifs that are common to all exons, as well as the presence of codon usage typical of human protein encoding sequences.

In addition to identifying genes by computational methods, genes were also identified by direct cDNA selection (Del Mastro and Lovett, *Methods in Molecular Biology*, Humana Press Inc., NJ (1996)). In direct cDNA selection, cDNA pools from tissues of interest are prepared, and BACs from the candidate region are used in a liquid hybridization assay to capture the cDNAs which base pair to coding regions in the BAC. In the methods described herein, the cDNA pools were created from several different tissues by random priming and oligo dT priming the first strand cDNA from polyA RNA, synthesizing the second strand cDNA by standard methods, and adding linkers to the ends of the cDNA fragments. The linkers are used to amplify the cDNA pools. BAC clones from the disorder region identified by screening the RPCI-11 BAC library (P. deJong, Russell Park Cancer Institute) were used as a template for initiating DNA synthesis to create a biotin labeled copy of BAC DNA. The biotin labelled copy of the BAC DNA is then denatured and incubated with an excess of the PCR amplified, linkered cDNA pools which have also been denatured. The BAC DNA and cDNA are allowed to anneal in solution, and heteroduplexes between the BAC and the cDNA are isolated using streptavidin coated magnetic beads. The cDNAs that are captured by the BAC are then amplified using primers complimentary to the linker sequences, and the hybridization/selection process is repeated for a second round. After two rounds of direct cDNA selection, the cDNA fragments are cloned, and a library of these direct selected fragments is created.

The cDNA clones isolated by direct selection are analyzed by two methods. Since a pool of BACs from the disorder region is used to provide the genomic target DNA sequence, the cDNAs must be mapped to BAC genomic clones to verify their chromosomal location. This is accomplished by arraying the cDNAs in microtiter dishes, and replicating their DNA in high density grids. Individual genomic clones known to map to the region are then hybridized to the grid to identify direct selected cDNAs mapping to that region. cDNA clones that are confirmed to correspond to individual BACs are sequenced. To determine whether the cDNA clones isolated by direct selection share sequence identity or similarity to previously identified genes, the DNA and protein coding sequences are compared to publicly available databases using the BLAST family of programs.

The combination of genomic DNA sequence and cDNA sequence provided by BAC sequencing and by direct cDNA selection yields an initial list of putative genes in the region. The genes in the region were all candidates for the asthma locus. To further characterize each gene, Northern blots were performed to determine the size of the transcript corresponding to each gene, and to determine which putative exons were transcribed together to make an individual gene. For Northern blot analysis of each gene, probes were prepared from direct selected cDNA clones or by PCR amplifying specific fragments from genomic DNA, cDNA or from the BAC encoding the putative gene of interest. The Northern blots gave information on the size of the transcript and the tissues in which it was expressed. For transcripts which were not highly expressed, it was sometimes necessary to perform a reverse transcription PCR assay using RNA from the tissues of interest as a template for the reaction.

Gene identification by computational methods and by direct cDNA selection provides unique information about the genes in a region of a chromosome. When genes are identified, then it is possible to examine different individuals for mutations in each gene. Variants in gene sequences between individuals can be inherited allelic differences or can arise from mutations in the individuals. Gene sequence variants are clinically important in that they can affect drug action on such gene. Most drugs elicit a safe response in only a fraction of individuals, and drugs are commonly administered to patients with no certainty that they will be safe and effective. Many important drugs are effective in only 30-40% of patients for whom the drug is prescribed, and virtually all drugs cause adverse events in some individuals. Identification of mutations in disorder genes in different individuals will enable a correlation between the safety and efficacy of drug therapies used to treat lung diseases and the genotypes of the treated individuals. This correlation enables health care providers to prescribe a drug regimen which is most appropriate for the individual patient rather than trying different drug regimens in turn until a successful drug is identified. Identification of variants in disorder genes will also have a benefit during the development of new drugs for the treatment of lung diseases, as the ability to correlate genetic variation with the efficacy of new candidate drugs will enhance lead optimization and increase the efficiency and success rate of new drug approvals.

A. Family Collection

A critical component of any disease gene search is the careful selection and phenotyping of family resources. The family collection utilized in this study consists of 421 Caucasian affected sibling ("sib") pairs families collected in the United States and the United Kingdom, as well as an additional 63 Caucasian families from the United Kingdom collected under different ascertainment criteria.

The affected sibling (or "sib") pair families in the United States collection were Caucasian families with two affected siblings that were identified through both private practice and community physicians. Advertising was also used to identify candidates. A total of 98 families were collected in Kansas, Nebraska, and Southern California. In the United Kingdom collection, 323 families were identified through physicians' registers in a region surrounding Southampton and including the Isle of Wight.

Families were included in the study if they met all of the following criteria: (1) the biological mother and biological father were Caucasian and agreed to participate in the study, (2) at least two biological siblings were alive, each with a current physician diagnosis of asthma, and 5 to 21 years of age, and (3) the two siblings were currently taking asthma medications on a regular basis. This included regular, intermittent use of inhaled or oral bronchodilators and regular use of cromolyn, theophylline, or steroids.

Families were excluded from the study if they met any one of the following criteria: (1) both parents were affected (i.e., with a current diagnosis of asthma, having asthma symptoms, or on asthma medications at the time of the study), or (2) any of the siblings to be included in the study was less than 5 years of age, or (3) any asthmatic family member to be included in the study was taking beta-blockers at the time of the study or (4) any family member had congenital or acquired pulmonary disease at birth (e.g. cystic fibrosis) history of serious cardiac disease (myocardial infarction) or any history of serious pulmonary disease (e.g. emphysema) or (5) pregnant.

An additional 63 families from the United Kingdom were utilized from an earlier collection effort with different ascertainment criteria. These families were recruited either: 1) without reference to asthma and atopy or 2) by having at least one family member or at least two family members affected with asthma. The randomly ascertained samples were identified from general practitioner registers in the Southampton area. For the families with affected members, the probands were recruited from hospital based clinics in Southampton. The phenotypic and genotypic data information for 17 markers for 21 of these 63 families was obtained from the website: http://cedar.genetics.soton.ac.uk/pub/PROGRAMS/BETA/data/bet12.ped.

B. Genome Scan

In order to identify chromosomal regions linked to asthma, the inheritance pattern of alleles from genetic markers spanning the genome was assessed on the collected family resources. As described above, combining these results with the segregation of the asthma phenotype in these families allows the identification of genetic markers that are tightly linked to asthma, thus providing an indication of the location of genes predisposing affected individuals to asthma. The following discussion describes the protocol used to assess the genotypes of the collected population using genetic markers spanning the entire genome.

Genotypes of PCR amplified simple sequence microsatellite genetic linkage markers were determined using ABI model 377 Automated Sequencers. Microsatellite markers comprising a variation of a human linkage mapping panel as released from the Cooperative Human Linkage Center (CHLC), also known as the Weber lab screening set version 8, were obtained from Research Genetics Inc. (Huntsville, Ala.) in the fluorescent dye-conjugated form (Dubovsky et al., *Hum. Mol. Genet*. March; 4(3):449-452 (1995)).

Our variation of the Weber 8 screening set consists of 529 markers with an average spacing of 6.87 cM (autosomes only) and 6.98 cM (all chromosomes). Eighty-nine percent of the markers consist of either tri- or tetra-nucleotide microsatellites. In addition, there exist no gaps in chromosomal coverage greater than 17.5 cM.

Study subject genomic DNA (5 µl; 4.5 ng/µl) was amplified in a 10 µl PCR reaction using AmpliTaq Gold DNA polymerase (0.225 U) and containing the final reaction components: 1×PCR buffer (80 mM $(NH_4)_2SO_4$, 30 mM Tris-HCl (pH 8.8), 0.5% Tween-20), 200 µM each dATP, dCTP, dGTP and dTTP, 1.5-3.5 µM $MgCl_2$ and 250 µM forward and reverse PCR primers. PCR reactions were set up in 192 well plates (Costar) using a Tecan Genesis 150 robotic workstation equipped with a refrigerated deck. PCR reactions were overlaid with 20 µl mineral oil, and thermocycled on an MJ Research Tetrad DNA Engine equipped with four 192 well heads under the following conditions: 92° C. for 3 min, 6 cycles of 92° C. 30 sec, 56° C. 1 min, 72° C. 45 sec, followed by 20 cycles of 92° C. 30 sec, 55° C. 1 min, 72° C. 45 sec and a 6 min incubation at 72° C. PCR products of 8-12 microsatellite markers were subsequently pooled using a Tecan Genesis 200 robotic workstation into two 96 well microtitre plates (2.0 µl PCR product from TET and FAM labeled markers, 3.0 l REX labeled markers) and brought to a final volume of 25 µl with $H_2bO$. 1.9 µl of pooled PCR product was transferred to a loading plate and combined with 3.0 µl loading buffer (loading buffer is 2.5 l formamide/blue dextran (9.0 mg/ml), 0.5 µl GS-500 TAMRA labeled size standard, Perkin-Elmer/ABI division). Samples were denatured in the loading plate for 4 min at 95° C., placed on ice for 2 min, and electrophoresed in a 5% denaturing polyacrylamide gel (FMC on the ABI 377XL). Samples (0.8 µl) were loaded using an 8 channel Hamilton Syringe pipettor.

Each gel consisted of 62 study subjects and 2 control subjects (CEPH parents ID #1331-01 and 1331-02, Coriell Cell Repository, Camden, N.J.). Genotyping gels were scored in duplicate by investigators blind to patient identity and affection status using GENOTYPER analysis software V 1.1.12 (ABI Division, Perkin Elmer Corporation). Nuclear families were loaded onto the gel with the parents flanking the siblings to facilitate error detection. Data with allele peak amplitude less than 100, as detected by GENESCAN analysis software V 2.0.2 (ABI Division, Perkin Elmer Corporation), were either left unscored or rerun.

The final tables obtained from the Genotyper output for each gel analysed were imported into a Sybase Database. Allele calling (binning) was performed using the SYBASE version of the ABAS software (Ghosh et al, *Genome Research* 7:165-178 (1997)). Offsize bins were checked manually and incorrect calls were corrected or blanked. The binned alleles were then imported into the program MENDEL (Lange et al., *Genetic Epidemiology*, 5, 471 (1988)) for inheritance checking using the USERM13 subroutine (Boehnke et al, *AM. J. Hum. Genet.* 48:22-25 (1991)). Non-inheritance was investigated by examining the genotyping traces and once all discrepancies were resolved, the subroutine USERM13 was used to estimate allele frequencies.

C. Linkage Analysis

Linkage analysis is possible because of the nature of inheritance of chromosomes from parents to offspring. During meiosis, the two parental homologues pair to guide their proper separation to daughter cells. While they are lined up and paired, the two homologues exchange pieces of the chromosomes, in an event called "crossing over" or "recombination." The resulting chromosomes contain parts that originate from both parental homologues. The closer together two sequences are on the chromosome, the less likely that a recombination event will occur between them, and the more closely linked they are. Data obtained from the different families are combined and analyzed together by a computer using statistical methods. The result is information indicating the evidence for linkage between the genetic markers used and a disease susceptibility locus. A recombination frequency of 1% is equivalent to approximately 1 map unit, a relationship that holds up to frequencies of about 20% or 20 cM. Furthermore, 1 centiMorgan (cM) is roughly equivalent to 1,000 kb of DNA.

The entire human genome is 3,300 cM long. In order to find an unknown disease gene within 5-10 cM of a marker locus, the whole human genome can be searched with roughly 330 informative marker loci spaced at approximately 10 cM intervals (Botstein et al, *Am. J. Hum. Genet.*, 32:314-331 (1980)). The reliability of linkage results is established by using a number of statistical methods. The methods most commonly used for the detection by linkage analysis of oligogenes involved in the etiology of a complex trait are non-parametric or model-free methods which have been implemented into the computer programs MAPMAKER/SIBS (Kruglyak L & Lander E S, Am J Hum Genet. 57:439-454, 1995) and GENE-HUNTER (Kruglyak L et al., Am J Hum Genet. 58:1347-1363, 1996). Linkage analysis is performed by typing members of families with multiple affected individuals at a given marker locus and evaluating if the affected members (excluding parent-offspring pairs) share alleles at the marker locus that are identical by descent (IBD) more often than expected by chance alone. As a result of the rapid advances in mapping the human genome over the last few years, and concomitant improvements in computer methodology, it has become feasible to carry out linkage analyses using multi-point data. Multi-point analysis provides a simultaneous analysis of linkage between the trait and several linked genetic markers, when the recombination distance among the markers is known. A LOD score statistic is computed at multiple locations along a chromosome to measure the evidence that a susceptibility locus is located nearby. A LOD score is the logarithm base 10 of the ratio of the likelihood that a susceptibility locus exists at a given location to the likelihood that no susceptibility locus is located there. By convention, when testing a single marker, a total LOD score greater than +3.0 (that is, odds of linkage being 1,000 times greater than odds of no linkage) is considered to be significant evidence for linkage.

Multi-point analysis is advantageous for two reasons. First, the informativeness of the pedigrees is usually increased. Each pedigree has a certain amount of potential information, dependent on the number of parents heterozygous for the marker loci and the number of affected individuals in the family. However, few markers are sufficiently polymorphic as to be informative in all those individuals. If multiple markers are considered simultaneously, then the probability of an individual being heterozygous for at least one of the markers is greatly increased. Second, an indication of the position of the disease gene among the markers may be determined. This allows identification of flanking markers, and thus eventually allows identification of a small region in which the disease gene resides.

For the initial linkage analysis, the phenotype and asthma affection status were defined by a patient described above who answered the following questions in the affirmative: (i) have you ever had asthma, (ii) do you have a current physician's diagnosis of asthma, and (iii) are you currently taking asthma medications? Medications include inhaled or oral bronchodilators, cromolyn, theophylline or steroids.

The distribution of the number of genotyped affected siblings was as follows: 88.7% of the families had 2 siblings, 10.9% had 3 siblings and 0.5% had 4 siblings. Ninety eight families were ascertained in the US and 386 in the UK.

Allele sharing methods, implemented in the MAPMAKER/SIBS (Kruglyak L & Lander E S, Am J Hum Genet. 57:439-454, 1995), were used on our sample of affected sibling pairs. Multipoint linkage analyses were performed using 54 polymorphic markers spanning a 162 cM region on both arms of chromosome 12. The map location and distances between markers were obtained from the genetic maps published by the Marshfield medical research foundation (http://www.marshmed.org/genetics/). Ambiguous order in the Marshfield map was resolved using the program MULTIMAP (Matise T C et al., Nature Genet. 6:384-390, 1994) on the 46.

FIG. 1 displays the multipoint LOD score against the map location of markers along chromosome 12. A Maximum LOD Score (MLS) of 2.9 was obtained at location 161.7 cM, 1.0 cM distal to markers D12597 and D1251045. An excess sharing by descent (Identity By Descent, IBD=2) of 0.31 was observed at the maximum LOD score. Table 1 lists the single and multipoint LOD scores at each marker.

These data suggest that chromosome 12 is a location that may contain a gene or genes involved in asthma and diseases thereof

TABLE 1

Chromosome 12 Linkage Analysis

| Marker | Distance | Two-point | Multipoint |
| --- | --- | --- | --- |
| D12S372 | 6.4 | 0.0 | 0.0 |
| GATA49D12 | 17.7 | 0.0 | 0.0 |
| D12S77 | 20.3 | 0.0 | 0.0 |
| D12S391 | 26.2 | 0.0 | 0.0 |
| D12S358 | 26.2 | 0.0 | 0.0 |
| D12S364 | 30.6 | 0.2 | 0.0 |
| D12S373 | 36.1 | 0.0 | 0.0 |
| D12S1042 | 48.7 | 0.0 | 0.0 |
| GATA91H06 | 56.3 | 0.0 | 0.0 |
| D12S368 | 66.0 | 0.2 | 0.3 |
| D12S398 | 68.2 | 0.2 | 0.4 |
| D12S83 | 75.2 | 1.1 | 0.0 |
| D12S1294 | 78.1 | 0.0 | 0.0 |
| IFNgama | 80.4 | 0.0 | 0.0 |
| D12S375 | 80.5 | 0.3 | 0.0 |
| D12S43 | 80.5 | 0.3 | 0.0 |
| D12S1052 | 83.2 | 0.0 | 0.0 |
| D12S92 | 83.2 | 1.0 | 0.0 |
| D12S326 | 86.4 | 0.1 | 0.1 |
| D12S64 | 89.4 | 0.0 | 0.2 |
| D12S379 | 93.7 | 0.0 | 0.1 |

TABLE 1-continued

Chromosome 12 Linkage Analysis

| Marker | Distance | Two-point | Multipoint |
|---|---|---|---|
| D12S311 | 94.5 | 0.1 | 0.0 |
| D12S82 | 95.0 | 0.1 | 0.1 |
| D12S819 | 95.0 | 0.0 | 0.1 |
| D12S1064 | 95.0 | 0.0 | 0.0 |
| D12S95 | 96.1 | 0.2 | 0.2 |
| D12S829 | 97.2 | 0.1 | 0.6 |
| D12S1706 | 104.1 | 0.6 | 0.4 |
| D12S1300 | 104.1 | 0.2 | 0.3 |
| D12S1727 | 107.2 | 0.0 | 0.1 |
| D12S1607 | 107.9 | 0.0 | 0.1 |
| IGF1 | 109.5 | 0.0 | 0.0 |
| PAH | 109.5 | 0.0 | 0.0 |
| D12S360 | 111.3 | 0.0 | 0.0 |
| D12S338 | 111.9 | 0.0 | 0.0 |
| D12S78 | 111.9 | 0.0 | 0.0 |
| D12S811 | 120.7 | 0.1 | 0.3 |
| D12S1341 | 123.0 | 0.0 | 0.5 |
| NOS1 | 123.1 | 0.1 | 0.4 |
| D12S2070 | 125.3 | 0.2 | 0.7 |
| D12S366 | 133.3 | 1.2 | 1.7 |
| D12S1619 | 134.5 | 0.8 | 1.8 |
| D12S385 | 135.1 | 2.0 | 1.6 |
| PLA2G1B | 136.8 | 0.9 | 1.4 |
| D12S395 | 136.8 | 2.1 | 1.5 |
| D12S300 | 140.2 | 0.9 | 1.7 |
| D12S342 | 144.8 | 1.6 | 2.2 |
| D12S324 | 147.2 | 1.3 | 1.4 |
| D12S2078 | 149.6 | 0.9 | 1.9 |
| D12S1659 | 155.9 | 0.3 | 1.6 |
| D12S97 | 160.7 | 0.9 | 2.7 |
| D12S1045 | 160.7 | 3.0 | 2.8 |
| D12S392 | 165.7 | 1.1 | 2.3 |
| D12S357 | 168.8 | 0.8 | 1.1 |

D. Linkage Results

The linkage results for chromosome 12 described above were used to delineate a candidate region for disorder-associated gene(s) located on chromosome 12. Gene discovery efforts were initiated in a ~43 cM interval from marker D12S2070 to the 12q telomere, representing a 99% confidence interval. All genes known to map to this interval were considered as candidates. The discovery of novel genes using direct cDNA selection focused on a ~15 cM region approximately between markers D12S1609 and D12S357.

The following section describes details of the efforts to generate cloned coverage of the disorder gene region on chromosome 12, i.e., construction of a BAC contig spanning the region. There are two primary reasons for this: 1) to provide genomic clones for DNA sequencing; analysis of this sequence provides information about the gene content of the region, and 2) to provide reagents for direct cDNA selection; this provides additional information about novel genes mapping to the interval. The physical map consists of an ordered set of molecular landmarks, and a set of bacterial artificial chromosome (BAC, Kim, U.-J., et al., (1996), *Genomics* 34, 213-218 and Shizuya, H., et al., (1992). *Proc. Natl. Acad. Sci. USA* 89, 8794-8797) clones that contain the disorder gene region from chromosome 12q23-qter.

Figure 2:
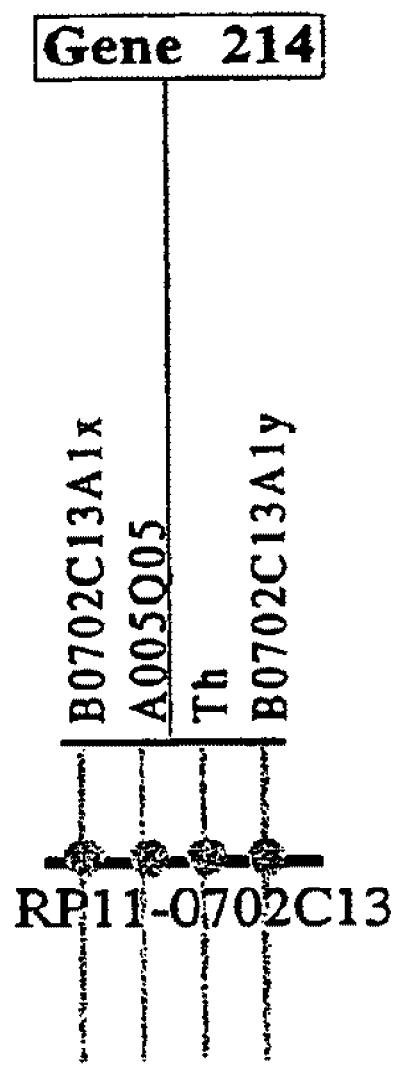
FIG. 2 depicts the STS content of the 12q23-qter BAC RP11-0702C13 containing Gene 214

FIG. 2 depicts the STS content of BAC RP11-0702113 in 12q23-qter. Gene 214 is located within this BAC as indicated at the top of the figure. Markers used to screen the RPCI-11 BAC library (P. deJong—Roswell Park Cancer Institute) are shown vertically above the solid black horizontal line. The following steps were performed:

1. Map Integration. Various publicly available mapping resources were utilized to identify existing STS markers (Olson et al, (1989), Science, 245:1434-1435) in the 12q23-qter region. Resources included the Genome Database (GDB) at the website of: (hypertext transfer protocol, genomedatabase, world wide web.gdb.org/); Genethon at the website of: (hypertext transfer protocol, world wide web. genethon-en.html); Marshfield Center for Medical Genetics at the website of: (hypertext transfer protocol, world wide web. marshmed.org/genetics/); the Whitehead Institute Genome Center at the website of: (hypertext transfer protocol, world wide web-genome.wi.mit.edu/); GeneMap98, dbSTS and dbEST at the website of: NCBI, (hypertext transfer protocol, world wide web, ncbi.nlm.nih.gov/); the Sanger Centre at the website of: (hypertext transfer protocol, world wide web-.sanger.ac.uk/); and the Stanford Human Genome Center at the website of: (hypertext transfer protocol, world wide web-shgc.stanford.edu/). Maps were integrated manually to identify markers mapping to the disorder region. A list of the markers is provided in Table 2.

2. Marker Development. Sequences for existing STSs were obtained from the GDB, RHDB at the website of the Genome Database, RHDB, (hypertext transfer protocol, world wide web. ebi.ac.uk/RHdb/), or NCBI and were used to pick primer pairs (overgos, See Table 2) for BAC library screening. Novel markers were developed either from publicly available genomic sequences, proprietary cDNA sequences or from sequences derived from BAC insert ends (described below). Primers were chosen using a script that automatically performs vector and repetitive sequence masking using Crossmatch (P. Green, U. of Washington); subsequent primer picking was performed using a customized Filemaker Pro database. Primers for use in PCR-based clone confirmation or radiation hybrid mapping (described below) were chosen using the program Primer3 (Steve Rozen, Helen J. Skaletsky (1996, 1997); Primer3 is available at the website of (hypertext transfer protocol, world wide web, -genome.wi.mit.edu/genomesoftware;other/primer3.htm/).

TABLE 2

| Overgo | Locus | DNA Type | Gene | Forward Primer | Reverse Primer |
|---|---|---|---|---|---|
| B0702C13A1x | | BACend | | GTAGTAACAGAATGGACTTTGA (SEQ ID NO: 12) | AGAGAGGAACAGCATCAAAGTC (SEQ ID NO: 13) |
| A005Q05 | | EST | | CAAACAGGGTCCACCGTGGAAA (SEQ ID NO: 14) | GTGTTTCAGCCACATTTCCACG (SEQ ID NO: 15) |
| Th | | Gene | Mucin 8 (MUC8) | ATCCACCGCTAGAAACCCACTC (SEQ ID NO: 16) | GACCATCAACTGATGAGTGGGT (SEQ ID NO: 17) |
| B0702C13A1y | | BACend | | TCATGGGGGTGCTTTGACCTTG (SEQ ID NO: 18) | TGGCCTCAAAGGCTCAAGGTCA (SEQ ID NO: 19) |

3. Radiation Hybrid (R H) Mapping. Radiation hybrid mapping was performed against the Genebridge4 panel (Gyapay, et al., (1996), *Hum. Mol. Genet.* 5:339-46) purchased from Research Genetics, in order to refine the chromosomal localization of genetic markers used in genotyping as well as to identify, confirm and refine localizations of markers from proprietary sequences. Standard PCR procedures were used for typing the RH panel with markers of interest. Briefly, 10 µl PCR reactions contained 25 ng DNA of each of the 93 Genebridge4 RH samples. PCR products were electrophoresed in 2% agarose gels (Sigma) containing 0.5 µg/ml ethidium bromide in 1×TBE at 150 volts for 45 min. The electrophoresis units used were the Model A3-1 systems from Owl Scientific Products. Typically, gels contained 10 tiers of lanes with 50 wells/tier. Molecular weight markers (100 by ladder, GIBCO/BRL) were loaded at both ends of the gel. Images of the gels were captured with a Kodak DC40 CCD camera and processed with Kodak 1D software. The gel data were exported as tab delimited text files; names of the files included information about the panel screened, the gel image files and the marker screened. These data were automatically imported using a customized Perl script into Filemaker databases for data storage and analysis. The data were then automatically formatted and submitted to an internal server for linkage analysis to create a radiation hybrid map using RHMAPPER (Stein, L., Kruglyak, L., Slonim, D., and El Lander (1995); available from the Whitehead Institute/MIT Center for Genome Research, at http://www.genome.wi.mit.edu/ftp/pub/software/rhmapper/, and via anonymous ftp to ftp-.genome.wi.mit.edu, in the directory/pub/software/rhmapper.) The RH mapping results obtained for Gene 214 indicate that it is present in the 12Q 12-qter region at 507.12 cRays on the 684 coordinate system.

4. BAC Library Screening. The protocol used for BAC library screening was based on the "overgo" method, originally developed by John McPherson at Washington University in St. Louis (http://www.tree.caltech.edu/protocols/overgo.html, and Cai, W-W., et al., (1998), *Genomics* 54:387-397). This method involves filling in the overhangs generated after annealing two primers, each 22 nucleotides in length, that overlap by 8 nucleotides. The resulting labeled 36 by product is then used in hybridization-based screening of high density grids derived from the RPCI-11 BAC library (Pieter deJong, Roswell Park Cancer Institute, http://bacpac.med-.buffalo.edu). Typically, 15 probes were pooled together in one hybridization of 12 filters (13.5 genome equivalents).

Stock solutions (2 µM) of combined complementary oligos were heated at 80° C. for 5 min, then placed at 37° C. for 10 min followed by storage on ice. Labeling reactions were set up as follows: 1.0 µl H$_2$O, 5 µl mixed oligos—2 µM each, 0.5 µl BSA (2 mg/ml), 2 µl OLB(-A, -C, -N6) Solution (see below), 0.5 µl $^{32}$P-dATP (3000 Ci/mmol), 0.5 µl $^{32}$P-dCTP (3000 Ci/mmol), 0.5 µl Klenow fragment (5 U/A. The reaction was incubated at room temperature for 1 hr followed by removal of unincorporated nucleotides with Sephadex G50 spin columns.

OLB(-A, -C, -N6) Solution

Solution O—1.25 M Tris-HCL, pH 8, 125 M MgCl$_2$
Solution A—1 ml Solution O, 18 µl 2-mercaptoethanol, 5 µl 0.1M dTTP, 5 µl 0.1 M dGTP
Solution B—2M HEPES-NaOH, pH 6.6
Solution C—3 mM Tris-HCl, pH 7.4, 0.2 mM EDTA
Solutions A, B, and C were combined to a final ratio of 1:2.5:1.5, aliquots were stored at −20° C.

High density BAC library membranes were pre-wetted in 2×SSC at 58° C. Filters were then drained slightly and placed in hybridization solution (1% Bovine serum albumin, 1 mM EDTA—pH 8.0, 7% SDS, and 0.5 M sodium phosphate) pre-warmed to 58° C. and incubated at 58° C. for 2-4 hr. Typically, 6 filters were hybridized per container. Ten ml of pre-hybridization solution were removed, combined with the denatured overgo probes, and added back to the filters. Hybridization was performed overnight at 58° C. The hybridization solution was removed and filters were washed once in 2×SSC, 0.1% SDS, followed by a 30 minute wash in the same solution but at 58° C. Filters were then washed in 1.5×SSC, 01. % SDS at 58° C. for 30 min. 0.5×SSC, 0.1% SDS at 58° C. for 30 min and finally in 0.1×SSC, 0.1% SDS at 58° C. for 30 min. Filters were then wrapped in Saran Wrap and exposed to film overnight. To remove bound probe, filters were treated in 0.1×SSC, 0.1% SDS pre-warmed to 95° C. and allowed to return to room temperature. Clone addresses were determined as described by instructions supplied by RPCI.

Recovery of clonal BAC cultures from the library involved streaking out a sample from the appropriate library well onto LB agar (Maniatis, T., Fritsch, E. F., and J. Sambrook, (1982) Molecular Cloning: A Laboratory Manual, Cold Spring Harbor Laboratory, Cold Spring Harbor, N.Y.) containing 12.5 µg/ml chloramphenicol (Sigma) and incubating overnight. A single colony and a portion of the initial streak quadrant were inoculated into 400 µl LB plus chloramphenicol in wells of a 96 well plate. Cultures were grown overnight at 37° C. For storage, 100 µl of 80% glycerol was added and the plates placed at −80° C. To determine the marker content of clones, aliquots of the 96 well plate cultures were transferred to the surface of nylon filters (GeneScreen Plus, NEN) placed on LB/chloramphenicol Petri plates. Colonies were grown overnight at 37° C. and colony lysis was performed as follows: Filters were placed on pools of 10% SDS for 3 min, 0.5 N NaOH, 1.5 M NaCl for 5 min, and 0.5 M Tris-HCl, pH 7.5, 1 M NaCl for 5 min. Filters were then air dried and washed free of debris in 2×SSC for 1 hr. The filters were air dried for at least 1 hr and DNA crosslinked linked to the membrane using standard conditions. Probe hybridization and filter washing were performed as described above for the primary library screening. Confirmed clones were stored in LB containing 15% glycerol.

In some cases polymerase chain reaction (PCR) was used to confirm the marker content of clones. PCR conditions for each primer pair were initially optimized with respect to MgCl$_2$ concentration. The standard buffer was 10 mM Tris-HCl (pH 8.3), 50 mM KCl, MgCl$_2$, 0.2 mM each dNTP, 0.2 µM each primer, 2.7 ng/µl human DNA, 0.25 units of AmpliTaq (Perkin Elmer) and MgCl$_2$ concentrations of 1.0 mM, 1.5 mM, 2.0 mM or 2.4 mM. Cycling conditions included an initial denaturation at 94° C. for 2 minutes followed by 40 cycles at 94° C. for 15 seconds, 55° C. for 25 seconds, and 72° C. for 25 seconds followed by a final extension at 72° C. for 3 minutes. Depending on the results from the initial round of optimization the conditions were further optimized if necessary. Variables included increasing the annealing temperature to 58° C. or 60° C., increasing the cycle number to 42 and the annealing and extension times to 30 seconds, and using AmpliTaqGold (Perkin Elmer).

5. BAC DNA Preparation. Several different types of DNA preparation methods were used for isolation of BAC DNA. The manual alkaline lysis miniprep protocol listed below (Maniatis, T., Fritsch, E. F., and J. Sambrook, (1982) Molecular Cloning: A Laboratory Manual, Cold Spring Harbor Laboratory, Cold Spring Harbor, N.Y.) was successfully used for most applications, i.e., restriction mapping, CHEF gel analysis and FISH mapping, but was not reproducibly successful in endsequencing. The Autogen protocol described below was used specifically for BAC DNA preparation for endsequencing purposes.

For manual alkaline lysis BAC minipreps, bacteria were grown in 15 ml Terrific Broth containing 12.5 µg/ml chloramphenicol in a 50 ml conical tube at 37° C. for 20 hrs with shaking at 300 rpm. The cultures were centrifuged in a Sorvall RT 6000 D at 3000 rpm (1800×g) at 4° C. for 15 min. The supernatant was then aspirated as completely as possible. In some cases cell pellets were frozen at −20° C. at this step for up to 2 weeks. The pellet was then vortexed to homogenize the cells and minimize clumping. 250 µl of P1 solution (50 mM glucose, 15 mM Tris-HCl, pH 8, 10 mM EDTA, and 100 µg/ml RNase A) was added and the mixture pipeted up and down to mix. The mixture was then transferred to a 2 ml Eppendorf tube. 350 µl of P2 solution (0.2 N NaOH, 1% SDS) was then added, and the mixture mixed gently and incubated for 5 min at room temperature. 350 µl of P3 solution (3M KOAc, pH 5.5) was added and the mixture mixed gently until a white precipitate formed. The solution was incubated on ice for 5 min and then centrifuged at 4° C. in a microfuge for 10 min. The supernatant was transferred carefully (avoiding the white precipitate) to a fresh 2 ml Eppendorf tube, and 0.9 ml of isopropanol was added; the solution was mixed and left on ice for 5 min. The samples were centrifuged for 10 min, and the supernatant removed carefully. Pellets were washed in 70% ethanol and air dried for 5 min. Pellets were resuspended in 200 µl of TE8 (10 mM Tris-HCl, pH 8.0, 1.0 mM EDTA, pH 8.0), and RNase (Boehringer Mannheim) added to 100 µg/ml. Samples were incubated at 37° C. for 30 min, then precipitated by addition of NH$_4$OAc to 0.5 M and 2 volumes of ethanol. Samples were centrifuged for 10 min, and the pellets washed with 70% ethanol followed by air drying and dissolving in 50 µl TE8. Typical yields for this DNA prep were 3-5 µg/15 ml bacterial culture. Ten to 15 µl were used for EcoRI restriction analysis; 5 µl was used for NotI digestion and clone insert sizing by CHEF gel electrophoresis.

Autogen 740 BAC DNA preparations for endsequencing were prepared by dispensing 3 ml of LB media containing 12.5 µg/ml of chloramphenicol into autoclaved Autogen tubes. A single tube was used for each clone. For inoculation, glycerol stocks were removed from −70° C. storage and placed on dry ice. A small portion of the glycerol stock was removed from the original tube with a sterile toothpick and transferred into the Autogen tube; the toothpick was left in the Autogen tube for at least two minutes before discarding. After inoculation the tubes were covered with tape making sure the seal was tight. When all samples were inoculated, the tube units were transferred into an Autogen rack holder and placed into a rotary shaker at 37° C. for 16-17 hours at 250 rpm. Following growth, standard conditions for BAC DNA preparation, as defined by the manufacturer, were used to program the Autogen. Samples were not dissolved in TE8 as part of the program—DNA pellets were left dry. When the program was complete the tubes were removed from the output tray and 30 µl of sterile distilled and deionized H2O was added directly to the bottom of the tube. The tubes were then gently shaken for 2-5 seconds and then covered with parafilm and incubated at room temperature for 1-3 hours. DNA samples were then transferred to an Eppendorf tube and used either directly for sequencing or stored at 4° C. for later use.

6. BAC Clone Characterization. DNA samples prepared either by manual alkaline lysis or the Autogen protocol were digested with EcoRI for analysis of restriction fragment sizes. These data were used to compare the extent of overlap among clones. Typically 1-2 µg were used for each reaction. Reaction mixtures included: 1× Buffer 2 (New England Biolabs), 0.1 mg/ml bovine serum albumin (New England Biolabs), 50 µg/ml RNase A (Boehringer Mannheim), and 20 units of EcoRI (New England Biolabs) in a final volume of 25 µl. Digestions were incubated at 37° C. for 4-6 hours. BAC DNA was also digested with NotI for estimation of insert size by CHEF gel analysis (see below). Reaction conditions were identical to those for EcoRI except that 20 units of NotI were used. Six µl of 6× Ficoll loading buffer containing bromphenol blue and xylene cyanol was added prior to electrophoresis.

EcoRI digests were analyzed on 0.6% agarose (Seakem, FMC Bioproducts) in 1×TBE containing 0.5 µg/ml ethidium bromide. Gels (20 cm×25 cm) were electrophoresed in a Model A4 electrophoresis unit (Owl Scientific) at 50 volts for 20-24 hrs. Molecular weight size markers included undigested lambda DNA, HindIII digested lambda DNA, and HaeIII digested .X174 DNA. Molecular weight markers were heated at 65° C. for 2 min prior to loading the gel. Images were captured with a Kodak DC40 CCD camera and analyzed with Kodak 1D software.

NotI digests were analyzed on a CHEF DR11 (BioRad) electrophoresis unit according to the manufacturer's recommendations. Briefly, 1% agarose gels (BioRad pulsed field grade) were prepared in 0.5×TBE, equilibrated for 30 min in the electrophoresis unit at 14° C., and electrophoresed at 6 volts/cm for 14 hrs with circulation. Switching times were ramped from 10 sec to 20 sec. Gels were stained after electrophoresis in 0.5 µg/ml ethidium bromide. Molecular weight markers included undigested lambda DNA, HindIII digested lambda DNA, lambda ladder PFG ladder, and low range PFG marker (all from New England Biolabs).

7. BAC Endsequencing. The sequence of BAC insert ends utilized DNA prepared by either of the two methods described above. The ends of BAC clones were sequenced for the purpose of filling gaps in the physical map and for gene discovery information. The following vector primers specific to the BAC vector pBACe3.6 were used to generate endsequence from BAC clones:

pBAC 5'-2 TGT AGG ACT ATA TTG CTC (SEQ ID NO: 20) and pBAC 3'-1 CGA CAT TTA GGT GAC ACT (SEQ ID NO: 21).

The following sequencing protocol using ABI dye-terminator chemistry was used to set up sequencing reactions for 96 clones. The BigDye (Mix: Perkin Elmer/ABI BigDye) Terminator Ready Reaction Mix with AmpliTaq" FS, Part number 4303151, was used for sequencing with fluorescently labelled dideoxy nucleotides. A master sequencing mix was prepared for each primer reaction set including:

1600 µl of BigDye terminator mix (ABI)
800 µl of 5×CSA buffer (ABI)
800 µl of primer (either pBAC 5'-2 or pBAC 3'-1 at 3.2 µM)

The sequencing cocktail was vortexed to ensure it was well-mixed and 32 µl was aliquoted into each PCR tube. Eight µl of the Autogen DNA for each clone was transferred from the DNA source plate to a corresponding well of the PCR plate. The PCR plates were sealed tightly and centrifuged briefly to collect all the reagents. Cycling conditions were as follows:

95° C. for 5 minutes
  95° C. for 30 seconds
  50° C. for 20 seconds
  65° C. for 4 minutes
  Go to steps 2 through 4 above for an additional 74 times
  4° C. forever At the end of the sequencing reaction, the plates were removed from the thermocycler and centrifuged briefly. Centri•Sep 96 plates were then used according to manufacturer's recommendation to remove unincorporated nucleotides, salts and excess primers. Each sample was resuspended in 1.5 µl of loading dye of which 1.3 µl was loaded on ABI 377 Fluorescent Sequencers. The resulting endsequences were then used to develop markers to rescreen the BAC library for filling gaps and were also analyzed by BLAST searching for EST or gene content.

E. Sub-Cloning and Sequencing of BACS from 12q23-qter

The physical map of the chromosome 12 region provides the BAC clone and location for use as sequencing templates (see FIG. 2). DNA sequencing of the BAC RPCI-11_0702C13 from the region is contained within (SEQ ID NO: 1).

DNA for BAC RPCI-11_0702C13 (the "BAC DNA") was isolated according to one of two protocols: either a Qiagen purification of BAC DNA (Qiagen, Inc., Chatsworth, Calif., per manufacturer's instructions) or a manual purification using a method which is a modification of the standard alkaline lysis/Cesium Chloride preparation of plasmid DNA (see e.g., Ausubel et al, (1997), Current Protocols in Molecular Biology, John Wiley & Sons). Briefly, for the manual protocol, cells were pelleted, resuspended in GTE (50 mM glucose, 25 mM Tris-Cl (pH 8), 10 mM EDTA) and lysozyme (50 mg/ml solution), followed by NaOH/SDS (1% SDS/0.2N NaOH) and then an ice-cold solution of 3M KOAc (pH 4.5-4.8). RNaseA was added to the filtered supernatant, followed by treatment with Proteinase K and 20% SDS. The DNA was then precipitated with isopropanol, dried and resuspended in TE (10 mM Tris, 1 mM EDTA (pH 8.0)). The BAC DNA was further purified by Cesium Chloride density gradient centrifugation (Ausubel et al, (1997), Current Protocols in Molecular Biology, John Wiley & Sons).

Following isolation, the BAC DNA was hydrodynamically sheared using HPLC (Hengen, et al., (1997), *Trends in Biochem. Sci.*, 22:273-274) to an insert size of 2000-3000 bp. After shearing, the DNA was concentrated and separated on a standard 1% agarose gel. A single fraction, corresponding to the approximate size, was excised from the gel and purified by electroelution (Sambrook et al, (1989), *Molecular Cloning: A Laboratory Manual*, Cold Spring Harbor Laboratory, Cold Spring, N.Y.).

The purified DNA fragments were then blunt-ended using T4 DNA polymerase. The healed DNA was then ligated to unique BstXI-linker adapters (5' GTCTTCACCACGGGG (SEQ ID NO: 22) and 5' GTGGTGAAGAC (SEQ ID NO: 23) in 100-1000 fold molar excess). These linkers are complimentary to the BstXI-cut pMPX vectors, while the overhang is not self-complimentary. Therefore, the linkers will not concatemerize nor will the cut-vector re-ligate to itself easily. The linker-adapted inserts were separated from unincorporated linkers on a 1% agarose gel and purified using GeneClean (BIO 101, Inc.). The linker-adapted insert was then ligated to a modified pBlueScript vector to construct a "shotgun" subclone library. The vector contains an out-of-frame lacZ gene at the cloning site which becomes in-frame in the event that an adapter-dimer is cloned, allowing these to be avoided by their blue color.

All subsequent steps were based on sequencing by ABI377 automated DNA sequencing methods. Only major modifications to the protocols are highlighted. Briefly, the library was then transformed into DH5-competent cells (Gibco/BRL, DH5-transformation protocol). Quality was assessed by plating onto antibiotic plates containing ampicillin and IPTG/Xgal. The plates were incubated overnight at 37° C. Successful transformants were then used for plating of clones and picking for sequencing. The cultures were grown overnight at 37° C. DNA was purified using a silica bead DNA preparation (Ng et al, *Nucl. Acids Res.*, 24:5045-5047 (1996)) method. In this manner, 25 µg of DNA was obtained per clone.

These purified DNA samples were then sequenced using ABI dye-terminator chemistry. The ABI dye terminator sequence reads were run on ABI377 machines and the data were directly transferred to UNIX machines following lane tracking of the gels. All reads were assembled using PHRAP (P. Green, Abstracts of DOE Human Genome Program Contractor-Grantee Workshop V, January 1996, p. 157) with default parameters and quality scores. SEQ ID NO:1 comprises a portion of the BAC which includes the genomic sequence of Gene 214

F. Gene Identification

Any gene or EST mapping to the interval based on public map data or proprietary map data was considered a candidate disorder gene.

1. Gene Identification from clustered DNA fragments. DNA sequences corresponding to gene fragments in public databases (Genbank and human dbEST) and proprietary cDNA sequences (IMAGE consortium and direct selected cDNAs) were masked for repetitive sequences and clustered using the PANGEA Systems (Oakland, Calif.) EST clustering tool. The clustered sequences were then subjected to computational analysis to identify regions bearing similarity to known genes. This protocol included the following steps:

i. The clustered sequences were compared to the publicly available Unigene database (National Center for Biotechnology Information, National Library of Medicine, 38A, 8N905, 8600 Rockville Pike, Bethesda, Md. 20894; www.ncbi.nlm.nih.gov) using the blastn2 algorithm (Altschul et al, *Nucl. Acids Res.*, 25:3389-3402 (1997)). The parameters for this search were: E=0.05, v=50, B=50 (where E is the expected probability score cutoff, V is the number of database entries returned in the reporting of the results, and B is the number of sequence alignments returned in the reporting of the results (Altschul et al, *J. Mol. Biol.*, 215:403-410 (1990)).

ii. The clustered sequences were compared to the Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389-3402 (1997)). The parameters for this search were E=0.05, V=50, B=50, where E, V, and B are defined as above.

iii. The clustered sequences were translated into protein for all six reading frames, and the protein sequences were compared to a non-redundant protein database compiled from Genpept Swissprot PIR (National Center for Biotchnology Information, National Library of Medicine, 38A, 8N905, 8600 Rockville Pike, Bethesda, Md. 20894; www.ncbi.nlm.nih.gov). The parameters for this search were E=0.05, V=50, B=50, where E, V, and B are defined as above.

iv. The clustered sequences were compared to BAC sequences (see below) using blastn2 (Altschul et al, *Nucl. Acids. Res.*, 25:3389-3402 (1997)). The parameters for this search were E=0.05, V=50, B=50, where E, V, and B are defined as above.

2. Gene Identification from BAC Genomic Sequence. Following assembly of the BAC sequences into contigs, the contigs were subjected to computational analyses to identify coding regions and regions bearing DNA sequence similarity to known genes. This protocol included the following steps:

i. Contigs were degapped. The sequence contigs often contain symbols (denoted by a period symbol) that represent locations where the individual ABI sequence reads have insertions or deletions. Prior to automated computational analysis of the contigs, the periods were removed. The original data were maintained for future reference.

ii. BAC vector sequences were "masked" within the sequence by using the program crossmatch (Phil Green, http:\\chimera.biotech.washington.edu\UWGC). Since the shotgun library construction detailed above left some BAC vector in the shotgun libraries, this program was used to compare the sequence of the BAC contigs to the BAC vector and to mask any vector sequence prior to subsequent steps. Masked sequence was marked by an "X" in the sequence files, and remained inert during subsequent analyses.

iii. *E. coli* sequences contaminating the BAC sequences were masked by comparing the BAC contigs to the entire *E. coli* DNA sequence.

iv. Repetitive elements known to be common in the human genome were masked using crossmatch. In this implementation of crossmatch, the BAC sequence is compared to a database of human repetitive elements (Jerzy Jerka, Genetic Information Research Institute, Palo Alto, Calif.). The masked repeats were marked by X and remained inert during subsequent analyses.

v. The location of exons within the sequence was predicted using the MZEF computer program (Zhang, *Proc. Natl. Acad. Sci.*, 94:565-568 (1997); GenScan (Burge and Karlin, *J. Mol. Biol.*, 268:78-94)).

vi. The sequence was compared to the publicly available unigene database (National Center for Biotechnology Information, National Library of Medicine, 38A, 8N905, 8600 Rockville Pike, Bethesda, Md. 20894; www.ncbi.nlm.nih.gov) using the blastn2 algorithm (Altschul et al, *Nucl. Acids Res.*, 25:3389-3402 (1997)). The parameters for this search were: $E=0.05$, $v=50$, $B=50$ (where E is the expected probability score cutoff, V is the number of database entries returned in the reporting of the results, and B is the number of sequence alignments returned in the reporting of the results (Altschul et al, *J. Mol. Biol.*, 215:403-410 (1990)).

vii. The sequence was translated into protein for all six reading frames, and the protein sequences were compared to a non-redundant protein database compiled from Genpept Swissprot PIR (National Center for Biotchnology Information, National Library of Medicine, 38A, 8N905, 8600 Rockville Pike, Bethesda, Md. 20894; www.ncbi.nlm.nih.gov). The parameters for this search were $E=0.05$, $V=50$, $B=50$, where E, V, and B are defined as above.

viii. The BAC DNA sequence was compared to a database of clustered sequences using blastn2 (Altschul et al, *Nucl. Acids. Res.*, 25:3389-3402 (1997)). The parameters for this search were $E=0.05$, $V=50$, $B=50$, where E, V, and B are defined as above. The database of clustered sequences was prepared utilizing a proprietary clustering technology (Pangea Systems, Inc.) using cDNA clones derived from direct selection experiments (described below), human dbEST mapping to the 12q23-qter region, proprietary cDNAs, Genbank genes and IMAGE consortium cDNA clones.

ix. The BAC sequence was compared to the sequences derived from the ends of BACs from the region on chromosome 12 using blastn2 (Altschul et al, *Nucl. Acids. Res.*, 25:3389-3402 (1997)). The parameters for this search were $E=0.05$, $V=50$, $B=50$, where E, V, and B are defined as above.

x. The BAC sequence was compared to the Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389-3402 (1997)). The parameters for this search were $E=0.05$, $V=50$, $B=50$, where E, V, and B are defined as above.

xi. The BAC sequence was compared to the STS division of Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al., 1997). The parameters for this search were $E=0.05$, $V=50$, $B=50$, where E, V, and B are defined as above.

xii. The BAC sequence was compared to the Expressed Sequence Tag (EST) Genbank database (National Center for Biotchnology Information, National Library of Medicine, 38A, 8N905, 8600 Rockville Pike, Bethesda, Md. 20894; www.ncbi.nlm.nih.gov) using blastn2 (Altschul et al., *Nucl. Acids. Res.*, 25:3389-3402 (1997)). The parameters for this search were $E=0.05$, $V=50$, $B=50$, where E, V, and B are defined as above.

xiii. The BAC sequence was compared to the Expressed Sequence Tag (EST) Genbank database (National Center for Biotchnology Information, National Library of Medicine, 38A, 8N905, 8600 Rockville Pike, Bethesda, Md. 20894; www.ncbi.nlm.nih.gov) using blastn2 (Altschul et al., *Nucl. Acids. Res.*, 25:3389-3402 (1997)). The parameters for this search were $E=0.05$, $V=50$, $B=50$, where E, V, and B are defined as above.

G. cDNA Cloning and Expression Analysis

1. Construction of cDNA libraries. Directionally cloned cDNA libraries from normal lung and bronchial epithelium were constructed using standard methods described previously (Soares et. al., 1994, Automated DNA Sequencing and Analysis, Adams, Fields and Venter, Eds., Academic Press, NY, pages 110-114). Total and cytoplasmic RNAs were extracted from tissue or cells by homogenizing the sample in the presence of Guanidinium Thiocyanate-Phenol-Chloroform extraction buffer (e.g. Chomczynski and Sacchi, Anal. Biochem., 162:156-159 (1987)) using a polytron homogenizer (Brinkman Instruments). PolyA+ RNA was isolated from total/cytoplasmic RNA using dynabeads-dT according to the manufacturer's recommendations (Dynal, Inc.). The ds cDNA synthesized was then ligated into the plasmid vector pBluescript II KS+ (Stratagene, La Jolla, Calif.), and the ligation mixture was transformed into *E. coli* host DH10B or DH12S by electroporation (Soares, 1994). Following overnight growth at 37° C., DNA was recovered from the *E. coli* colonies after scraping the plates by processing as directed for the Mega-prep kit (Qiagen, Chatsworth, Calif.). The quality of the cDNA libraries was estimated by counting a portion of the total number of primary transformants, determining the average insert size and the percentage of plasmids with no cDNA insert. Additional cDNA libraries (human total brain, heart, kidney, leukocyte, and fetal brain) were purchased from Life Technologies, Bethesda, Md.

cDNA libraries, both oligo (dT) and random hexamer-primed were used for isolating cDNA clones mapping within the disorder critical region. Four 10×10 arrays of each of the cDNA libraries were prepared as follows: the cDNA libraries were titered to $2.5 \times 10^6$ using primary transformants. The appropriate volume of frozen stock was used to inoculate 2 L of LB/ampicillin (100 μg/μl). 400 aliquots containing 4 ml of the inoculated liquid culture were generated. Each tube contained about 5000 cfu. The tubes were incubated at 30° C. overnight with shaking until an OD of 0.7-0.9 was obtained. Frozen stocks were prepared for each of the cultures by aliquotting 300 μl of culture and 100 μl of 80% glycerol. Stocks were frozen in a dry ice/ethanol bath and stored at −70° C. DNA was isolated from the remaining culture using the Qiagen (Chatsworth, Calif.) spin mini-prep it according to the manufacturer's instructions. The DNAs from the 400 cultures were pooled to make 80 column and row pools. Markers were designed to amplify putative exons from candidate genes. Once a standard PCR condition was identified and specific cDNA libraries were determined to contain cDNA clones of interest, the markers were used to screen the arrayed library. Positive addresses indicating the presence of cDNA clones were confirmed by a second PCR using the same markers.

Once a cDNA library was identified as likely to contain cDNA clones corresponding to a specific transcript of Gene 214, it was used to isolate a clone or clones containing cDNA inserts. This was accomplished by a modification of the standard "colony screening" method (Sambrook et al, Molecular Cloning: A Laboratory Manual, Cold Spring Harbor Laboratory, Cold Spring Harbor N.Y. (1989)). Specifically, twenty 150 mm LB+ampicillin agar plates were spread with 20,000 colony forming units (cfu) of cDNA library and the colonies allowed to grow overnight at 37° C. Colonies were transferred to nylon filters (Hybond from Amersham, or equivalent) and duplicates prepared by pressing two filters together essentially as described (Sambrook et al, Molecular Cloning: A Laboratory Manual, Cold Spring Harbor Laboratory, Cold Spring Harbor N.Y. (1989)). The "master" plate was then incubated an additional 6-8 hrs to allow the colonies additional growth. The DNA from the bacterial colonies was then bound onto the nylon filters by treating the filters sequentially with denaturing solution (0.5 N NaOH, 1.5 M NaCl) for two minutes, neutralization solution (0.5 M Tris-Cl pH 8.0, 1.5 M NaCl) for two minutes (twice). The bacterial colonies were removed from the filters by washing in a solution of 2×SSC/2% SDS for one minute while rubbing with tissue paper. The filters were air dried and baked under vacuum at 80° C. for 1-2 hrs to cross link the DNA to the filters.

cDNA hybridization probes were prepared by random hexamer labelling (Fineberg and Vogelstein, Anal. Biochem., 132:6-13 (1983)) or by including gene-specific primers and no random hexamers in the reaction (for small fragments). The colony membranes were then pre-washed in 10 mM Tris-Cl pH 8.0, 1 M NaCl, 1 mM EDTA, 0.1% SDS for 30 minutes at 55° C. Following the pre-wash, the filters were pre-hybridized in >2 ml/filter of 6×SSC, 50% deionized formamide, 2% SDS, 5×Denhardt's solution, and 100 mg/ml denatured salmon sperm DNA, at 42° C. for 30 minutes. The filters were then transferred to hybridization solution (6×SSC, 2% SDS, 5×Denhardt's, 100 mg/ml denatured salmon sperm DNA) containing denatured a-32P-dCTP-labelled cDNA probe and incubated overnight at 42° C.

The following morning, the filters were washed under constant agitation in 2×SSC, 2% SDS at room temperature for 20 minutes, followed by two washes at 65° C. for 15 minutes each. A second wash was performed in 0.5×SSC, 0.5% SDS for 15 minutes at 65° C. Filters were then wrapped in plastic wrap and exposed to radiographic film. Individual colonies on plates were aligned with the autoradiograph and positive clones picked into a 1 ml solution of LB Broth containing ampicillin. After shaking at 37° C. for 1-2 hours, aliquots of the solution were plated on 150 mm plates for secondary screening. Secondary screening was identical to primary screening (above) except that it was performed on plates containing ~250 colonies so that individual colonies could be clearly identified. Positive cDNA clones were characterized by restriction endonuclease cleavage, PCR, and direct sequencing to confirm the sequence identity between the original probe and the isolated clone.

To obtain the full-length cDNA, novel sequence from the 5'-end of the clone was used to reprobe the library. This process is repeated until the length of the cDNA cloned matched that of the mRNA, estimated by Northern analysis.

Rapid Amplification of cDNA ends (RACE) was performed following the manufacturer's instructions using a Marathon cDNA Amplification Kit (Clontech, Palo Alto, Calif.) as a method for cloning the 5' and 3' ends of candidate genes. cDNA pools were prepared from total RNA by performing first strand synthesis, where a sample of total RNA sample was mixed with a modified oligo (dT) primer, heated to 70° C., cooled on ice and followed by the addition of: 5× first strand buffer, 10 mM dNTP mix, and AMV Reverse Transcriptase (20 U/µl). The reaction mixture was incubated at 42° C. for an hour and placed on ice. For second strand synthesis, the following components were added directly to the reaction tube: 5× second strand buffer, 10 mM dNTP mix, sterile water, 20× second strand enzyme cocktail and the reaction tube was incubated at 16° C. for 1.5 hours. T4 DNA Polymerase was added to the reaction tube and incubated at 16° C. for 45 minutes. The second-strand synthesis was terminated with the addition of an EDTA/Glycogen mix. The sample was subjected to a phenol/chloroform extraction and an ammonium acetate precipitation. The cDNA pools were checked for quality by analyzing on an agarose gel for size distribution. Marathon cDNA adapters were then ligated onto the cDNA ends. The specific adapters contained priming sites that allowed for amplification of either 5' or 3' ends, and varied depending on the orientation of the gene specific primer (GSP) that was chosen. An aliquot of the double stranded cDNA was added to the following reagents: 10 µM Marathon cDNA adapter, 5×DNA ligation buffer, T4 DNA ligase. The reaction was incubated at 16° C. overnight and heat inactivated to terminate the reaction. PCR was performed by the addition of the following to the diluted double stranded cDNA pool: 10× cDNA PCR reaction buffer, 10 µM dNTP mix, 10 µM GSP, 10 µM AP1 primer (kit), 50× Advantage cDNA Polymerase Mix. Thermal Cycling conditions were 94° C. for 30 seconds, 5 cycles of 94° C. for 5 seconds, 72° C. for 4 minutes, 5 cycles of 94° C. for 5 seconds, 70° C. for 4 minutes, 23 cycles of 94° C. for 5 seconds, 68° C. for 4 minutes. After the first round of PCR was performed using the GSP to extend to the end of the adapter to create the adapter primer binding site, exponential amplification of the specific cDNA of interest was performed. Usually, a second, nested PCR was performed to provide specificity. The RACE product was analyzed on an agarose gel. Following excision from the gel and purification (GeneClean, BIO 101), the RACE product was then cloned into pCTNR (General Contractor DNA Cloning System, 5'-3', Inc.) and sequenced to verify that the clone was specific to Gene 214.

2. Expression Analysis. To characterize the expression of Gene 214, a series of experiments were performed. First, oligonucleotide primers were designed for use in the polymerase chain reaction (PCR) so that portions of a cDNA, EST, or genomic DNA could be amplified from a pool of DNA molecules or RNA population (RT-PCR). The PCR primers were used in a reaction containing genomic DNA to verify that they generated a product of the predicted size (based on the genomic sequence). A critical piece of data that is required when characterizing novel genes is the length, in nucleotides, of the processed transcript or messenger RNA (mRNA). Those skilled in the art primarily determine the length of an mRNA by Northern analysis (Sambrook et al, Molecular Cloning: A Laboratory Manual, Cold Spring Harbor Laboratory, Cold Spring Harbor N.Y. (1989)). Probes were generated using one of the methods described below. Briefly, sequence verified IMAGE consortium cDNA clones were digested with appropriate restriction endonucleases to release the insert. The restriction digest was electrophoresed on an agarose gel and the bands containing the insert were excised. The gel piece containing the DNA insert was placed in a Spin-X (Corning Costar Corporation, Cambridge, Mass.) or Supelco spin column (Supelco Park, Pa.) and spun at high speed for 15 mins. The DNA was ethanol precipitated and resuspended in TE. Alternatively, PCR products obtained from genomic DNA or RT-PCR were also purified as described above.

Figure 9:
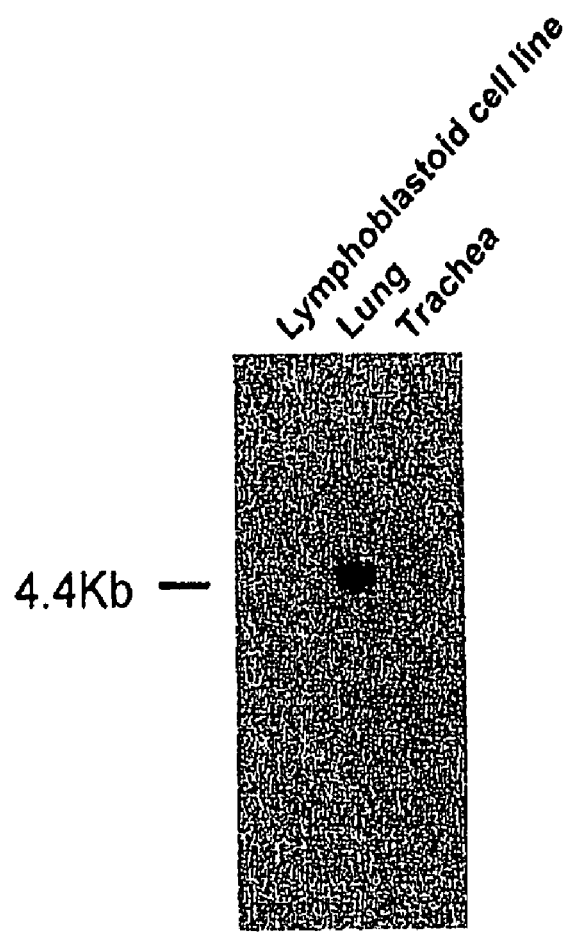
FIG. 9 shows a Northern Analysis of Gene 214.

Inserts purified from IMAGE clones were random primer labelled (Feinberg and Vogelstein) to generate probes for hybridization. Probes from purified PCR products were generated by incorporation of a-$^{32}$P-dCTP in second round of PCR. FIG. 9 is the Northern blot for Gene 214 which includes PolyA+ selected RNA from 1) a lymphoblast cell line from as asthmatic individual, 2) lung and 3) trachea. Expression of Gene 214 was detected in lung at moderate levels, with a weak signal in trachea. Expression was not found in any other tissues examined. The lung-specific expression of Gene 214 implicates it as a gene involved in lung biology and further valicates as a candidate asthma gene.

3. RT-PCR. RT-PCR was used as an alternate method to Northern blotting to detect mRNAs with low levels of expression. Total RNA from multiple human tissues was purchased from Clontech (Palo Alto, Calif.) and genomic DNA was removed from the total RNA by DNaseI digestion. The "Superscript' Preamplification System for First strand cDNA synthesis" (Life Technologies, Gaithersburg, Md.) was used according to manufacturer's specifications with oligo(dT) or random hexamers to synthesize cDNA from the DNaseI treated total RNA. Gene specific primers were used to amplify the target cDNAs in a 30 µl PCR reaction containing 0.5 µl of first strand cDNA, 1 µl sense primer (10 uM), 1 µl antisense primer (10 uM), 3 µl dNTPs (2 mM), 1.2 µl MgCl$_2$ (25 mM), 3 µl 10×PCR buffer and 1 unit of Taq Polymerase (Perkin Elmer). The PCR reaction was initially denatured at 94° C. for 4 min, then 30 cycles of denaturation at 94° C. for 30 sec, annealing at 58° C. for 1 min and extension at 72° C. for 1 min, followed by a final extension at 72° C. for 7 min. PCR products were analyzed on agarose gels.

H. Characteristics and Function of Gene 214

BAC RP11-702C13 (196 Kb) maps to chromosome 12q24 and contains the STS marker A005Q05 located approximately 165 cM from the telomere of the p-arm of chromosome 12. Gene 214 maps within a 10,318 kb sequenced contig of the BAC RP11-702C13 (FIG. 2). BLAST analysis against DNA and protein databases indicated that a portion of Gene 214 was 100% homologous to a nucleic acid sequence known as mucin 8

(MUC8). Northern blot analysis of Gene 214 detected a 4.4 Kb transcript in lung (FIG. 9). The MUC8 fragment is 1.4 Kb in length (Shanker et.al., *Am J. Respir. Cell Mol. Biol.*, 16:232-241 (1997)). Enclosed herein are an additional four alternatively transcribed variants. (SEQ ID NO:2, SEQ ID NO:4, SEQ ID NO:6, SEQ ID NO: 8, and SEQ ID NO:10). The five variants of Gene 214/MUC8 contain a putative open reading frames that vary in size, from 1167 bp to 1350 bp, and thus encode proteins from 388 to 449 amino acids (SEQ ID NO:3, SEQ ID NO:5, SEQ ID NO:7, SEQ ID NO: 9, and SEQ ID NO:11).

Mucin 8 belongs to a growing family of genes that encode mucins. Currently, there are 9 members of this family, MUC1, MUC2, MUC3, MUC4, MUC5, MUC5B, MUC6 and MUC7, and the fragment MUC8. All but MUC3 and MUC6 are expressed in the upper and/or lower respiratory tract (Zuhdi Alimam et al., *Am. J. Respir. Cell Mol. Biol.*, 22:253-260 [2000]). All the mucins share a common characteristic: tandem repeated amino acid sequences within the protein core. These repeats are rich in serine, threonine and proline and are heavily glycosylated via O-glycosidic bonds. The tandem repeat units vary in length from as few as 8 to as many as 169 amino acids and are always flanked by non-repeat regions. The MUC8 core protein is unique among the mucins, in that it possesses a degenerate 41 bp tandem repeat that encodes 2 types of consensus peptide repeats; three 41 bp repeats encode one peptide sequence while a 2 bp deletion in the perfect 41 bp repeat disrupts the tandem and generates a second smaller repetitive portion of the protein (Shanker et.al., Biochem. 300:295-298 (1994).

The respiratory epithelium is protected by a viscoelastic gel, mucus, that is normally produced at low levels. In a healthy individual, 10 mls of sputum are transported to the larynx and swallowed. In asthmatic individuals, mucus production is increased. This causes airway obstruction due to the sputum being very tenacious, and hence forming viscid plugs that can be difficult to expectorate. The overproduction of mucus in asthmatics has been attributed to the increased numbers of goblets cells, goblet cell hyperplasia (GCH), and enlargement of the sub-mucosal glands. GCH is presumed to be due to a combination of mucus gland stimulation by neural stimuli and inflammatory mediators. In situ hybridization revealed that multiple airway mucin genes account for the total mucin secretion derived from the airway epithelia. Further, immunohistochemical staining of tracheobronchial epithelium with polyclonal antibodies raised to MUC8, indicated that the protein was primarily localized to sub-mucosal glands (Shanker et. al., *Am J. Respir. Cell Mol. Biol.*, 16:232-241 [1997]). Therefore it is likely that the relationship and functional role of Gene 214/MUC8 are involved in the pathophysiology of asthma and other respiratory diseases.

I. Mutation Analysis

In order to conduct mutation analysis, the genomic structure for Gene 214 was identified. The precise intron-exon junctions were determined based on the consensus sequences at splice junctions. The exon prediction programs MZEF (Zhang, *Proc. Natl. Acad. Sci.*, 94:565-568 (1997); and GenScan (Burge and Karlin, *J. Mol. Biol.*, 268:78-94) were also utilized to help identify the exons.

A combination of fluorescent single stranded confirmation (SSCP) analysis (ABI) and DNA sequencing was utilized to precisely identify and determine the nature of the variant at the nucleotide level. SSCP analysis was used to screen individual DNA for variants. Briefly, polymerase chain reaction (PCR) was used to generate templates from unrealted asthmatic individuals that showed increased sharing for the 12q23-qter chromosomal region and contributed towards linkage. Non-asthmatic individuals were used as controls. Enzymatic amplification of genes within the asthma region on 12q23-qter was accomplished using PCR with oligonucleotides flanking each exon as well as the putative 5' regulatory elements of each gene. The primers were chosen to amplify each exon as well as 15 or more base pairs within each intron on either side of the splice site. The forward and the reverse primers had two different dye colors to allow analysis of each strand and confirm variants independently. Standard PCR assay was utilized for each exon primer pair following optimization. Buffer and cycling conditions were specific to each primer set. The products were denatured using a formamide dye and electrophoresed on non-denaturing acrylamide gels with varying concentrations of glycerol (at least two different glycerol concentrations).

Primers utilized in fluorescent SSCP experiments to screen coding and non-coding regions of Gene 214 for polymorphisms are provided in Table 3. Column one lists the gene targeted for mutation analysis. Column two lists the specific exon analyzed. Column three provides the GTC assigned primer name. Columns four and five list the forward primer sequence and reverse primer sequence, respectively.

SSCP (SSCP primers). The appropriate population of individuals was PCR amplified in 96 well microtitre plates.

Enzymes were purchased from New England Biolabs (NEB). The restriction cocktail containing the appropriate

TABLE 3

| Gene | Exon | SSCP Assay | Forward Primer | Reverse Primer |
|---|---|---|---|---|
| 214 | A | 196_214_A_F_197_214_A_R | GCCCTTAGGGAGAGCAGC (SEQ ID NO: 24) | CCACATCGTGCCTTTGTGTA (SEQ ID NO: 25) |
| 214 | B | 192_214_B_F_193_214_B_R | CACTGTGTTAAAACGCCTGG (SEQ ID NO: 26) | GTTGGGATTACAGGCACGAG (SEQ ID NO: 27) |
| 214 | B | 194_214_B_F_195_214_B_R | CAGAAGCAACCCACATGACC (SEQ ID NO: 28) | ACTACAGGTTTGCACCACCA (SEQ ID NO: 29) |
| 214 | C | 626_214_C_F_627_214_C_R | ATGCTCTCCTGATGGCTCCT (SEQ ID NO: 30) | AGGGAATGCAGGTGCAAAG (SEQ ID NO: 31) |
| 214 | C | 628_214_C_F_629_214_C_R | ACTCGGGAAAGGAAGGCTCT (SEQ ID NO: 32) | CATACCTTGAGTGCACACCG (SEQ ID NO: 33) |

Primers utilized in DNA sequencing for purposes of confirming polymorphisms detected using fluorescent SSCP are provided in Table 4. Column one lists the specific exon sequenced. Column two provides the GTC assigned forward primer name and column three lists the forward primer sequence. Columns four and five lists the GTC assigned reverse primer name and the corresponding reverse primer sequence, respectively.

enzyme for the particular polymorphism is added to the PCR product. The reaction is incubated at the appropriate temperature according to the manufacturer's recommendations (NEB) for two to three hours, followed by a 4° C. incubation. After digestion, the reactions were size fractionated using the appropriate agarose gel depending on the assay specifications (2.5%, 3%, or metaphor). Gels are electrophoresed in 1×TBE Buffer at 170 Volts for approximately two hours.

TABLE 4

| Gene | Exon | ForwardPrimer | ForwardSequence | ReversePrimer | ReverseSequence |
|---|---|---|---|---|---|
| 214 | B | MDSeq_15_214_B_F | GACAGTCTGCTCCACATCCA (SEQ ID NO: 34) | MDSeq_15_214_B_R | TGGAGATGAAGTCTTGCTCTTG (SEQ ID NO: 35) |
| 214 | C | MDSeq_110_214_C_F | ATATGTTTGCTGGCTTTGGG (SEQ ID NO: 36) | MDSeq_110_214_C_R | CCCAGGCTGTGTGTCCTCTA (SEQ ID NO: 37) |

Single nucleotide polymorphisms (SNPs) that were identified in Gene 214 are provided in Table 5. Column one contains the exon or intron in which the SNP was detected. Column two provides a reference sequence in which the SNP appears underlined. Column three lists the base change of the SNP. Column four details the location of the SNP as intronic or exonic. Column five describes the SNP location of the genomic BAC sequence of SEQ ID NO:1. The SNPs are also described in FIGS. 8A-8B).

The gel is illuminated using ultraviolet light and the image is saved as a Kodak 1D file. Using the Kodak 1D image analysis software, the images are scored and the data is exported to EXCEL.

2. ASO assay. The amplicon, containing the polymorphism, was PCR amplified using primers that were used to generate a fragment for sequencing (sequencing primers) or SSCP (SSCP primers). The appropriate population of individuals was PCR amplified in 96 well microtitre plates and

TABLE 5

| Exon | Reference Sequence | PMP | Intron/Exon | Location |
|---|---|---|---|---|
| B | ACTACAGGTTTGCACCACCATGTCCTGCTAATTTTTTTTT (SEQ ID NO: 46) | A > G (SEQ ID NO: 47) | Intron | 6674 |
| B | TGTGCACTCTTGGGCATACGCCTAGGAGTGGAACTGCTG (SEQ ID NO: 48) | C > T (SEQ ID NO: 49) | 3'UTR | 6976 |
| C | GGGCTCTGCGCCACCTCAACCCAGGCGTTTGTTCCGCAG (SEQ ID NO: 50) | C > T (SEQ ID NO: 51) | Intron | 3161 |

Figure 8A:
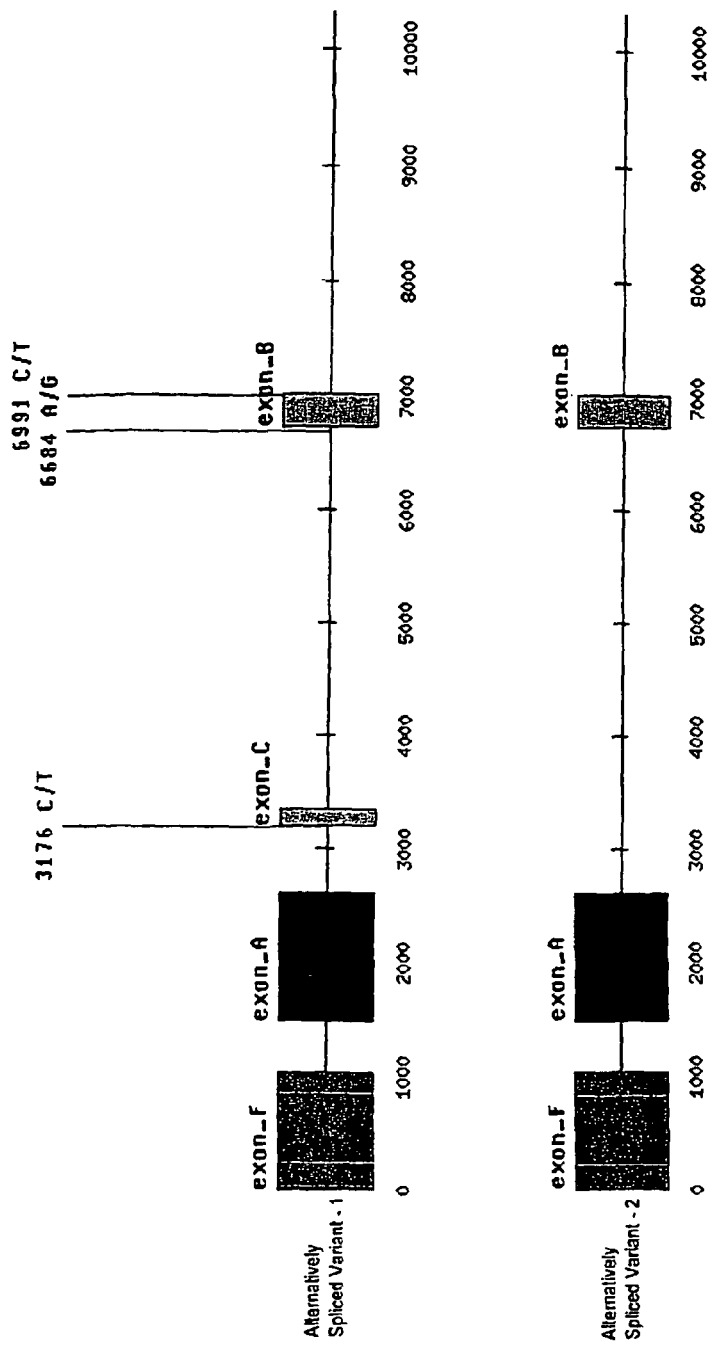
FIGS. 8A-8B show a schematic view of the exons of Gene 214a, 214b, 214c, 214d, and 214e and the corresponding single nucleotide polymorphisms.
Figure 8B:
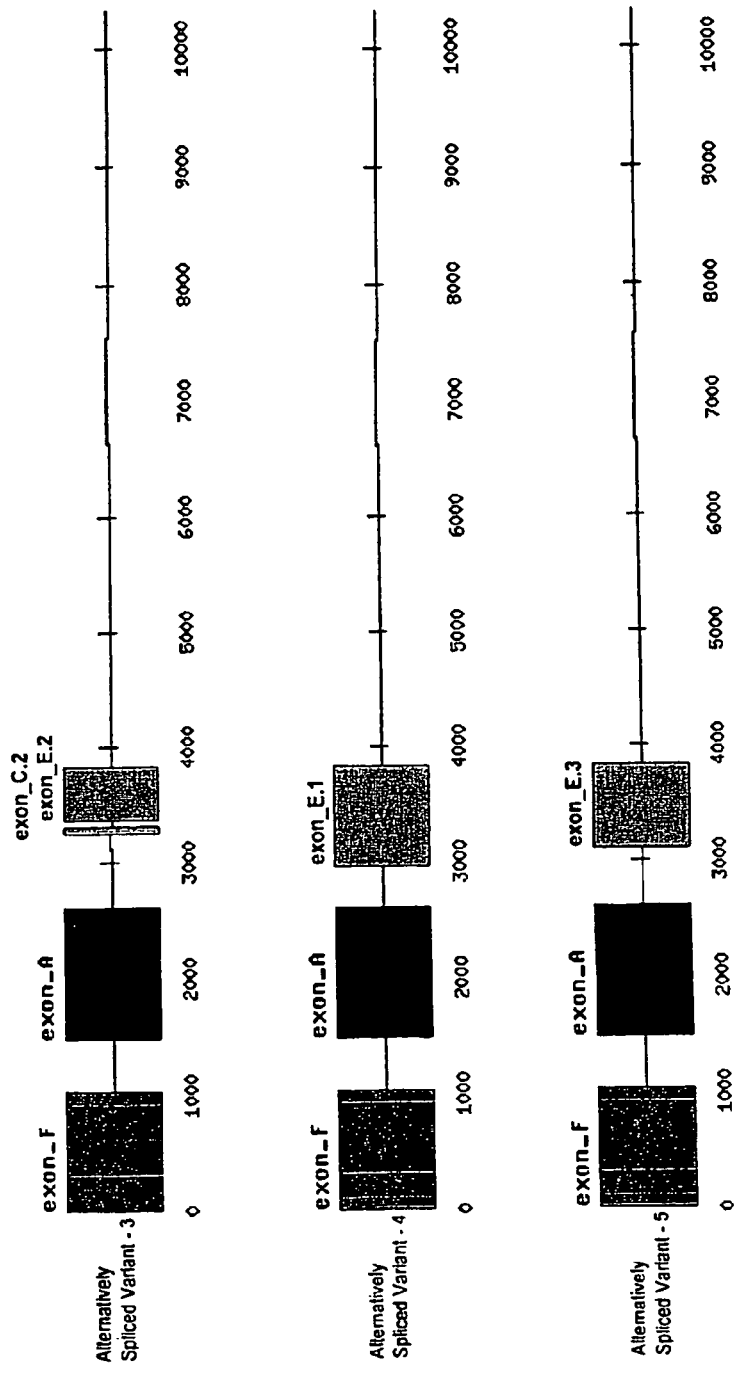

FIGS. 8A-8B illustrate the five different transcripts of Gene 214 and show the genomic structure of the gene. The exons are shown to scale and the SNPs are identified by their location along the genomic BAC DNA (SEQ ID NO:1).

J. Restriction Fragment Length Polymorphism (RFLP Assay) and Allele Specific Oligonucleotide Analysis (ASO Assay)

To identify other individuals with the polymorphisms listed in Table 5, RFLP assay and ASA were performed.

1. RFLP Assay. The amplicon, containing the polymorphism, was PCR amplified using primers that were used to generate a fragment for sequencing (sequencing primers) or re-arrayed into 384 well microtitre plates using a Tecan Genesis RSP200. The amplified products were loaded onto 2% agarose gels and size fractionated at 150V for 5 minutes. The DNA was transferred from the gel to Hybond N+ nylon membrane (Amersham-Pharmacia) using a Vacuum blotter (Bio-Rad). The filter containing the blotted PCR products was transferred to a dish containing 300 mls of pre-hybridization solution (5×SSPE {pH7.4}, 2% SDS, 5×Denhardts). The filter was left in the pre-hybridization solution at 40° C. for >1 hour. After pre-hybridization, 10 mls of the pre-hybridization solution and the filter were transferred to a washed glass bottle. The allele specific oligonucleotides (ASO) were designed with the polymorphism in the middle. The size of the oligonucleotide was dependent upon the GC content of the sequence around the polymorphism. Those ASOs that had a G or C polymorphism were designed so that the Tm was between 54-56° C. and those that had an A or T variance were designed so that the Tm was between 60-64° C. All oligonucleotides were phosphate free at the 5' end and purchased from Gibco BRL. For each polymorphism 2 ASOs were designed: one for each variant.

The two ASOs that represented the polymorphism were resuspended at a concentration of 1 μg/μl and separately end-labeled with γ-ATP$^{32}$ (6000 Ci/mmol) (NEN) using T4 polynucleotide kinase according to manufacturer recommendations (NEB). The end-labeled products were removed from the unincorporated γ-ATP$^{32}$ by passing the reactions through Sephadex G-25 columns according to manufacturers recommendation (Amersham-Pharmacia). The entire end-labeled product of one ASO was added to the bottle containing the appropriate filter and 10 mls of hybridization solution. The hybridization reaction was placed in a rotisserie oven (Hybaid) and left at 40° C. for a minimum of 4 hours. The other ASO was stored at −20° C.

After the prerequisite hybridization time had elapsed, the filter was removed from the bottle and transferred to 1 liter of wash solution (0.1×SSPE {pH7.4}, 0.1% SDS) pre-warmed to 45° C. After 15 minutes the filter was transferred to another liter of wash solution (0.1×SSPE {pH7.4}, 0.1% SDS) pre-warmed to 50° C. After 15 minutes the filter was wrapped in Saran, placed in an autoradiograph cassette and an X-ray film (Kodak) placed on top of the filter. Depending on the efficiency of the end-labeling reaction of the ASO and its hybridization to the filter an image would be observed on the film within an hour. After an image had been captured on film for the 50° C. wash, the process was repeated for wash steps at 55° C., 60° C. and 65° C. The image that captured the best result was used.

The ASO was removed from the filter by adding 1 liter of boiling strip solution (0.1×SSPE {pH7.4}, 0.1% SDS). This was repeated two more times. After removing the ASO the filter was pre-hybridized in 300 mls of pre-hybridization solution (5×SSPE {pH7.4}, 2% SDS, 5×Denhardts) at 40° C. for >1 hour. The second end-labeled ASO corresponding to the other variant was removed from storage at −20° C. and thawed to room temperature. The filter was placed into a glass bottle along with 10 mls of hybridization solution and the entire end-labeled product of the second ASO. The hybridization reaction was placed in a rotisserie oven (Hybaid) and left at 40° C. for a minimum of 4 hours. After the hybridization, the filter was washed at various temperatures and images captured on film as described above.

The two films that best captured the allele specific assay with the two ASOs were converted into digital images by scanning them into Adobe Photo Shop. These images were overlaid against each other in Graphic Converter and then scored and stored in FileMaker Pro 4.0.

K. Association Study Analysis

In order to determine whether mutations in candidate genes are responsible for the asthma phenotype, association studies are performed using a case-control study design. To avoid issues of population admixture which can bias case-control studies, the unaffected controls were collected in both the US and the UK. A total of three hundred controls were collected, 200 in the UK and 100 in the US. Inclusion into the study required that the control individual was negative for asthma, as determined by self report of never having asthma, has no first degree relatives with asthma, and was negative for eczema and symptoms indicative of atopy within the past 12 months. Data from an abbreviated questionnaire similar to that administered to the affected sib pair families were collected. Results from skin prick tests to 4 common allergens were also collected. The results of the skin prick test were used to select a subset of control that were most likely to be asthma and atopy negative.

A subset of unrelated cases are selected from the affected sib pair families based on the evidence for linkage at the chromosomal location of interest. One affected sib from families demonstrating identity-by-decent (IBD) at the appropriate marker loci is selected. In the selection criteria, preference is given to families with multiple affected sibs all of whom are concordant at the marker locus as well as to families where affected and unaffected sibs are discordant.

For each polymorphism, the frequency of the alleles in the control and case populations is compared using a Fisher exact test. It is expected that a mutation increasing susceptibility to the disease would be more prevalent in the cases than in the controls, while a protective mutation should be more prevalent in the control group. Similarly, the genotype frequencies of the SNPs are compared between cases and controls. P-values are computed for both the allele and genotype frequencies. A small p-value is indicative of an association between the SNPs and the disease phenotype. The analysis is repeated for the US and UK population separately, to adjust for the possibility of genetic heterogeneity.

1. Association Test with Individual SNPs

Statistical analyses for the two SNPs in Gene 214 are presented in Table 8. Column one list the exon containing the SNP of interest. The control ("CNTL") allele frequency and sample size ("N") are in columns two and three. The affected individuals ("CASE") allele frequency and sample size ("N") are listed in columns four and five. The sixth column contains the significance value level of comparison between the control allele frequencies and the case allele frequencies. The SNP in Exon C had allelic frequencies significantly different in the cases versus the controls in the US and combined samples. In the Combined and US population, this SNP was more frequent in the cases (4.1% and 10.4%, respectively) than in the control population (0.8% and 1.3%), and the differences were statistically significance (p=0.0099 and p=0.0083). This analysis suggests that Gene 214, is, at least partially responsible for the asthmatic phenotype in those families linked to the chromosome 12 region.

TABLE 8

| EXON | Frequencies | | | | ALLELE |
|------|------|-----|------|-----|---------|
|  | CNTL | N | CASE | N | P-VALUE |
| Combined sample | | | | | |
| B | 17.8% | 214 | 20.3% | 111 | 0.4577 |
| C | 0.8% | 194 | 4.1% | 97 | 0.0083 |
| U.S. sample | | | | | |
| B | 15.1% | 76 | 16.7% | 24 | 0.8204 |
| C | 1.3% | 75 | 10.4% | 24 | 0.0099 |
| UK sample | | | | | |
| B | 19.2% | 138 | 21.3% | 87 | 0.6291 |
| C | 0.4% | 119 | 2.1% | 73 | 0.1559 |

II. Preparation of Nucleic Acids, Vectors, Transformations and Host Cells

The nucleic acids of this invention can be produced in large quantities by replication in a suitable host cell. Natural or synthetic nucleic acid fragments, comprising at least ten contiguous bases coding for a desired peptide or polypeptide can be incorporated into recombinant nucleic acid constructs, usually DNA constructs, capable of introduction into and replication in a prokaryotic or eukaryotic cell. Usually the nucleic acid constructs will be suitable for replication in a unicellular host, such as yeast or bacteria, but may also be intended for introduction to (with and without integration within the genome) cultured mammalian or plant or other eukaryotic cells, cell lines, tissues, or organisms. The purification of nucleic acids produced by the methods of the present invention is described, for example, in Sambrook et al, *Molecular Cloning. A Laboratory Manual,* 2nd Ed. (Cold Spring Harbor Laboratory, Cold Spring Harbor, N.Y. (1989) or Ausubel et al, *Current Protocols in Molecular Biology,* J. Wiley and Sons, NY (1992).

The nucleic acids of the present invention can also be produced by chemical synthesis, e.g., by the phosphoramidite method described by Beaucage et al, *Tetra. Letts.,* 22:1859-1862 (1981) or the triester method according to Matteucci, et al, *J. Am. Chem. Soc.,* 103:3185 (1981), and can performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

These nucleic acids can encode full-length variant forms of proteins as well as the naturally-occurring protein. The variant proteins (which could be especially useful for detection and treatment of disorders) can have the variant amino acid sequences encoded by the polymorphisms described in Table 5, when said polymorphisms are read so as to be in-frame with the full-length coding sequence of which it is a component.

Nucleic acid constructs prepared for introduction into a prokaryotic or eukaryotic host will comprise a replication system recognized by the host, including the intended nucleic acid fragment encoding the selected protein or polypeptide, and will preferably also include transcription and translational initiation regulatory sequences operably linked to the protein encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals are also included, where appropriate, whether from a native Gene 214 protein or from other receptors or from secreted proteins of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al, *Molecular Cloning. A Laboratory Manual,* 2nd Ed. (Cold Spring Harbor Laboratory, Cold Spring Harbor, N.Y. (1989) or Ausubel et al, *Current Protocols in Molecular Biology,* J. Wiley and Sons, NY (1992).

An appropriate promoter and other necessary vector sequences will be selected so as to be functional in the host, and will include, when appropriate, those naturally associated with Gene 214 gene. Examples of workable combinations of cell lines and expression vectors are described in Sambrook et al, *Molecular Cloning. A Laboratory Manual,* 2nd Ed. (Cold Spring Harbor Laboratory, Cold Spring Harbor, N.Y. (1989) or Ausubel et al, *Current Protocols in Molecular Biology,* J. Wiley and Sons, NY (1992). Many useful vectors are known in the art and can be obtained from such vendors as Stratagene (supra), New England BioLabs, Beverly, Mass., U.S.A, Promega Biotech, and other biotechnology product suppliers. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in EP 73,675A. Appropriate non-native mammalian promoters might include the early and late promoters from SV40 (Fiers et al, *Nature,* 273:113 (1978)) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al, *FEBS Letts.* 241:119 (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the nucleic acids into the host cell by any method known in the art, including those described above, will be referred to herein as "transformation." The cells into which have been introduced nucleic acids described above are meant to also include the progeny of such cells.

Large quantities of the nucleic acids and proteins of the present invention may be prepared by expressing the Gene 214 nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.),

*Cell Culture. Methods in Enzymology*, volume 58, Academic Press, Inc., Harcourt Brace Jovanovich, N.Y., (1979)). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the nucleic acids of the present invention will be useful not only for the production of the nucleic acids and proteins of the present invention, but also, for example, in studying the characteristics of Gene 214 proteins.

Antisense nucleic acid sequences are useful in preventing or diminishing the expression of Gene 214 gene, as will be appreciated by one skilled in the art. For example, nucleic acid vectors containing all or a fragment Gene 214 gene, complementary sequences of the former, or other sequences from the 12q23-qter region may be placed under the control of a promoter in an antisense orientation and introduced into a cell. Such fragments can be 16 or more nucleotides in length. Expression of such an antisense construct within a cell will interfere with Gene 214 transcription and/or translation and/or replication.

The probes and primers based on the Gene 214 gene sequences disclosed herein are used to identify homologous Gene 214 gene sequences and proteins in other species. These Gene 214 gene sequences and proteins are used in the diagnostic/prognostic, therapeutic and drug screening methods described herein for the species from which they have been isolated.

III. Protein Expression and Purification

Expression and purification of the Gene 214 protein of the invention can be performed essentially as outlined below. To facilitate the cloning, expression and purification of membrane and secreted protein from the 12q23-qter, a gene expression system, such as the pET System (Novagen), for cloning and expression of recombinant proteins in *E. coli* is selected. Also, a DNA sequence encoding a peptide tag, the His-Tap, is fused to the 3' end of DNA sequences of interest to facilitate purification of the recombinant protein products. The 3' end is selected for fusion to avoid alteration of any 5' terminal signal sequence.

Nucleic acids chosen, for example, from the nucleic acids set forth SEQ ID NO:2, SEQ ID NO:4, SEQ ID NO:6, SEQ ID NO: 8, and SEQ ID NO:10, or SEQ ID NO:1 for cloning the genes are prepared by polymerase chain reaction (PCR). Synthetic oligonucleotide primers specific for the 5' and 3' ends of the nucleotide sequences are designed and purchased from Life Technologies (Gaithersburg, Md.). All forward primers (specific for the 5' end of the sequence) are designed to include an NcoI cloning site at the 5' terminus. These primers are designed to permit initiation of protein translation at the methionine residue encoded within the NcoI site followed by a valine residue and the protein encoded by the DNA sequence. All reverse primers (specific for the 3' end of the sequence) include an EcoRI site at the 5' terminus to permit cloning of the sequence into the reading frame of the pET-28b. The pET-28b vector provides a sequence encoding an additional 20 carboxyl-terminal amino acids including six histidine residues (at the C-terminus), which comprise the histidine affinity tag.

DNA prepared from the 12q23-qter region is used as the source of template DNA for PCR amplification (Ausubel et al, *Current Protocols in Molecular Biology*, John Wilty & Sons (1994)). To amplify a DNA sequence containing the nucleotide sequence, c DNA (50 ng) is introduced into a reaction vial containing 2 mM $MgCl_2$, 1 micromolar synthetic oligonucleotide primers (forward and reverse primers) complementary to and flanking a defined 12q23-qter region, 0.2 mM of each of deoxynucleotide triphosphate, dATP, dGTP, dCTP, dTTP and 2.5 units of heat stable DNA polymerase (Amplitaq, Roche Molecular Systems, Inc., Branchburg, N.J.) in a final volume of 100 microliters.

Upon completion of thermal cycling reactions, each sample of amplified DNA is purified using the Qiaquick Spin PCR purification kit (Qiagen, Gaithersburg, Md.). All amplified DNA samples are subjected to digestion with the restriction endonucleases, e.g., NcoI and EcoRI (New England BioLabs, Beverly, Mass., U.S.A.) (Ausubel et al, *Current Protocols in Molecular Biology*, John Wiley & Sons, Inc. (1994)). DNA samples are then subjected to electrophoresis on 1.0% NuSeive (FMC BioProducts, Rockland, Me.) agarose gels. DNA is visualized by exposure to ethidium bromide and long wave UV irradiation. DNA contained in slices isolated from the agarose gel are purified using the Bio 101 GeneClean Kit protocol (Bio 101, Vista, Calif.).

The pET-28b vector is prepared for cloning by digestion with restriction endonucleases, e.g., NcoI and EcoPJ (New England BioLabs, Beverly, Mass.) (Ausubel et al, *Current Protocols in Molecular Biology*, John Wiley & Sons, Inc. (1994)). The pET-28a vector, which encodes the histidine affinity tag that can be fused to the 5' end of an inserted gene, is prepared by digestion with appropriate restriction endonucleases.

Following digestion, DNA inserts are cloned (Ausubel et al, *Current Protocols in Molecular Biology*, John Wiley & Sons, Inc. (1994)) into the previously digested pET-28b expression vector. Products of the ligation reaction are then used to transform the BL21 strain of *E. coli* (Ausubel et al, *Current Protocols in Molecular Biology*, John Wiley & Sons, Inc. (1994)) as described below.

Competent bacteria, E. coli strain BL21 or *E. coli* strain BL21 (DE3), are transformed with recombinant pET expression plasmids carrying the cloned sequence according to standard methods (Ausubel et al, *Current Protocols in Molecular Biology*, John Wiley & Sons, Inc. (1994)). Briefly, 1 microliter of ligation reaction is mixed with 50 microliters of electrocompetent cells and subjected to a high voltage pulse, after which samples were incubated in 0.45 ml SOC medium (0.5% yeast extract, 2.0% tryptone, 10 mM NaCl, 2.5 mM KCl, 10 mM $MgCl_2$, 10 mM $MgSO_4$ and 20 mM glucose) at 37° C. with shaking for 1 hour. Samples are then spread on LB agar plates containing 25 μg/ml kanamycin sulfate for growth overnight. Transformed colonies of BL21 are then picked and analyzed to evaluate cloned inserts, as described below.

Individual BL21 clones transformed with recombinant pET-28b 12q23-qter region nucleotide sequences are analyzed by PCR amplification of the cloned inserts using the same forward and reverse primers specific for the 12q23-qter region sequences that are used in the original PCR amplification cloning reactions. Successful amplification verifies the integration of the sequence in the expresssion vector (Ausubel et al, *Current Protocols in Molecular Biology*, John Wiley & Sons, Inc. (1994)).

Individual clones of recombinant pET-28b vectors carrying properly cloned 12q23-qter region nucleotide sequences are picked and incubated in 5 ml of LB broth plus 25 μg/ml-kanamycin sulfate overnight. The following day plasmid DNA is isolated and purified using the Qiagen plasmid purification protocol (Qiagen Inc., Chatsworth, Calif.).

The pET vector can be propagated in any *E. coli* K-12 strain, e.g., HMS174, HB101, JM109, DH5 and the like, for purposes of cloning or plasmid preparation. Hosts for expression include *E. coli* strains containing a chromosomal copy of the gene for T7 RNA polymerase. These hosts are lysogens of bacteriophage DE3, a lambda derivative that carries the lad gene, the lacUV5 promoter and the gene for T7 RNA polymerase. T7

RNA polymerase is induced by addition of isopropyl-β-D-thiogalactoside (IPTG), and the T7 RNA polymerase transcribes any target plasmid containing a functional T7 promoter, such as pET-28b, carrying its gene of interest. Strains include, for example, BL21(DE3) (Studier et al, *Meth. Enzymol.*, 185:60-89 (1990)). To express the recombinant sequence, 50 ng of plasmid DNA are isolated as described above to transform competent BL21(DE3) bacteria as described above (provided by Novagen as part of the pET expression kit). The lacZ gene (β-galactosidase) is expressed in the pET-System as described for the 12q23-qter region recombinant constructions. Transformed cells were cultured in SOC medium for 1 hour, and the culture is then plated on LB plates containing 25 μg/mlkanamycin sulfate. The following day, the bacterial colonies are pooled and grown in LB medium containing kanamycin sulfate (25 μg/ml) to an optical density at 600 nM of 0.5 to 1.0 O.D. units, at which point 1 mM IPTG was added to the culture for 3 hours to induce gene expression of the 12q23-qter region recombinant DNA constructions.

After induction of gene expression with IPTG, bacteria are collected by centrifugation in a Sorvall RC-3B centrifuge at 3500×g for 15 minutes at 4° C. Pellets are resuspended in 50 ml of cold mM Tris-HCl, pH 8.0, 0.1 M NaCl and 0.1 mM EDTA (STE buffer). Cells are then centrifuged at 2000×g for 20 minutes at 4° C. Wet pellets are weighed and frozen at −80° C. until ready for protein purification.

A variety of methodologies known in the art can be used to purify the isolated proteins (Coligan et al, *Current Protocols in Protein Science*, John Wiley & Sons (1995)). For example, the frozen cells can be thawed, resuspended in buffer and ruptured by several passages through a small volume microfluidizer (Model M-110S, Microfluidics International Corp., Newton, Mass.). The resultant homogenate is centrifuged to yield a clear supernatant (crude extract) and, following filtration, the crude extract is fractioned over columns. Fractions are monitored by absorbance at $OD_{280}$ nm and peak fractions may be analyzed by SDS-PAGE.

The concentrations of purified protein preparations are quantified spectrophotometrically using absorbance coefficients calculated from amino acid content (Perkins, *Eur. J. Biochem.*, 157:169-180 (1986)). Protein concentrations are also measured by the method of Bradford, *Anal. Biochem.*, 72:248-254 (1976) and Lowry et al, *J. Biol. Chem.*, 193:265-275 (1951) using bovine serum albumin as a standard.

SDS-polyacrylamide gels of various concentrations are purchased from BioRad (Hercules, Calif.), and stained with Coomassie blue. Molecular weight markers may include rabbit skeletal muscle myosin (200 kDa), *E. coli* β-galactosidase (116 kDa), rabbit muscle phosphorylase B (97.4 kDa), bovine serum albumin (66.2 kDa), ovalbumin (45 kDa), bovine carbonic anyhdrase (31 kDa), soybean trypsin inhibitor (21.5 kDa), egg white lysozyme (14.4 kDa) and bovine aprotinin (6.5 kDa).

Proteins can also be isolated by other conventional means of protein biochemistry and purification to obtain a substantially pure product, i.e., 80, 95, or 99% free of cell component contaminants, as described in Jacoby, *Methods in Enzymology*, Vol. 104, Academic Press, New York (1984); Scoopes, *Protein Purification, Principles and Practice*, $2^{nd}$ Ed., Springer-Verlag, New York (1987); and Deutscher (ed.), *Guide to Protein Purification, Methods in Enzymology*, Vol. 182 (1990). If the protein is secreted, it can be isolated from the supernatant in which the host cell is grown; otherwise, it can be isolated from a lysate of the host cells.

Once a sufficient quantity of the desired protein has been obtained, it may be used for various purposes. One use of the protein or polypeptide is the production of antibodies specific for binding. These antibodies may be either polyclonal or monoclonal, and may be produced by in vitro or in vivo techniques well known in the art. Monoclonal antibodies to epitopes of any of the peptides identified and isolated as described can be prepared from murine hybridomas (Kohler, *Nature*, 256:495 (1975)). In summary, a mouse is inoculated with a few micrograms of protein over a period of two weeks. The mouse is then sacrificed. The cells that produce antibodies are then removed from the mouse's spleen. The spleen cells are then fused with polyethylene glycol with mouse myeloma cells. The successfully fused cells are diluted in a microtiter plate and growth of the culture is continued. The amount of antibody per well is measured by immunoassay methods such as ELISA (Engvall, *Meth. Enzymol.*, 70:419 (1980)). Clones producing antibody can be expanded and further propagated to produce protein antibodies. Other suitable techniques involve in vitro exposure of lymphocytes to the antigenic polypeptides, or alternatively, to selection of libraries of antibodies in phage or similar vectors. See Huse et al, *Science*, 246:1275-1281 (1989). For additional information on antibody production see Davis et al, *Basic Methods in Molecular Biology*, Elsevier, N.Y., Section 21-2 (1989). Such antibodies are particularly useful in diagnostic assays for detection of variant protein forms, or as an active ingredient in a pharmaceutical composition.

III. Transformed Hosts, Development of Pharmaceuticals and Research Tools

Cells and animals that carry Gene 214 can be used as model systems to study and test for substances that have potential as therapeutic agents. The cells are typically cultured mesenchymal stem cells. These may be isolated from individuals with somatic or germline Gene 214. Alternatively, the cell line can be engineered to carry the Gene 214, as described above. After a test substance is applied to the cells, the transformed phenotype of the cell is determined. Any trait of transformed cells can be assessed, including respiratory diseases including asthma, atopy, and response to application of putative therapeutic agents.

IV. Diagnostic Applications

As discussed herein, chromosomal region 12q23-qter has been genetically linked to a variety of diseases and disorders. This invention provides nucleic acids and SNPs which can be useful in diagnosing individuals with chromosomal abnormalities linked to these diseases.

Antibody-based diagnostic methods: The invention provides methods for detecting disease-associated antigenic components in a biological sample, which methods comprise the steps of: (i) contacting a sample suspected to contain a disease-associated antigenic component with an antibody specific for an disease-associated antigen, extracellular or intracellular, under conditions in which a stable antigen-antibody complex can form between the antibody and disease-associated antigenic components in the sample; and (ii) detecting any antigen-antibody complex formed in step (i) using any suitable means known in the art, wherein the detection of a complex indicates the presence of disease-associated antigenic components in the sample. It will be understood that assays that utilize antibodies directed against sequences previously unidentified, or previously unidentified as being disease-associated, which sequences are disclosed herein, are within the scope of the invention.

Many immunoassay formats are known in the art, and the particular format used is determined by the desired application. An immunoassay can use, for example, a monoclonal antibody directed against a single disease-associated epitope, a combination of monoclonal antibodies directed against different epitopes of a single disease-associated antigenic component, monoclonal antibodies directed towards epitopes of different disease-associated antigens, polyclonal antibodies directed towards the same disease-associated antigen, or polyclonal antibodies directed towards different disease-associated antigens. Protocols can also, for example, use solid supports, or may involve immunoprecipitation. Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

Kits suitable for antibody-based diagnostic applications typically include one or more of the following components:
  (i) Antibodies: The antibodies can be pre-labeled; alternatively, the antibody may be unlabeled and the ingredients for labeling can be included in the kit in separate containers, or a secondary, labeled antibody is provided; and
  (ii) Reaction components: The kit can also contain other suitably packaged reagents and materials needed for the particular immunoassay protocol, including solid-phase matrices, if applicable, and standards.

The kits referred to above can include instructions for conducting the test. Furthermore, in preferred embodiments, the diagnostic kits are adaptable to high-throughput and/or automated operation.

Nucleic-acid-based diagnostic methods: The invention provides methods for detecting disease-associated nucleic acids in a sample, such as in a biological sample, which methods comprise the steps of: (i) contacting a sample suspected to contain a disease-associated nucleic acid with one or more disease-associated nucleic acid probes under conditions in which hybrids can form between any of the probes and disease-associated nucleic acid in the sample; and (ii) detecting any hybrids formed in step (i) using any suitable means known in the art, wherein the detection of hybrids indicates the presence of the disease-associated nucleic acid in the sample. To detect disease-associated nucleic acids present in low levels in biological samples, it may be necessary to amplify the disease-associated sequences or the hybridization signal as part of the diagnostic assay. Techniques for amplification are known to those of skill in the art.

Disease-associated nucleic acids useful as probes in diagnostic methods include oligonucleotides at least about 15 nucleotides in length, preferably at least about 20 nucleotides in length, and most preferably at least about 25-55 nucleotides in length, that hybridize specifically with one or more disease-associated nucleic acids.

A sample to be analyzed, such as, for example, a tissue sample, may be contacted directly with the nucleic acid probes. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without size separation.

Kits suitable for nucleic acid-based diagnostic applications typically include the following components:
  (i) Probe DNA: The probe DNA may be prelabeled; alternatively, the probe DNA may be unlabeled and the ingredients for labeling may be included in the kit in separate containers; and
  (ii) Hybridization reagents: The kit may also contain other suitably packaged reagents and materials necessary or desirable for the particular hybridization protocol, including solid-phase matrices, if applicable, and standards.

In cases where a disease condition is suspected to involve an alteration of the disease gene, specific oligonucleotides may be constructed and used to assess the level of disease mRNA in cells affected or other tissue affected by the disease.

For example, to test whether a person has a disease gene, polymerase chain reaction can be used. In order to identify an individual who possesses the disease gene or the wild type copy, two oligonucleotides are synthesized by standard methods or are obtained from a commercial supplier of custom-made oligonucleotides. The length and base composition are determined by standard criteria using the Oligo 4.0 primer Picking program (Wojchich Rychlik, 1992). One of the oligonucleotides is designed so that it will hybridize only to the disease gene DNA under the PCR conditions used. The other oligonucleotide is designed to hybridize to a segment of genomic DNA, wild type or non disease gene such that amplification of DNA using these oligonucleotide primers produces a conveniently identified DNA fragment. Tissue samples may be obtained from hair follicles, whole blood, or the buccal cavity. The DNA fragment generated by this procedure is sequenced by standard techniques.

Other amplification techniques besides PCR may be used as alternatives, such as ligation-mediated PCR or techniques involving Q-beta replicase (Cahill et al, *Clin. Chem.*, 37(9): 1482-5 (1991)). Products of amplification can be detected by agarose gel electrophoresis, quantitative hybridization, or equivalent techniques for nucleic acid detection known to one skilled in the art of molecular biology (Sambrook et al, *Molecular Cloning: A Laboratory Manual*, Cold Spring Harbor Laboratory, Cold Spring, N.Y. (1989)). Other alterations in the disease gene may be diagnosed by the same type of amplification-detection procedures, by using oligonucleotides designed to identify those alterations.

V. Genomic Screening

The use of polymorphic genetic markers linked to the Gene 214 gene is very useful in predicting susceptibility to the diseases genetical linked to 12q23-qter. Similarly, as provided in Table 5 the identification of polymorphic genetic markers within the Gene 214 gene will allow the identification of specific allelic variants that are in linkage disequilibrium with other genetic lesions that affect one of the disease states discussed herein including respiratory disorders and obesity. SSCP allows the identification of polymorphisms within the genomic and coding region of the disclosed gene.

Table 3 provides primers which one skilled in the art could identify exons which contain SNP's. Table 4 provides primers to identify the sequence change. This information can assist one skilled in the art to identify additional SNP's for use in genomic screening. This method has been used successfully by others skilled in the art (e.g., Sheffield et al, *Genet.*, 4:1837-1844 (1995); LeBlanc-Straceski et al, *Genomics*, 19:341-9 (1994); Chen et al, *Genomics*, 25:1-8 (1995)). Use of these reagents with populations or individuals will predict their risk for diseases or disorders described herein, especially respiratory disorders and obesity.

VI. Treatment of Disorders

Thus, the present invention provides methods of screening for drugs comprising contacting such an agent with a novel protein of this invention or fragment thereof and assaying (i) for the presence of a complex between the agent and the protein or fragment, or (ii) for the presence of a complex between the protein or fragment and a ligand, by methods well known in the art. In such competitive binding assays the novel protein or fragment is typically labeled. Free protein or fragment is separated from that present in a protein:protein complex, and the amount of free (i.e., uncomplexed) label is a measure of the binding of the agent being tested to the novel protein or its interference with protein ligand binding, respectively.

This invention also contemplates the use of competitive drug screening assays in which neutralizing antibodies capable of specifically binding the Gene 214 protein compete with a test compound for binding to the Gene 214 protein or fragments thereof. In this manner, the antibodies can be used to detect the presence of any peptide which shares one or more antigenic determinants of a Gene 214 protein.

The goal of rational drug design is to produce structural analogs of biologically active proteins of interest or of small molecules with which they interact (e.g., agonists, antagonists, inhibitors) in order to fashion drugs which are, for example, more active or stable forms of the protein, or which, e.g., enhance or interfere with the function of a protein in vivo. See, e.g., Hodgson, *Bio/Technology*, 9:19-21 (1991). In one approach, one first determines the three-dimensional structure of a protein of interest or, for example, of the Gene 214 receptor or ligand complex, by x-ray crystallography, by computer modeling or most typically, by a combination of approaches. Less often, useful information regarding the structure of a protein may be gained by modeling based on the structure of homologous proteins. An example of rational drug design is the development of HIV protease inhibitors (Erickson et al, *Science*, 249:527-533 (1990)). In addition, peptides (e.g., Gene 214 protein) are analyzed by an alanine scan (Wells, *Methods in Enzymol.*, 202:390-411 (1991)). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved Gene 214 proteinactivity or stability or which act as inhibitors, agonists, antagonists, etc. of Gene 214 proteinactivity. By virtue of the availability of cloned Gene 214 gene sequences, sufficient amounts of the Gene 214 protein may be made available to perform such analytical studies as x-ray crystallography. In addition, the knowledge of the Gene 214 protein sequence will guide those employing computer modeling techniques in place of, or in addition to x-ray crystallography.

Cells and animals that carry the Gene 214 gene or an analog thereof can be used as model systems to study and test for substances that have potential as therapeutic agents. After a test substance is applied to the cells, the transformed phenotype of the cell is determined.

The therapeutic agents and compositions of the present invention are useful for preventing or treating respiratory disease. Pharmaceutical formulations suitable for therapy comprise the active agent in conjunction with one or more biologically acceptable carriers. Suitable biologically acceptable carriers include, but are not limited to, phosphate-buffered saline, saline, deionized water, or the like. Preferred biologically acceptable carriers are physiologically or pharmaceutically acceptable carriers.

The compositions include an effective amount of active agent. Effective amounts are those quantities of the active agents of the present invention that afford prophyladic protection against a respiratory disease, or which result in amelioration or cure of an existing respiratory disease. Prophylactic methods incorporate a prophylactically effective amount of an active agent or composition. A prophylactically effective amount is an amount effective to prevent disease. Treatment methods incorporate a therapeutically effective amount of an active agent or composition. A therapeutically effective amount is an amount sufficient to ameliorate or eliminate the symptoms of disease. The effective amount will depend upon the agent, the severity of disease and the nature of the disease, and the particular host. The amount can be determined by experimentation known in the art, such as by establishing a matrix of dosage amounts and frequencies of dosage administration and comparing a group of experimental units or subjects to each point in the matrix. The prophylactically and/or therapeutically effective amounts can be administered in one administration or over repeated administrations. Therapeutic administration can be followed by prophylactic administration, once initial clinical symptoms of disease have been resolved.

The agents and compositions can be administered topically or systemically. Systemic administration includes both oral and parental routes. Parental routes include, without limitation, subcutaneous, intramuscular, intraperitoneal, intravenous, transdermal, and intranasal administration.

VII. Gene Therapy

In recent years, significant technological advances have been made in the area of gene therapy for both genetic and acquired diseases. (Kay et al, *Proc. Natl. Acad. Sci. USA*, 94:12744-12746 (1997)) Gene therapy can be defined as the deliberate transfer of DNA for therapeutic purposes. Improvement in gene transfer methods has allowed for development of gene therapy protocols for the treatment of diverse types of diseases. Gene therapy has also taken advantage of recent advances in the identification of new therapeutic genes, improvement in both viral and nonviral gene delivery systems, better understanding of gene regulation, and improvement in cell isolation and transplantation. Gene therapy would be carried out according to generally accepted methods as described by, for example, Friedman, *Therapy for Genetic Diseases*, Friedman, Ed., Oxford University Press, pages 105-121 (1991).

Vectors for introduction of genes both for recombination and for extrachromosomal maintenance are known in the art, and any suitable vector may be used. Methods for introducing DNA into cells such as electroporation, calcium phosphate co-precipitation, and viral transduction are known in the art, and the choice of method is within the competence of one skilled in the art (Robbins, Ed., *Gene Therapy Protocols*, Human Press, NJ (1997)). Cells transformed with a Gene 214 gene can be used as model systems to study chromosome 12 disorders and to identify drug treatments for the treatment of such disorders.

Gene transfer systems known in the art may be useful in the practice of the gene therapy methods of the present invention. These include viral and nonviral transfer methods. A number of viruses have been used as gene transfer vectors, including polyoma, i.e., SV40 (Madzak et al, *J. Gen. Virol.*, 73:1533-1536 (1992)), adenovirus (Berkner, *Curr. Top. Microbiol. Immunol.*, 158:39-61 (1992); Berkner et al, *Bio Techniques*, 6:616-629 (1988); Gorziglia et al, *J. Virol.*, 66:4407-4412 (1992); Quantin et al, *Proc. Natl. Acad. Sci. USA*, 89:2581-2584 (1992); Rosenfeld et al, *Cell*, 68:143-155 (1992); Wilkinson et al, *Nucl. Acids Res.*, 20:2233-2239 (1992); Stratford-Perricaudet et al, *Hum. Gene Ther.*, 1:241-256 (1990)), vaccinia virus (Mackett et al, *Biotechnology*, 24:495-499 (1992)), adeno-associated virus (Muzyczka, *Curr. Top. Microbiol. Immunol.*, 158:91-123 (1992); Ohi et al, *Gene*, 89:279-282 (1990)), herpes viruses including HSV and EBV (Margolskee, *Curr. Top. Microbiol. Immunol.*, 158:67-90 (1992); Johnson et al, *J. Virol.*, 66:2952-2965 (1992); Fink et al, *Hum. Gene Ther.*, 3:11-19 (1992); Breakfield et al, *Mol. Neurobiol.*, 1:337-371 (1987;) Fresse et al, *Biochem. Pharmacol.*, 40:2189-2199 (1990)), and retroviruses of avian (Brandyopadhyay et al, *Mol. Cell. Biol.*, 4:749-754 (1984); Petropouplos et al, *J. Virol.*, 66:3391-3397 (1992)), murine (Miller, *Curr. Top. Microbiol. Immunol.*, 158:1-24 (1992); Miller et al, *Mol. Cell. Biol.*, 5:431-437 (1985); Sorge et al, *Mol. Cell. Biol.*, 4:1730-1737 (1984); Mann et al, . *Virol.*, 54:401-407 (1985)), and human origin (Page et al, *J. Virol.*, 64:5370-5276 (1990); Buchschalcher et al, *J. Virol.*, 66:2731-2739 (1992)). Most human gene therapy protocols have been based on disabled murine retroviruses.

Nonviral gene transfer methods known in the art include chemical techniques such as calcium phosphate coprecipitation (Graham et al, *Virology*, 52:456-467 (1973); Pellicer et al, *Science*, 209:1414-1422 (1980)), mechanical techniques, for example microinjection (Anderson et al, *Proc. Natl. Acad. Sci. USA*, 77:5399-5403 (1980); Gordon et al, *Proc. Natl. Acad. Sci. USA*, 77:7380-7384 (1980); Brinster et al, *Cell*, 27:223-231 (1981); Constantini et al, *Nature*, 294:92-94 (1981)), membrane fusion-mediated transfer via liposomes (Felgner et al, *Proc. Natl. Acad. Sci. USA*, 84:7413-7417 (1987); Wang et al, *Biochemistry*, 28:9508-9514 (1989); Kaneda et al, *J. Biol. Chem.*, 264:12126-12129 (1989); Stewart et al, *Hum. Gene Ther.*, 3:267-275 (1992); Nabel et al, *Science*, 249:1285-1288 (1990); Lim et al, *Circulation*, 83:2007-2011 (1992)), and direct DNA uptake and receptor-mediated DNA transfer (Wolff et al, *Science*, 247:1465-1468 (1990); Wu et al, *BioTechniques*, 11:474-485 (1991); Zenke et al, *Proc. Natl. Acad. Sci. USA*, 87:3655-3659 (1990); Wu et al, *J. Biol. Chem.*, 264:16985-16987 (1989); Wolff et al, *Bio-Techniques*, 11:474-485 (1991); Wagner et al, 1990; Wagner et al, *Proc. Natl. Acad. Sci. USA*, 88:4255-4259 (1991); Cotten et al, *Proc. Natl. Acad. Sci. USA*, 87:4033-4037 (1990); Curiel et al, *Proc. Natl. Acad. Sci. USA*, 88:8850-8854 (1991); Curiel et al, *Hum. Gene Ther.*, 3:147-154 (1991)).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is non-specific, localized in vivo uptake and expression have been reported in tumor deposits, for example, following direct in situ administration (Nabel, *Hum. Gene Ther.*, 3:399-410 (1992)).

VIII. Transgenic Animals

This invention further relates to nonhuman transgenic animals capable of expressing an exogenous or non-naturally occurring variant Gene 214 gene. Such a transgenic animal can also have one or more endogenous genes inactivated or can, instead of expressing an exogenous variant gene, have one or more endogenous analogs inactivated. Any nonhuman animal can be used; however typical animals are rodents, such as mice, rats, or guinea pigs.

Animals for testing therapeutic agents can be selected after treatment of germline cells or zygotes. Thus, expression of an exogenous Gene 214 gene or a variant can be achieved by operably linking the gene to a promoter and optionally an enhancer, and then microinjecting the construct into a zygote. See, e.g., Hogan, et al., *Manipulating the Mouse Embryo, A Laboratory Manual*, Cold Spring Harbor Laboratory, Cold Spring Harbor, N.Y. Such treatments include insertion of the exogenous gene and disrupted homologous genes. Alternatively, the gene(s) of the animals may be disrupted by insertion or deletion mutation of other genetic alterations using conventional techniques, such as those described by, for example, Capecchi, *Science*, 244:1288 (1989); Valancuis et al, *Mol. Cell. Biol.*, 11:1402 (1991); Hasty et al, *Nature*, 350:243 (1991); Shinkai et al, *Cell*, 68:855 (1992); Mombaerts et al, *Cell*, 68:869 (1992); Philpott et al, *Science*, 256: 1448 (1992); Snouwaert et al, *Science*, 257:1083 (1992); Donehower et al, *Nature*, 356:215 (1992). After test substances have been administered to the animals, modulation of the disorder must be assessed. If the test substance reduces the incidence of the disorder, then the test substance is a candidate therapeutic agent. These animal models provide an extremely important vehicle for potential therapeutic products.

The disclosure of each of the patents, patent applications and publications cited in the specification is hereby incorporated by reference herein in its entirety.

Although the invention has been set forth in detail, one skilled in the art will recognize that numerous changes and modifications can be made, and that such changes and modifications may be made without departing from the spirit and scope of the invention.

The invention claimed is:

1. An isolated antibody or epitope-binding fragment thereof which specifically binds to a polypeptide comprising the amino acid sequence set forth in SEQ ID NO:11 wherein the specific binding is to the SEQ ID NO:11 portion of the polypeptide.

2. The isolated antibody or epitope-binding fragment of claim 1, which binds to an immunogenic component comprising at least 30 consecutive amino acid residues of SEQ ID NO:11.

3. The isolated antibody or epitope-binding fragment of claim 1, which binds to an immunogenic component comprising at least 50 consecutive amino acid residues of SEQ ID NO:11.

4. The isolated antibody or epitope-binding fragment of claim 1, which binds to an immunogenic component comprising at least 100 consecutive amino acid residues of SEQ ID NO:11.

5. The isolated antibody or epitope-binding fragment of claim 1 which binds to a polypeptide having an amino acid sequence of at least 200 consecutive residues of SEQ ID NO:11 or an immunogenic component thereof.

6. The isolated antibody or epitope-binding fragment of claim 1, which is immobilized on a solid support.

7. The isolated antibody or epitope-binding fragment of claim 1, which binds to a polypeptide having an amino acid sequence of SEQ ID NO: 11.

8. The isolated antibody or epitope-binding fragment of claim 1 which is a monoclonal antibody.

9. The isolated antibody or epitope-binding fragment of claim 1 which is a polyclonal antibody.

10. The isolated antibody or epitope-binding fragment of claim 1 which is a recombinant antibody.

11. The isolated antibody or epitope-binding fragment of claim 1 which is a chimeric antibody.

12. The isolated antibody or epitope-binding fragment of claim 1 which is a humanized antibody.

13. The isolated antibody or epitope-binding fragment of claim 1 bound to said polypeptide.

14. A composition comprising the isolated antibody or epitope-binding fragment of claim 1 and a pharmaceutically acceptable carrier.

15. An isolated antibody or epitope-binding fragment thereof which specifically binds to a polypeptide comprising the an amino acid sequence encoded by 50 or more consecutive nucleotides of SEQ ID NO:10 wherein the specific binding is to the amino acid sequence encoded by 50 or more consecutive nucleotides of SEQ ID NO:10 portion of the polypeptide.

16. The isolated antibody or epitope-binding fragment of claim 15, which binds to an immunogenic component comprising at least 30 amino acid residues encoded by consecutive nucleotides of SEQ ID NO:10.

17. The isolated antibody or epitope-binding fragment of claim 15, which binds to an immunogenic component comprising at least 50 amino acid residues encoded by consecutive nucleotides of SEQ ID NO:10.

18. The isolated antibody or epitope-binding fragment of claim 15, which binds to an immunogenic component comprising at least 100 amino acid residues encoded by consecutive nucleotides of SEQ ID NO:10.

19. The isolated antibody or epitope-binding fragment of claim 15, which is immobilized on a solid support.

20. The isolated antibody or epitope-binding fragment of claim 15 which is a monoclonal antibody.

21. The isolated antibody or epitope-binding fragment of claim 15 which is a polyclonal antibody.

22. The isolated antibody or epitope-binding fragment of claim 15 which is a recombinant antibody.

23. The isolated antibody or epitope-binding fragment of claim 15 which is a chimeric antibody.

24. The isolated antibody or epitope-binding fragment of claim 15 which is a humanized antibody.

25. The isolated antibody or epitope-binding fragment of claim 15 bound to said polypeptide.

26. A composition comprising the isolated antibody or epitope-binding fragment of claim 15 and a pharmaceutically acceptable carrier.

* * * * *

SEQUENCE LISTING

```
<160> NUMBER OF SEQ ID NOS: 51

<210> SEQ ID NO 1
<211> LENGTH: 10304
<212> TYPE: DNA
<213> ORGANISM: Homo sapiens
<220> FEATURE:
```

```
<221> NAME/KEY: modified_base
<222> LOCATION: (267)
<223> OTHER INFORMATION: a, t, c or g

<400> SEQUENCE: 1
cgggcgtgta tatctcttca tagagagcgc tcagacagcg tgcgttaatc tgcgtcgata      60
tatagagatc tttatcactg agtagataga acgtacatga atgtacgaac agtccagacg     120
agtaacttga ctaggataag atagacagta ccaactaatg agacaagaag agggaatcat     180
atagaatcat gtagtctgag tctagcgagt gtcgacatga tcacaagcga aatacagact     240
atgagaagag gtagaaataa taagtanact gagaagagag gtcatatgta catacaaatc     300
agtaaagcaa tagaaattga atacattata agccacagtt acagaattag cctaatttaa     360
caaccatggc aagcgagtta tatcaaacat agaagagtaa actctatcga ccatgggtag     420
gaacgaataa aggcgtcgag aagacaataa gaatgcgtgt taaacagcaa tacaagagaa     480
tagcaccact gaagcagacc aaaggcgtca ccggggaagt agggaagagg cacctcacaa     540
ggagaggaaa gggcagtcct gattttgaaa atttcagtga aaagacagtg ttgttcccgg     600
aggcagctta gtgatcccgc atcgactctg aagaggaccc tgagggtagg ggattttttgg     660 gcctgaccgg cctatgctga acgcccaccg ggaattcagg gagaaacacg gggccccggc     720
ttccaggaga gcagccaggc cacagccctg aggacgggca aacccaccc aggcacggtg     780 agagggaggc cgcccaggcc tggggcctgg cggcagggga tgaagtggac cagagccccg     840
caaatcctaa cgtgggtgag cagtgagcct gtgtggctgc gagtggctcc gttttgggc     900 tgtttgttcc tgcagcaaat gatgccagcc ctgacggaac cagtgcacgt ccaccacgag     960
ctgcccacgt cctctccagg aagggacccg ggtccacgag ctgccacgt cctctccagg    1020 aagggaccga agaccacgag ctgccacgc cctctccagg aggggacacc gggttcacga    1080 gctgccacg tcctctccag gaggggacac cgggttcatg agctgccac gcccttcca    1140 ggaagggacc ccgggttcac gagctgccca cgtcctctcc aggagggggac accgggttca    1200 cgagctgccc acgtcctctc caggaaggga cccaggtcca cgaactgccc acgccctctc    1260
caggagggga cccgggtcca cgagctgccc acgtcgtctc caggaaggga cccgggtcca    1320
cgagctgccc acgtcctctc caggaaggga cccgggtcca cgagctgccc acgtcctctc    1380
caggaaggga ccccgggttc acgagctgcc acgtcctct ccaggaaggg accccgggtt    1440
cacgagctgc ccacgtcctc tccaggaggg accccgggt tcacgagctg cccacgtcct    1500
ctccaggaag gaccccggg ttcacgagct gcccacgtcg tctccaggaa gggacccggg    1560
tccacgagct gcccacgtcc tctccaggaa agacccggg tccacgagct ggccacgtcc    1620
tctgcaggaa gggaccccgg gtccacgagc tgcccacgtc ctctccagga agggaccccg    1680
ggttcacgag ctgcccacgt cctctccagg aagggacccc gggtccacga gctgcccacg    1740
tcctctccag gaagggaccc cggtccacg aactgcccac gtcctctcca ggaagggacc    1800
ccgggttcac gagctgccca cgtcctctcc aggagggggac accgggttca cgagctgccc    1860
acgccctctc aggaaggga ccccgggttc atgagctgcc acgtcctct ccaggaaggg    1920 acccgggtcc acgaactgcc cacgccctct ccaggagggg acccgggtcc acgagctgcc    1980
cacgtcgtca acgggaaggg accccgggtcc acgagctgcc cacgtcctct ccaggaaggg    2040
acccgggtcc acgaactgcc cacgcgctct ccaggagggg acaccgggtt cacgagctgc    2100
ccacgccctc tccaggaagg gaccccgggt tcacgagctg cccacgtcct ctccaggagg    2160
ggacaccggg ttcacgagct gcccacgtcc tctccaggag gggacaccgg gttcacgagc    2220
```

```
tgcccacgcc ctctccagga ggggacaccg ggttcacgag ctgcccacgt cctctccagg    2280
aagggacccg ggtccacgag ctgcccacgt cctctccagg aggggacacc gggttcacga    2340
gctgcccacg cactttccag gaagggaccc cgggttcagg tctcctgccg gcccacatcg    2400
tgcctttgtg taaatcagaa gaaagatgag gaacaggccc tcctctctct ccaggcaggc    2460
tttggtggag gggctggatc tcctgccgca ccttccctgg cagggcaccc tgtgcttgag    2520
ccccagaact gcaggcggcc ggcagagaag gggtccatga tggcgcctcg gtgcgcagcc    2580
ttggacctgc ccccatggac ctgggtgagg acttcccagc ccttccccgg ctccagctgc    2640
tctccctaag ccgcctcacc ccttcctcgg gcagggggca gtggacgagg gttccgtccc    2700
tccaggggat gctcccaaac ccctgccagg acttggcaga tccggcctct catcttggca    2760
gctagatggt gggacgggat catcgtggtg gctttaattt gcatttctct gatgactgat    2820
gatttcgagc atctcttcat atgtttgctg gctttgggga tagagatatt tcttcctaaa    2880
gcaaaacttg attatgtcat ttctgcttca agatgccagt gatgcctgag gtctgcaggg    2940
cagtgcatac gctcaccgcc tggccgctca ggagcctgtg cttgacccccc aaatccgccc    3000 cccaactccc tgttaccggc tcactccttc catgaggggc cttccccagg acagccgat     3060 gctctcctga tggctcctgc ccttgcagag tgctgccccc gcctgccac ctggcctgga     3120 ccctcgcctg agcccctca gggctctgcg ccacctcaac ccaggcgttt gttccgcagg     3180
aacctcccgg ctcttcccac tcgggaaagg aaggctctgg gcatggaggt cggccaggcc    3240
ccatccccgt accctggccc ttcttcctgc ttcctgtttg tcactgcccc ggggcctttg    3300
cacctgcatt ccctctctct gtgagtgtcc tggggcccgt tacccacgtc accgtcccag    3360
gatacctttt cttttctttc tctctctcca gctttattga ggtatagttg acaattcagg    3420
acggtgtgca ctcaaggtat gcagcatcac aacctgacac acgtaggcat tgtgaaatga    3480
gtcccacaat tgggctaatt aacacaccca tcaccttaca tggttacttc tttctgtggt    3540
gagaacacta aattttaaat agaggacaca cagcctgggc aacatagtga gaccctgtct    3600
ctacaaatat aaaaaaatta tctggacgtg gtggtgcaca cctgtggtcc cagctacttg    3660
ggaagctgag gctggagaat cacttgagcc tgggaggcgg aggttgcggt gcactccagc    3720
ctgggcgaca gagggaggcc ctatctcaaa ataaataaat aaaggacaca ttcttatcag    3780
ctgtagtcac cacgttcatt acatcttaga acccgctaat ctcataactg cacctttgtt    3840
ccctgtgacc ctcaactccc ggtcccctcc agccctgaca gccactgttc actctgcttc    3900
tgtgagttcc gcttttcac acgtcactcg agtgaggcca tgtgctgttt gtctttctgt     3960
gcctggctta tctcacttac cacaaatgcc cttcaggttc atcgtgtcct cacaaatggc    4020
gggcttgccc tgcccctgccc tgccctgccc tcccttccct tcccttctct ctctctcctt    4080
tctctctctc tggctctctc tctctcccac ccttccctttt ccctcctgtg gaataacact   4140
cctgtgtgtg tgtgcatgca tgtgtgtgta tatttctcac atattttcat tcatgcatcc   4200
gttgatggac acttgggttg attccgtgtc ctggctgctg ggacagtgct gcgatgaaca   4260
cgagggtaca gacgcctctc ctacacgcta atttcaactc tttggatata cacccagcag   4320
tgggattgct ggatcaggtg ggagctctat ttccacattt ttgaggaacc tccctgccgt   4380
ctcccatggt ggctgtgcca acgacgttcc cagggacaga gtgcaacggg cccctttcct   4440
ccatgtcctc gccaacactc gctatctttt gcgttttgat gacagtcatc caataggtg    4500 ccagttggta cctcctgtgg ttttttatttg attttcctga tgattagtga tgctggacgt   4560
tatttcgtct acacttcggc cacttacatg ttttccttcg agacacgcag attcaggtcc   4620
```

```
tttgcacgtt ttaaaatttt ttttgtttgt ttttgttatt gagttgaatt ccttctacaa   4680
tttgcaaatt aactcctcat catatacatg gattgcaaat accccgcct ccccctgggg    4740 ttttgccttt tcactgcaaa tactcccgcc tccccatggg ggttgccttt tcctgccaa    4800 tacccccacc tccccatggg ggttgccttt tcctgcaaa taccccacc tccccgtggg    4860 ttctgccttt tccctgccaa taccccgcc tccccctggg ggttgccttt tcactctgtt    4920
ggtttccttt gcggaagctt tctggtttgt tgcactctca ctgtctattt ttgcttctgt   4980
tgcctgtgct tgtggggcca tattttaaaa aaatcattgc ccggaccagc ctcaagaagt   5040
tttcctccta cgttttcttc taagagtttt atggtgtcgg gtcttaggtt tgaatcttta   5100
atccgtgttg agttgatttt cgtaggtggt gtcggatgag gcccttttcat cctcctccac  5160 ttttcccagc accacctatt gaggatgccc ctttccccgt cgtgtgtcct tggcgccttt   5220
gctgaaggtc agttggccgt aactgtgcat ggggaccctt cctggccccc ctggtgccct   5280 gtgcccata tgtcccaccc cctcccttac tttttctcca tggcatgaat cacccccagac 5340 ctactataca aaatttatcc tatttatttt tatttattta tttatttttg agatggagtc   5400
tcactctgtc acccaggctg gagtgcagtg gcacgatctc ggctcactgc aagctccgcc   5460
tcccaggttc acgccattct cctgcctcag cctcccaagt agctgggatt acgggcgccc   5520
gccaccatgc ccggctaaat ttttttgtttt tttcgtagag acagagtttc cctatgttgc   5580
ccccaggttg gtctcgaact cctgggctca agtaatcctt ccacttcggc ctcccaaagt   5640
gctgggatta caggcatgag ccattcggcc cggcctattt ttttttttttc agacagagtt  5700 tcactcttgt cacccaggct gaaatgcatt gcaatgatct tggctcactg caacttccac  5760
ctcccaggtt caaggatttt tctggcctc agcctcccga ggagctggga ttacagtgtg   5820
caaccaccac accgggctaa aattttttgga atttttttttt tttactagag acagggttca  5880
acaatgctgg tcaggctggt ctcgaattcc tgacctcaag tgatcctccc acctcggcct   5940
cccaaagtgc tgggattaca ggcgtgagcc gccatgcctg gccatggata ttgtaaatgt   6000
tcttgtttgt tgtatgttttt cctcactggg ctgtgcactc ctgagggcgg ggcatctgtc  6060
ccattcttca gtgctgggtc ccctgtgtct gggacagtgt atacatacag caggtgcata  6120
atcagtcttg actggaaggg tgagggagtc aacgcacatg gcagtcattg gactatgtgt   6180
ctgagaagca taactcactt aatcttgaag ttcacttatg gattgaagtg tgcggttcag  6240
tgacttttaa tatatttacc gagttgtgta accatcacca ccatctaatt ttaaatcatt   6300
ttcatcatcc ctaaaagaaa cttcagaccc actagctgtc cctcccccta ttcctcccac  6360
cccagccctg gtcctggccg caggctgctc acctgcatct ctctgtggat ctgccggttg   6420
tggacatttc acacacctgc gtgcagtctt ctgtgcctgc ctctttcact cgctgtgatg  6480
tttaagttca cccatgttgt catctatatc ggtacttact tccttttttt ttttggagat   6540
gaagtcttgc tcttgtcacc caggctggag tgcagtggcg tgatctcggc tcacagcaac   6600
ttctgcctct ggggttcaag tgattctcct gccttagcct cccaagtagc tgggactaca   6660
ggtttgcacc accatgtcct gctaattttt ttttttttgt attttttaata gagacagggt   6720 ttctcctcat tggccaggct ggtctcgaac tcctgacctc agacgatcca cctgcctcag  6780
cctcccgaag tgtgggatt acaggcacga gccactgtgc ccggccatca ttccttttta   6840
ctgctgacta atagtctgct gtgtgaatcc accgctagaa acccactcat cagttgatgg  6900
tcatgtgggt tgcttctgct attcgcttat tatgaacagt gctggaataa acgttcctgt   6960
gcactcttgg gcatacgcct aggagtggaa ctgctgggtc aaatggtgac tttacgttta   7020
```

```
acgttctgag gagccgccag gcgttttaac acagtgactg caccatttca cattcctgcc    7080
aacaatgtgt gagaattcca atttctctac atccccaaca ttttcctttA aaaaaaagaa    7140
aaaagaaaca tagccatcta agtggatgtg gagcagactg tccctctggt ttgggtttgc    7200
gttgctttta tggctcatga tgtctgagtc tctctccatg tgctcatggg gattcgtata    7260
tctactttgg gaaatgctta ttcaagtcct ttgtccacat ttgactgggt tgcttgtctt    7320
tttatttcat ttactacgat gacagcccct acatggaagg attttgtttt tgtaatccca    7380
ttacccgag gtgagaatga attgccagtt gctcaaggcc ttcagctctt agggaggagc     7440
ctggacctgg agctgctccg ggctctggca aagctccaat cccggcctca gtccttgagg    7500
cctggtcctc acccagcttt ctccttccac cgtgccatgg aggaagcccg acctccctgc    7560
acggctggcc tggggttgtt cacgactgag tccaggtgtc cccagaacgg atgtcactgg    7620
tcacagtgtt cctggtaata ggtgaccccA ggcacagggt gttcctgatc ataggtaacc    7680
caggcacagt gtcccagtc acaggtgtct ccaggcacag gtgtcccag tcacaggtgt     7740
cccaggtcac aggcgtcccc aggcacaggt gtccctggtc acagatgtcc ccaggcacag    7800
gtgtcccagg cacaggtgtc tccaggcaca ggcgtcccag gtcacaggtg tccccggtca    7860
caggtgtccc tggtcacagg tgtctccagg cacaggtgtc cctggtcaca ggtgtccccg    7920
gtcacaggtg tccaggtca caggtgtccc caggcacagg tgtccccggt cacaggtgtc     7980
tccggtcaca ggtgtcccca ggcataggtg tccctggtca caggcaccca tggtcacagg    8040
tgtccccagg cacaggtgtc ctggtcacag gtgtccagt cacagctgtc cccggtcaca    8100
ggtgtctcca ggcacaggtg ttcccggtca caggtgtccc caggcacagg tgtcccggtc    8160
acaggtgtcc ccaggcacag gagttcctgg tcacaggtgt ccccaggcac aggcagccac    8220
aggaagccga tgcatggaac agagagaaac agagacacaa agaaaagaga gtgagagaca    8280
gaagaaatgg gaaacagaaa tggttggaga aaagcatcca gtagacatga atagagagga    8340
agaggaggag ggggacgggc agcagagacc cagggaggct gcagtgcctg gacccctcac    8400
cacactttcc attctgccct tcctggggaa gacttccaga aaagtgggcc aggctgaggg    8460
gacgatgagg acacagaggc cccagggag ggagggagga gcgggccacc cggaggggct    8520
gtggtcagct caaagcctct ggagtcaagg ataaatcctc tgacctttga cctccgacct    8580
ccctctcctt ggctccaggc tccccacaca gctttccatg accaaatctt acaggaagct    8640
gaagggcagt ccggtgaggg tctgtaagtc accgccaggg cacagaacgg aggttggcag    8700
gggaggagag acccctgggc tgccgtctgc cttcaccctg cacatcaggc ctgtgtgggg    8760
gtgtcaccat ccttcactcc ctggcatctg atccaagatt acgcctggca gggcctctcc    8820
tctgggatta gctccgggaa agctcccatc agtgaaggga ggggctcagg ctctgtgcac    8880
acaggggtgc ccccttccag ggagggagca gctctcccac atggcagaac actcatttcc    8940
tgtcagtgct ctcctgagca cacaaggatt aaactgagca gcaagcactc caggtggccg    9000
agaggccctg ggggatgggc ccttgccct ggcctccct gcaaggcagc tcccgccccg     9060
gggccctgcc tctgagagcg aggtgtgcag gctcttccta tgggctacct ggcccatccc    9120
cagaacggcc tgcactgtcc ctccccgacc tgcacccaga catggacact caccctcccc    9180
aaccctgag acattcaggt ccacactggg gcctgggccc cctcaagttg catggggact     9240
ggggtgcctt ggcgcctctt ctgtgagtat tcctacacac agagcctgct tcctctccaa    9300
cctgcaccta aacatggaca ctcaccatcc ccaaccccg agactttcag gtccacactg     9360
gggcctgggc cccctcaagt tgcatgggga ctgggctgcc tcggcgcctc ttctgtgagt    9420
```

-continued

```
gttcctacac acagagcctg cctcctgtcc gggtgatgtt gggtcgtcct ccgcctctgg    9480
gagcacctgc aggggctgtt gctctgggct ccctggagat gcaagccccc gggcctgcct    9540
gcttgttatg tgtgtattca ttaagcccat gccagcgggg gtctccgcaa gaaacaggca    9600
cagtgctgtg aggggctaa tgaggcctga tttctccagg ggcaggcagg acgggagccc    9660
atgagggttg ctgaggaccc agggatgtgc actgtgggaa gccaccacca cccagaagcc    9720
ggcaagggca aggagaagt tagtggtgcc agaacatggc taaacgaggc agccatggaa     9780
aggggatgca gacaggaagt ggagaggaag gcggttctcc aggagcccta ggacctgctc    9840
tggggctgct gctgctgagc ccaactggga accagagcac aggataatgg tgacactggt    9900
gatgatggcg atggagatga ttatgatggt gatgatgatg gtgatggtgg tgatgatggt    9960
gatgatgatg gtgacggtgg tgatggtgat ggtgatgatg gtgatgatgg tgacggtggt   10020
gatggtgctg atgatgatgg tgatgctgat ggtgatggtg acggtgatga tgatggtgac   10080
ggtgatgatg gtgatgatgg tgatggtgat gctgatggtg gtggtggtga tgatggtggt   10140
gatgatgatg atgatgatgg tgatgatggt gatgctgatg gtgatgatgg tgatggtgat   10200
catggtgatg atgatggtga tggtgatgat gatgatggtg atggtggtga tgatggtgat   10260
ggtgatgatg atgatggtga tggtgatgtc ttcaccacgg ggcg                     10304
```

<210> SEQ ID NO 2
<211> LENGTH: 1581
<212> TYPE: DNA
<213> ORGANISM: Homo sapiens
<220> FEATURE:
<221> NAME/KEY: CDS
<222> LOCATION: (3)..(1307)

<400> SEQUENCE: 2

```
tc acg agc tgc cca cgt cct ctc cag gaa ggg acc ccg ggt tca cga         47
   Thr Ser Cys Pro Arg Pro Leu Gln Glu Gly Thr Pro Gly Ser Arg
   1               5                   10                  15 gct gcc cac gtc gtc tcc agg aag gga ccc ggg tcc acg agc tgc cca        95
Ala Ala His Val Val Ser Arg Lys Gly Pro Gly Ser Thr Ser Cys Pro
                20                  25                  30 cgt cct ctc cag gaa agg acc cgg gtc cac gag ctg gcc acg tcc tct       143
Arg Pro Leu Gln Glu Arg Thr Arg Val His Glu Leu Ala Thr Ser Ser
            35                  40                  45 gca gga agg gac ccc ggg tcc acg agc tgc cca cgt cct ctc cag gaa       191
Ala Gly Arg Asp Pro Gly Ser Thr Ser Cys Pro Arg Pro Leu Gln Glu
        50                  55                  60 ggg acc ccg ggt tca cga gct gcc cac gtc ctc tcc agg aag gga ccc       239
Gly Thr Pro Gly Ser Arg Ala Ala His Val Leu Ser Arg Lys Gly Pro
    65                  70                  75 cgg gtc cac gag ctg ccc acg tcc tct cca gga agg gac ccc ggg tcc       287
Arg Val His Glu Leu Pro Thr Ser Ser Pro Gly Arg Asp Pro Gly Ser
80                  85                  90                  95 acg aac tgc cca cgt cct ctc cag gaa ggg acc ccg ggt tca cga gct       335
Thr Asn Cys Pro Arg Pro Leu Gln Glu Gly Thr Pro Gly Ser Arg Ala
                100                 105                 110 gcc cac gtc ctc tcc agg agg gga cac cgg gtt cac gag ctg ccc acg       383
Ala His Val Leu Ser Arg Arg Gly His Arg Val His Glu Leu Pro Thr
            115                 120                 125 ccc tct cca gga agg gac ccc ggg ttc atg agc tgc cca cgt cct ctc       431
Pro Ser Pro Gly Arg Asp Pro Gly Phe Met Ser Cys Pro Arg Pro Leu
        130                 135                 140 cag gaa ggg acc cgg gtc cac gaa ctg ccc acg ccc tct cca gga ggg       479
Gln Glu Gly Thr Arg Val His Glu Leu Pro Thr Pro Ser Pro Gly Gly
    145                 150                 155
```

```
gac ccg ggt cca cga gct gcc cac gtc gtc aac ggg aag gga ccc ggg       527
Asp Pro Gly Pro Arg Ala Ala His Val Val Asn Gly Lys Gly Pro Gly
160             165                 170                 175 tcc acg agc tgc cca cgt cct ctc cag gaa ggg acc cgg gtc cac gaa       575
Ser Thr Ser Cys Pro Arg Pro Leu Gln Glu Gly Thr Arg Val His Glu
                180                 185                 190 ctg ccc acg cgc tct cca gga ggg gac acc ggg ttc acg agc tgc cca       623
Leu Pro Thr Arg Ser Pro Gly Gly Asp Thr Gly Phe Thr Ser Cys Pro
        195                 200                 205 cgc cct ctc cag gaa ggg acc ccg ggt tca cga gct gcc cac gtc ctc       671
Arg Pro Leu Gln Glu Gly Thr Pro Gly Ser Arg Ala Ala His Val Leu
210                 215                 220 tcc agg agg gga cac cgg gtt cac gag ctg ccc acg tcc tct cca gga       719
Ser Arg Arg Gly His Arg Val His Glu Leu Pro Thr Ser Ser Pro Gly
225                 230                 235 ggg gac acc ggg ttc acg agc tgc cca cgc cct ctc cag gag ggg aca       767
Gly Asp Thr Gly Phe Thr Ser Cys Pro Arg Pro Leu Gln Glu Gly Thr
240                 245                 250                 255 ccg ggt tca cga gct gcc cac gtc ctc tcc agg aag gga ccc ggg tcc       815
Pro Gly Ser Arg Ala Ala His Val Leu Ser Arg Lys Gly Pro Gly Ser
                260                 265                 270 acg agc tgc cca cgt cct ctc cag gag ggg aca ccg ggt tca cga gct       863
Thr Ser Cys Pro Arg Pro Leu Gln Glu Gly Thr Pro Gly Ser Arg Ala
        275                 280                 285 gcc cac gca ctt tcc agg aag gga ccc cgg gtt cag gtc tcc tgc cgg       911
Ala His Ala Leu Ser Arg Lys Gly Pro Arg Val Gln Val Ser Cys Arg
290                 295                 300 ccc aca tcg tgc ctt tgt gta aat cag aag aaa gat gag gaa cag gcc       959
Pro Thr Ser Cys Leu Cys Val Asn Gln Lys Lys Asp Glu Glu Gln Ala
305                 310                 315 ctc ctc tct ctc cag gca ggc ttt ggt gga ggg gct gga tct cct gcc      1007
Leu Leu Ser Leu Gln Ala Gly Phe Gly Gly Gly Ala Gly Ser Pro Ala
320                 325                 330                 335 gca cct tcc ctg gca ggg cac cct gtg ctt gag ccc cag aac tgc agg      1055
Ala Pro Ser Leu Ala Gly His Pro Val Leu Glu Pro Gln Asn Cys Arg
                340                 345                 350 cgg ccg gca gag aag ggg tcc atg atg gcg cct cgg tgc gca gcc ttg      1103
Arg Pro Ala Glu Lys Gly Ser Met Met Ala Pro Arg Cys Ala Ala Leu
        355                 360                 365 gac ctg ccc cca tgg acc tgg gaa cct ccc ggc tct tcc cac tcg gga      1151
Asp Leu Pro Pro Trp Thr Trp Glu Pro Pro Gly Ser Ser His Ser Gly
370                 375                 380 aag gaa ggc tct ggg cat gga ggt cgg cca ggc ccc atc ccc gta ccc      1199
Lys Glu Gly Ser Gly His Gly Gly Arg Pro Gly Pro Ile Pro Val Pro
385                 390                 395 tgg ccc ttc ttc ctg ctt cct gtt tgt cac tgc ccc ggg gcc ttt gca      1247
Trp Pro Phe Phe Leu Leu Pro Val Cys His Cys Pro Gly Ala Phe Ala
400                 405                 410                 415 cct gca ttc cct ctc tct aga cag ggt ttc tcc tca ttg gcc agg ctg      1295
Pro Ala Phe Pro Leu Ser Arg Gln Gly Phe Ser Ser Leu Ala Arg Leu
                420                 425                 430 gtc tcg aac tcc tgacctcaga cgatccacct gcctcagcct cccgaagtgt          1347
Val Ser Asn Ser
            435 tgggattaca ggcacgagcc actgtgcccg gccatcattc cttttttactg ctgactaata   1407 gtctgctgtg tgaatccacc gctagaaacc cactcatcag ttgatggtca tgtgggttgc   1467 ttctgctatt cgcttattat gaacagtgct ggaataaacg ttcctgtgca ctcttgggca   1527 tacgcctagg agtggaactg ctgggtcaaa aaaaaaaaaa aaaaaaaaaa aaaa         1581
```

<210> SEQ ID NO 3
<211> LENGTH: 435
<212> TYPE: PRT
<213> ORGANISM: Homo sapiens

<400> SEQUENCE: 3

```
Thr Ser Cys Pro Arg Pro Leu Gln Glu Gly Thr Pro Gly Ser Arg Ala
  1               5                  10                  15

Ala His Val Val Ser Arg Lys Gly Pro Gly Ser Thr Ser Cys Pro Arg
                 20                  25                  30

Pro Leu Gln Glu Arg Thr Arg Val His Glu Leu Ala Thr Ser Ser Ala
             35                  40                  45

Gly Arg Asp Pro Gly Ser Thr Ser Cys Pro Arg Pro Leu Gln Glu Gly
         50                  55                  60

Thr Pro Gly Ser Arg Ala Ala His Val Leu Ser Arg Lys Gly Pro Arg
 65                  70                  75                  80

Val His Glu Leu Pro Thr Ser Ser Pro Gly Arg Asp Pro Gly Ser Thr
                 85                  90                  95

Asn Cys Pro Arg Pro Leu Gln Glu Gly Thr Pro Gly Ser Arg Ala Ala
                100                 105                 110

His Val Leu Ser Arg Arg Gly His Arg Val His Glu Leu Pro Thr Pro
            115                 120                 125

Ser Pro Gly Arg Asp Pro Gly Phe Met Ser Cys Pro Arg Pro Leu Gln
        130                 135                 140

Glu Gly Thr Arg Val His Glu Leu Pro Thr Pro Ser Pro Gly Gly Asp
145                 150                 155                 160

Pro Gly Pro Arg Ala Ala His Val Val Asn Gly Lys Gly Pro Gly Ser
                165                 170                 175

Thr Ser Cys Pro Arg Pro Leu Gln Glu Gly Thr Arg Val His Glu Leu
            180                 185                 190

Pro Thr Arg Ser Pro Gly Gly Asp Thr Gly Phe Thr Ser Cys Pro Arg
        195                 200                 205

Pro Leu Gln Glu Gly Thr Pro Gly Ser Arg Ala Ala His Val Leu Ser
210                 215                 220

Arg Arg Gly His Arg Val His Glu Leu Pro Thr Ser Ser Pro Gly Gly
225                 230                 235                 240

Asp Thr Gly Phe Thr Ser Cys Pro Arg Pro Leu Gln Glu Gly Thr Pro
                245                 250                 255

Gly Ser Arg Ala Ala His Val Leu Ser Arg Lys Gly Pro Gly Ser Thr
            260                 265                 270

Ser Cys Pro Arg Pro Leu Gln Glu Gly Thr Pro Gly Ser Arg Ala Ala
        275                 280                 285

His Ala Leu Ser Arg Lys Gly Pro Arg Val Gln Val Ser Cys Arg Pro
    290                 295                 300

Thr Ser Cys Leu Cys Val Asn Gln Lys Lys Asp Glu Glu Gln Ala Leu
305                 310                 315                 320

Leu Ser Leu Gln Ala Gly Phe Gly Gly Ala Gly Ser Pro Ala Ala
                325                 330                 335

Pro Ser Leu Ala Gly His Pro Val Leu Glu Pro Gln Asn Cys Arg Arg
            340                 345                 350

Pro Ala Glu Lys Gly Ser Met Met Ala Pro Arg Cys Ala Ala Leu Asp
        355                 360                 365

Leu Pro Pro Trp Thr Trp Glu Pro Pro Gly Ser Ser His Ser Gly Lys
    370                 375                 380
```

```
Glu Gly Ser Gly His Gly Gly Arg Pro Gly Pro Ile Pro Val Pro Trp
385                 390                 395                 400

Pro Phe Phe Leu Leu Pro Val Cys His Cys Pro Gly Ala Phe Ala Pro
            405                 410                 415

Ala Phe Pro Leu Ser Arg Gln Gly Phe Ser Ser Leu Ala Arg Leu Val
        420                 425                 430

Ser Asn Ser
        435

<210> SEQ ID NO 4
<211> LENGTH: 1441
<212> TYPE: DNA
<213> ORGANISM: Homo sapiens
<220> FEATURE:
<221> NAME/KEY: CDS
<222> LOCATION: (3)..(1166)

<400> SEQUENCE: 4 tc acg agc tgc cca cgt cct ctc cag gaa ggg acc ccg ggt tca cga         47
   Thr Ser Cys Pro Arg Pro Leu Gln Glu Gly Thr Pro Gly Ser Arg
    1               5                  10                  15 gct gcc cac gtc gtc tcc agg aag gga ccc ggg tcc acg agc tgc cca        95
Ala Ala His Val Val Ser Arg Lys Gly Pro Gly Ser Thr Ser Cys Pro
                 20                  25                  30 cgt cct ctc cag gaa agg acc cgg gtc cac gag ctg gcc acg tcc tct       143
Arg Pro Leu Gln Glu Arg Thr Arg Val His Glu Leu Ala Thr Ser Ser
             35                  40                  45 gca gga agg gac ccc ggg tcc acg agc tgc cca cgt cct ctc cag gaa       191
Ala Gly Arg Asp Pro Gly Ser Thr Ser Cys Pro Arg Pro Leu Gln Glu
         50                  55                  60 ggg acc ccg ggt tca cga gct gcc cac gtc ctc tcc agg aag gga ccc       239
Gly Thr Pro Gly Ser Arg Ala Ala His Val Leu Ser Arg Lys Gly Pro
 65                  70                  75 cgg gtc cac gag ctg ccc acg tcc tct cca gga agg gac ccc ggg tcc       287
Arg Val His Glu Leu Pro Thr Ser Ser Pro Gly Arg Asp Pro Gly Ser
 80                  85                  90                  95 acg aac tgc cca cgt cct ctc cag gaa ggg acc ccg ggt tca cga gct       335
Thr Asn Cys Pro Arg Pro Leu Gln Glu Gly Thr Pro Gly Ser Arg Ala
                100                 105                 110 gcc cac gtc ctc tcc agg agg gga cac cgg gtt cac gag ctg ccc acg       383
Ala His Val Leu Ser Arg Arg Gly His Arg Val His Glu Leu Pro Thr
            115                 120                 125 ccc tct cca gga agg gac ccc ggg ttc atg agc tgc cca cgt cct ctc       431
Pro Ser Pro Gly Arg Asp Pro Gly Phe Met Ser Cys Pro Arg Pro Leu
        130                 135                 140 cag gaa ggg acc cgg gtc cac gaa ctg ccc acg ccc tct cca gga ggg       479
Gln Glu Gly Thr Arg Val His Glu Leu Pro Thr Pro Ser Pro Gly Gly
145                 150                 155 gac ccg ggt cca cga gct gcc cac gtc gtc aac ggg aag gga ccc ggg       527
Asp Pro Gly Pro Arg Ala Ala His Val Val Asn Gly Lys Gly Pro Gly
160                 165                 170                 175 tcc acg agc tgc cca cgt cct ctc cag gaa ggg acc cgg gtc cac gaa       575
Ser Thr Ser Cys Pro Arg Pro Leu Gln Glu Gly Thr Arg Val His Glu
                180                 185                 190 ctg ccc acg cgc tct cca gga ggg gac acc ggg ttc acg agc tgc cca       623
Leu Pro Thr Arg Ser Pro Gly Gly Asp Thr Gly Phe Thr Ser Cys Pro
            195                 200                 205 cgc cct ctc cag gaa ggg acc ccg ggt tca cga gct gcc cac gtc ctc       671
Arg Pro Leu Gln Glu Gly Thr Pro Gly Ser Arg Ala Ala His Val Leu
        210                 215                 220
```

```
tcc agg agg gga cac cgg gtt cac gag ctg ccc acg tcc tct cca gga    719
Ser Arg Arg Gly His Arg Val His Glu Leu Pro Thr Ser Ser Pro Gly
    225                 230                 235 ggg gac acc ggg ttc acg agc tgc cca cgc cct ctc cag gag ggg aca    767
Gly Asp Thr Gly Phe Thr Ser Cys Pro Arg Pro Leu Gln Glu Gly Thr
240                 245                 250                 255 ccg ggt tca cga gct gcc cac gtc ctc tcc agg aag gga ccc ggg tcc    815
Pro Gly Ser Arg Ala Ala His Val Leu Ser Arg Lys Gly Pro Gly Ser
                260                 265                 270 acg agc tgc cca cgt cct ctc cag gag ggg aca ccg ggt tca cga gct    863
Thr Ser Cys Pro Arg Pro Leu Gln Glu Gly Thr Pro Gly Ser Arg Ala
            275                 280                 285 gcc cac gca ctt tcc agg aag gga ccc cgg gtt cag gtc tcc tgc cgg    911
Ala His Ala Leu Ser Arg Lys Gly Pro Arg Val Gln Val Ser Cys Arg
        290                 295                 300 ccc aca tcg tgc ctt tgt gta aat cag aag aaa gat gag gaa cag gcc    959
Pro Thr Ser Cys Leu Cys Val Asn Gln Lys Lys Asp Glu Glu Gln Ala
    305                 310                 315 ctc ctc tct ctc cag gca ggc ttt ggt gga ggg gct gga tct cct gcc   1007
Leu Leu Ser Leu Gln Ala Gly Phe Gly Gly Gly Ala Gly Ser Pro Ala
320                 325                 330                 335 gca cct tcc ctg gca ggg cac cct gtg ctt gag ccc cag aac tgc agg   1055
Ala Pro Ser Leu Ala Gly His Pro Val Leu Glu Pro Gln Asn Cys Arg
                340                 345                 350 cgg ccg gca gag aag ggg tcc atg atg gcg cct cgg tgc gca gcc ttg   1103
Arg Pro Ala Glu Lys Gly Ser Met Met Ala Pro Arg Cys Ala Ala Leu
            355                 360                 365 gac ctg ccc cca tgg acc tgg aga cag ggt ttc tcc tca ttg gcc agg   1151
Asp Leu Pro Pro Trp Thr Trp Arg Gln Gly Phe Ser Ser Leu Ala Arg
        370                 375                 380 ctg gtc tcg aac tcc tgacctcaga cgatccacct gcctcagcct cccgaagtgt   1206
Leu Val Ser Asn Ser
        385 tgggattaca ggcacgagcc actgtgcccg gccatcattc cttttttactg ctgactaata   1266 gtctgctgtg tgaatccacc gctagaaacc cactcatcag ttgatggtca tgtgggttgc   1326 ttctgctatt cgcttattat gaacagtgct ggaataaacg ttcctgtgca ctcttgggca   1386 tacgcctagg agtggaactg ctgggtcaaa aaaaaaaaaa aaaaaaaaaa aaaaa         1441

<210> SEQ ID NO 5
<211> LENGTH: 388
<212> TYPE: PRT
<213> ORGANISM: Homo sapiens

<400> SEQUENCE: 5

Thr Ser Cys Pro Arg Pro Leu Gln Glu Gly Thr Pro Gly Ser Arg Ala
1               5                   10                  15

Ala His Val Val Ser Arg Lys Gly Pro Gly Ser Thr Ser Cys Pro Arg
            20                  25                  30

Pro Leu Gln Glu Arg Thr Arg Val His Glu Leu Ala Thr Ser Ser Ala
        35                  40                  45

Gly Arg Asp Pro Gly Ser Thr Ser Cys Pro Arg Pro Leu Gln Glu Gly
    50                  55                  60

Thr Pro Gly Ser Arg Ala Ala His Val Leu Ser Arg Lys Gly Pro Arg
65                  70                  75                  80

Val His Glu Leu Pro Thr Ser Ser Pro Gly Arg Asp Pro Gly Ser Thr
                85                  90                  95

Asn Cys Pro Arg Pro Leu Gln Glu Gly Thr Pro Gly Ser Arg Ala Ala
            100                 105                 110
```

```
His Val Leu Ser Arg Arg Gly His Arg Val His Glu Leu Pro Thr Pro
            115                 120                 125

Ser Pro Gly Arg Asp Pro Gly Phe Met Ser Cys Pro Arg Pro Leu Gln
130                 135                 140

Glu Gly Thr Arg Val His Glu Leu Pro Thr Pro Ser Pro Gly Gly Asp
145                 150                 155                 160

Pro Gly Pro Arg Ala Ala His Val Val Asn Gly Lys Gly Pro Gly Ser
                165                 170                 175

Thr Ser Cys Pro Arg Pro Leu Gln Glu Gly Thr Arg Val His Glu Leu
            180                 185                 190

Pro Thr Arg Ser Pro Gly Gly Asp Thr Gly Phe Thr Ser Cys Pro Arg
        195                 200                 205

Pro Leu Gln Glu Gly Thr Pro Gly Ser Arg Ala Ala His Val Leu Ser
        210                 215                 220

Arg Arg Gly His Arg Val His Glu Leu Pro Thr Ser Ser Pro Gly Gly
225                 230                 235                 240

Asp Thr Gly Phe Thr Ser Cys Pro Arg Pro Leu Gln Glu Gly Thr Pro
                245                 250                 255

Gly Ser Arg Ala Ala His Val Leu Ser Arg Lys Gly Pro Gly Ser Thr
            260                 265                 270

Ser Cys Pro Arg Pro Leu Gln Glu Gly Thr Pro Gly Ser Arg Ala Ala
        275                 280                 285

His Ala Leu Ser Arg Lys Gly Pro Arg Val Gln Val Ser Cys Arg Pro
        290                 295                 300

Thr Ser Cys Leu Cys Val Asn Gln Lys Lys Asp Glu Glu Gln Ala Leu
305                 310                 315                 320

Leu Ser Leu Gln Ala Gly Phe Gly Gly Ala Gly Ser Pro Ala Ala
                325                 330                 335

Pro Ser Leu Ala Gly His Pro Val Leu Glu Pro Gln Asn Cys Arg Arg
            340                 345                 350

Pro Ala Glu Lys Gly Ser Met Met Ala Pro Arg Cys Ala Ala Leu Asp
        355                 360                 365

Leu Pro Pro Trp Thr Trp Arg Gln Gly Phe Ser Ser Leu Ala Arg Leu
        370                 375                 380

Val Ser Asn Ser
385

<210> SEQ ID NO 6
<211> LENGTH: 1576
<212> TYPE: DNA
<213> ORGANISM: Homo sapiens
<220> FEATURE:
<221> NAME/KEY: CDS
<222> LOCATION: (3)..(1190)

<400> SEQUENCE: 6 tc acg agc tgc cca cgt cct ctc cag gaa ggg acc ccg ggt tca cga        47
   Thr Ser Cys Pro Arg Pro Leu Gln Glu Gly Thr Pro Gly Ser Arg
   1               5                   10                  15 gct gcc cac gtc gtc tcc agg aag gga ccc ggg tcc acg agc tgc cca        95
Ala Ala His Val Val Ser Arg Lys Gly Pro Gly Ser Thr Ser Cys Pro
            20                  25                  30 cgt cct ctc cag gaa agg acc cgg gtc cac gag ctg gcc acg tcc tct       143
Arg Pro Leu Gln Glu Arg Thr Arg Val His Glu Leu Ala Thr Ser Ser
            35                  40                  45 gca gga agg gac ccc ggg tcc acg agc tgc cca cgt cct ctc cag gaa       191
Ala Gly Arg Asp Pro Gly Ser Thr Ser Cys Pro Arg Pro Leu Gln Glu
```

-continued

```
               50                   55                   60
ggg acc ccg ggt tca cga gct gcc cac gtc ctc tcc agg aag gga ccc         239
Gly Thr Pro Gly Ser Arg Ala Ala His Val Leu Ser Arg Lys Gly Pro
         65                   70                   75 cgg gtc cac gag ctg ccc acg tcc tct cca gga agg gac ccc ggg tcc         287
Arg Val His Glu Leu Pro Thr Ser Ser Pro Gly Arg Asp Pro Gly Ser
 80                   85                   90                   95 acg aac tgc cca cgt cct ctc cag gaa ggg acc ccg ggt tca cga gct         335
Thr Asn Cys Pro Arg Pro Leu Gln Glu Gly Thr Pro Gly Ser Arg Ala
                100                  105                  110 gcc cac gtc ctc tcc agg agg gga cac cgg gtt cac gag ctg ccc acg         383
Ala His Val Leu Ser Arg Arg Gly His Arg Val His Glu Leu Pro Thr
             115                  120                  125 ccc tct cca gga agg gac ccc ggg ttc atg agc tgc cca cgt cct ctc         431
Pro Ser Pro Gly Arg Asp Pro Gly Phe Met Ser Cys Pro Arg Pro Leu
         130                  135                  140 cag gaa ggg acc cgg gtc cac gaa ctg ccc acg ccc tct cca gga ggg         479
Gln Glu Gly Thr Arg Val His Glu Leu Pro Thr Pro Ser Pro Gly Gly
     145                  150                  155 gac ccg ggt cca cga gct gcc cac gtc gtc aac ggg aag gga ccc ggg         527
Asp Pro Gly Pro Arg Ala Ala His Val Val Asn Gly Lys Gly Pro Gly
160                  165                  170                  175 tcc acg agc tgc cca cgt cct ctc cag gaa ggg acc cgg gtc cac gaa         575
Ser Thr Ser Cys Pro Arg Pro Leu Gln Glu Gly Thr Arg Val His Glu
                180                  185                  190 ctg ccc acg cgc tct cca gga ggg gac acc ggg ttc acg agc tgc cca         623
Leu Pro Thr Arg Ser Pro Gly Gly Asp Thr Gly Phe Thr Ser Cys Pro
             195                  200                  205 cgc cct ctc cag gaa ggg acc ccg ggt tca cga gct gcc cac gtc ctc         671
Arg Pro Leu Gln Glu Gly Thr Pro Gly Ser Arg Ala Ala His Val Leu
         210                  215                  220 tcc agg agg gga cac cgg gtt cac gag ctg ccc acg tcc tct cca gga         719
Ser Arg Arg Gly His Arg Val His Glu Leu Pro Thr Ser Ser Pro Gly
     225                  230                  235 ggg gac acc ggg ttc acg agc tgc cca cgc cct ctc cag gag ggg aca         767
Gly Asp Thr Gly Phe Thr Ser Cys Pro Arg Pro Leu Gln Glu Gly Thr
240                  245                  250                  255 ccg ggt tca cga gct gcc cac gtc ctc tcc agg aag gga ccc ggg tcc         815
Pro Gly Ser Arg Ala Ala His Val Leu Ser Arg Lys Gly Pro Gly Ser
                260                  265                  270 acg agc tgc cca cgt cct ctc cag gag ggg aca ccg gtc cga gct          863
Thr Ser Cys Pro Arg Pro Leu Gln Glu Gly Thr Pro Gly Ser Arg Ala
             275                  280                  285 gcc cac gca ctt tcc agg aag gga ccc cgg gtt cag gtc tcc tgc cgg         911
Ala His Ala Leu Ser Arg Lys Gly Pro Arg Val Gln Val Ser Cys Arg
         290                  295                  300 ccc aca tcg tgc ctt tgt gta aat cag aag aaa gat gag gaa cag gcc         959
Pro Thr Ser Cys Leu Cys Val Asn Gln Lys Lys Asp Glu Glu Gln Ala
     305                  310                  315 ctc ctc tct ctc cag gca ggc ttt ggt gga ggg gct gga tct cct gcc        1007
Leu Leu Ser Leu Gln Ala Gly Phe Gly Gly Gly Ala Gly Ser Pro Ala
320                  325                  330                  335 gca cct tcc ctg gca ggg cac cct gtg ctt gag ccc cag aac tgc agg        1055
Ala Pro Ser Leu Ala Gly His Pro Val Leu Glu Pro Gln Asn Cys Arg
                340                  345                  350 cgg ccg gca gag aag ggg tcc atg atg gcg cct cgg tgc gca gcc ttg        1103
Arg Pro Ala Glu Lys Gly Ser Met Met Ala Pro Arg Cys Ala Ala Leu
             355                  360                  365 gac ctg ccc cca tgg acc tgg gaa cct ccc ggc tct tcc cac tcg gga        1151
Asp Leu Pro Pro Trp Thr Trp Glu Pro Pro Gly Ser Ser His Ser Gly
```

-continued

```
                     370                 375                 380
aag gaa ggc tct ggg cat gga gct tta ttg agg tat agt tgacaattca       1200
Lys Glu Gly Ser Gly His Gly Ala Leu Leu Arg Tyr Ser
        385                 390                 395 ggacggtgtg cactcaaggt atgcagcatc acaacctgac acacgtaggc attgtgaaat   1260
gagtcccaca attgggctaa ttaacacacc catcaccta catggttact tctttctgtg    1320
gtgagaacac taaattttaa atagaggaca cacagcctgg gcaacatagt gagaccctgt   1380
ctctacaaat ataaaaaaat tatctggacg tggtggtgca cacctgtggt cccagctact   1440
tgggaagctg aggctggaga atcacttgag cctgggaggc ggaggttgcg gtgcactcca   1500
gcctgggcga cagagggagg ccctatctca aaataaataa ataaaggaca cattcttatc   1560
aaaaaaaaaa aaaaa                                                    1576

<210> SEQ ID NO 7
<211> LENGTH: 396
<212> TYPE: PRT
<213> ORGANISM: Homo sapiens

<400> SEQUENCE: 7

Thr Ser Cys Pro Arg Pro Leu Gln Glu Gly Thr Pro Gly Ser Arg Ala
  1               5                  10                  15

Ala His Val Val Ser Arg Lys Gly Pro Gly Ser Thr Ser Cys Pro Arg
             20                  25                  30

Pro Leu Gln Glu Arg Thr Arg Val His Glu Leu Ala Thr Ser Ser Ala
         35                  40                  45

Gly Arg Asp Pro Gly Ser Thr Ser Cys Pro Arg Pro Leu Gln Glu Gly
     50                  55                  60

Thr Pro Gly Ser Arg Ala Ala His Val Leu Ser Arg Lys Gly Pro Arg
 65                  70                  75                  80

Val His Glu Leu Pro Thr Ser Ser Pro Gly Arg Asp Pro Gly Ser Thr
                 85                  90                  95

Asn Cys Pro Arg Pro Leu Gln Glu Gly Thr Pro Gly Ser Arg Ala Ala
            100                 105                 110

His Val Leu Ser Arg Arg Gly His Arg Val His Glu Leu Pro Thr Pro
        115                 120                 125

Ser Pro Gly Arg Asp Pro Gly Phe Met Ser Cys Pro Arg Pro Leu Gln
    130                 135                 140

Glu Gly Thr Arg Val His Glu Leu Pro Thr Pro Ser Pro Gly Gly Asp
145                 150                 155                 160

Pro Gly Pro Arg Ala Ala His Val Val Asn Gly Lys Gly Pro Gly Ser
                165                 170                 175

Thr Ser Cys Pro Arg Pro Leu Gln Glu Gly Thr Arg Val His Glu Leu
            180                 185                 190

Pro Thr Arg Ser Pro Gly Gly Asp Thr Gly Phe Thr Ser Cys Pro Arg
        195                 200                 205

Pro Leu Gln Glu Gly Thr Pro Gly Ser Arg Ala Ala His Val Leu Ser
    210                 215                 220

Arg Arg Gly His Arg Val His Glu Leu Pro Thr Ser Ser Pro Gly Gly
225                 230                 235                 240

Asp Thr Gly Phe Thr Ser Cys Pro Arg Pro Leu Gln Glu Gly Thr Pro
                245                 250                 255

Gly Ser Arg Ala Ala His Val Leu Ser Arg Lys Gly Pro Gly Ser Thr
            260                 265                 270

Ser Cys Pro Arg Pro Leu Gln Glu Gly Thr Pro Gly Ser Arg Ala Ala
```

```
                275                 280                 285
His Ala Leu Ser Arg Lys Gly Pro Arg Val Gln Val Ser Cys Arg Pro
    290                 295                 300

Thr Ser Cys Leu Cys Val Asn Gln Lys Lys Asp Glu Glu Gln Ala Leu
305                 310                 315                 320

Leu Ser Leu Gln Ala Gly Phe Gly Gly Ala Gly Ser Pro Ala Ala
                325                 330                 335

Pro Ser Leu Ala Gly His Pro Val Leu Glu Pro Gln Asn Cys Arg Arg
                340                 345                 350

Pro Ala Glu Lys Gly Ser Met Met Ala Pro Arg Cys Ala Ala Leu Asp
            355                 360                 365

Leu Pro Pro Trp Thr Trp Glu Pro Pro Gly Ser Ser His Ser Gly Lys
        370                 375                 380

Glu Gly Ser Gly His Gly Ala Leu Leu Arg Tyr Ser
385                 390                 395

<210> SEQ ID NO 8
<211> LENGTH: 2010
<212> TYPE: DNA
<213> ORGANISM: Homo sapiens
<220> FEATURE:
<221> NAME/KEY: CDS
<222> LOCATION: (3)..(1244)

<400> SEQUENCE: 8 tc acg agc tgc cca cgt cct ctc cag gaa ggg acc ccg ggt tca cga       47
   Thr Ser Cys Pro Arg Pro Leu Gln Glu Gly Thr Pro Gly Ser Arg
   1               5                   10                  15 gct gcc cac gtc gtc tcc agg aag gga ccc ggg tcc acg agc tgc cca     95
Ala Ala His Val Val Ser Arg Lys Gly Pro Gly Ser Thr Ser Cys Pro
                20                  25                  30 cgt cct ctc cag gaa agg acc cgg gtc cac gag ctg gcc acg tcc tct    143
Arg Pro Leu Gln Glu Arg Thr Arg Val His Glu Leu Ala Thr Ser Ser
            35                  40                  45 gca gga agg gac ccc ggg tcc acg agc tgc cca cgt cct ctc cag gaa    191
Ala Gly Arg Asp Pro Gly Ser Thr Ser Cys Pro Arg Pro Leu Gln Glu
        50                  55                  60 ggg acc ccg ggt tca cga gct gcc cac gtc ctc tcc agg aag gga ccc    239
Gly Thr Pro Gly Ser Arg Ala Ala His Val Leu Ser Arg Lys Gly Pro
65                  70                  75 cgg gtc cac gag ctg ccc acg tcc tct cca gga agg gac ccc ggg tcc    287
Arg Val His Glu Leu Pro Thr Ser Ser Pro Gly Arg Asp Pro Gly Ser
80                  85                  90                  95 acg aac tgc cca cgt cct ctc cag gaa ggg acc ccg ggt tca cga gct    335
Thr Asn Cys Pro Arg Pro Leu Gln Glu Gly Thr Pro Gly Ser Arg Ala
                100                 105                 110 gcc cac gtc ctc tcc agg agg gga cac cgg gtt cac gag ctg ccc acg    383
Ala His Val Leu Ser Arg Arg Gly His Arg Val His Glu Leu Pro Thr
            115                 120                 125 ccc tct cca gga agg gac ccc ggg ttc atg agc tgc cca cgt cct ctc    431
Pro Ser Pro Gly Arg Asp Pro Gly Phe Met Ser Cys Pro Arg Pro Leu
        130                 135                 140 cag gaa ggg acc cgg gtc cac gaa ctg ccc acg ccc tct cca gga ggg    479
Gln Glu Gly Thr Arg Val His Glu Leu Pro Thr Pro Ser Pro Gly Gly
145                 150                 155 gac ccg ggt cca cga gct gcc cac gtc gtc aac ggg aag gga ccc ggg    527
Asp Pro Gly Pro Arg Ala Ala His Val Val Asn Gly Lys Gly Pro Gly
160                 165                 170                 175 tcc acg agc tgc cca cgt cct ctc cag gaa ggg acc cgg gtc cac gaa    575
Ser Thr Ser Cys Pro Arg Pro Leu Gln Glu Gly Thr Arg Val His Glu
```

```
                        180                 185                 190
ctg ccc acg cgc tct cca gga ggg gac acc ggg ttc acg agc tgc cca        623
Leu Pro Thr Arg Ser Pro Gly Gly Asp Thr Gly Phe Thr Ser Cys Pro
                195                 200                 205 cgc cct ctc cag gaa ggg acc ccg ggt tca cga gct gcc cac gtc ctc        671
Arg Pro Leu Gln Glu Gly Thr Pro Gly Ser Arg Ala Ala His Val Leu
        210                 215                 220 tcc agg agg gga cac cgg gtt cac gag ctg ccc acg tcc tct cca gga        719
Ser Arg Arg Gly His Arg Val His Glu Leu Pro Thr Ser Ser Pro Gly
        225                 230                 235 ggg gac acc ggg ttc acg agc tgc cca cgc cct ctc cag gag ggg aca        767
Gly Asp Thr Gly Phe Thr Ser Cys Pro Arg Pro Leu Gln Glu Gly Thr
240                 245                 250                 255 ccg ggt tca cga gct gcc cac gtc ctc tcc agg aag gga ccc ggg tcc        815
Pro Gly Ser Arg Ala Ala His Val Leu Ser Arg Lys Gly Pro Gly Ser
                260                 265                 270 acg agc tgc cca cgt cct ctc cag gag ggg aca ccg ggt tca cga gct        863
Thr Ser Cys Pro Arg Pro Leu Gln Glu Gly Thr Pro Gly Ser Arg Ala
                275                 280                 285 gcc cac gca ctt tcc agg aag gga ccc cgg gtt cag gtc tcc tgc cgg        911
Ala His Ala Leu Ser Arg Lys Gly Pro Arg Val Gln Val Ser Cys Arg
        290                 295                 300 ccc aca tcg tgc ctt tgt gta aat cag aag aaa gat gag gaa cag gcc        959
Pro Thr Ser Cys Leu Cys Val Asn Gln Lys Lys Asp Glu Glu Gln Ala
        305                 310                 315 ctc ctc tct ctc cag gca ggc ttt ggt gga ggg gct gga tct cct gcc       1007
Leu Leu Ser Leu Gln Ala Gly Phe Gly Gly Gly Ala Gly Ser Pro Ala
320                 325                 330                 335 gca cct tcc ctg gca ggg cac cct gtg ctt gag ccc cag aac tgc agg       1055
Ala Pro Ser Leu Ala Gly His Pro Val Leu Glu Pro Gln Asn Cys Arg
                340                 345                 350 cgg ccg gca gag aag ggg tcc atg atg gcg cct cgg tgc gca gcc ttg       1103
Arg Pro Ala Glu Lys Gly Ser Met Met Ala Pro Arg Cys Ala Ala Leu
                355                 360                 365 gac ctg ccc cca tgg acc tgg atg cca gtg atg cct gag gtc tgc agg       1151
Asp Leu Pro Pro Trp Thr Trp Met Pro Val Met Pro Glu Val Cys Arg
        370                 375                 380 gca gtg cat acg ctc acc gcc tgg ccg ctc agg agc ctg tgc ttg acc       1199
Ala Val His Thr Leu Thr Ala Trp Pro Leu Arg Ser Leu Cys Leu Thr
385                 390                 395 ccc aaa tcc gcc ccc caa ctc cct gtt acc ggc tca ctc ctt cca           1244
Pro Lys Ser Ala Pro Gln Leu Pro Val Thr Gly Ser Leu Leu Pro
400                 405                 410 tgagggcct tccccaggga cagccgatgc tctcctgatg gctcctgccc ttgcagagtg      1304
ctgcccccgc ctgcccacct ggcctggacc ctcgcctgag ccccctcagg gctctgcgcc     1364
acctcaaccc aggcgtttgt tccgcaggaa cctcccggct cttcccactc gggaaaggaa     1424
ggctctgggc atggaggtcg gccaggcccc atccccgtac cctggccctt cttcctgctt     1484
cctgtttgtc actgccccgg ggcctttgca cctgcattcc ctctctctgt gagtgtcctg     1544
gggcccgtta cccacgtcac cgtcccagga tacctttttct tttctttctc tctctccagc   1604
tttattgagg tatagttgac aattcaggac ggtgtgcact caaggtatgc agcatcacaa     1664
cctgacacac gtaggcattg tgaaatgagt cccacaattg gctaattaa cacacccatc     1724 accttacatg gttacttctt tctgtggtga aacactaaa ttttaaatag aggacacaca    1784
gcctgggcaa catagtgaga ccctgtctct acaaatataa aaaaattatc tggacgtggt     1844
ggtgcacacc tgtggtccca gctacttggg aagctgaggc tggagaatca cttgagcctg    1904
```

```
ggaggcggag gttgcggtgc actccagcct gggcgacaga gggaggccct atctcaaaat    1964
aaataaataa aggacacatt cttatcaaaa aaaaaaaaaa aaaaaa                   2010
```

<210> SEQ ID NO 9
<211> LENGTH: 414
<212> TYPE: PRT
<213> ORGANISM: Homo sapiens

<400> SEQUENCE: 9

```
Thr Ser Cys Pro Arg Pro Leu Gln Glu Gly Thr Pro Gly Ser Arg Ala
 1               5                  10                  15

Ala His Val Val Ser Arg Lys Gly Pro Gly Ser Thr Cys Pro Arg
            20                  25                  30

Pro Leu Gln Glu Arg Thr Arg Val His Glu Leu Ala Thr Ser Ser Ala
        35                  40                  45

Gly Arg Asp Pro Gly Ser Thr Ser Cys Pro Arg Pro Leu Gln Glu Gly
    50                  55                  60

Thr Pro Gly Ser Arg Ala Ala His Val Leu Ser Arg Lys Gly Pro Arg
65                  70                  75                  80

Val His Glu Leu Pro Thr Ser Ser Pro Gly Arg Asp Pro Gly Ser Thr
                85                  90                  95

Asn Cys Pro Arg Pro Leu Gln Glu Gly Thr Pro Gly Ser Arg Ala Ala
            100                 105                 110

His Val Leu Ser Arg Arg Gly His Arg Val His Glu Leu Pro Thr Pro
        115                 120                 125

Ser Pro Gly Arg Asp Pro Gly Phe Met Ser Cys Pro Arg Pro Leu Gln
    130                 135                 140

Glu Gly Thr Arg Val His Glu Leu Pro Thr Pro Ser Pro Gly Gly Asp
145                 150                 155                 160

Pro Gly Pro Arg Ala Ala His Val Val Asn Gly Lys Gly Pro Gly Ser
                165                 170                 175

Thr Ser Cys Pro Arg Pro Leu Gln Glu Gly Thr Arg Val His Glu Leu
            180                 185                 190

Pro Thr Arg Ser Pro Gly Gly Asp Thr Gly Phe Thr Ser Cys Pro Arg
        195                 200                 205

Pro Leu Gln Glu Gly Thr Pro Gly Ser Arg Ala Ala His Val Leu Ser
    210                 215                 220

Arg Arg Gly His Arg Val His Glu Leu Pro Thr Ser Ser Pro Gly Gly
225                 230                 235                 240

Asp Thr Gly Phe Thr Ser Cys Pro Arg Pro Leu Gln Glu Gly Thr Pro
                245                 250                 255

Gly Ser Arg Ala Ala His Val Leu Ser Arg Lys Gly Pro Gly Ser Thr
            260                 265                 270

Ser Cys Pro Arg Pro Leu Gln Glu Gly Thr Pro Gly Ser Arg Ala Ala
        275                 280                 285

His Ala Leu Ser Arg Lys Gly Pro Arg Val Gln Val Ser Cys Arg Pro
    290                 295                 300

Thr Ser Cys Leu Cys Val Asn Gln Lys Lys Asp Glu Glu Gln Ala Leu
305                 310                 315                 320

Leu Ser Leu Gln Ala Gly Phe Gly Gly Ala Gly Ser Pro Ala Ala
                325                 330                 335

Pro Ser Leu Ala Gly His Pro Val Leu Glu Pro Gln Asn Cys Arg Arg
            340                 345                 350

Pro Ala Glu Lys Gly Ser Met Met Ala Pro Arg Cys Ala Ala Leu Asp
        355                 360                 365
```

```
Leu Pro Pro Trp Thr Trp Met Pro Val Met Pro Glu Val Cys Arg Ala
    370                 375                 380
Val His Thr Leu Thr Ala Trp Pro Leu Arg Ser Leu Cys Leu Thr Pro
385                 390                 395                 400
Lys Ser Ala Pro Gln Leu Pro Val Thr Gly Ser Leu Leu Pro
                405                 410

<210> SEQ ID NO 10
<211> LENGTH: 1744
<212> TYPE: DNA
<213> ORGANISM: Homo sapiens
<220> FEATURE:
<221> NAME/KEY: CDS
<222> LOCATION: (3)..(1349)

<400> SEQUENCE: 10 tc acg agc tgc cca cgt cct ctc cag gaa ggg acc ccg ggt tca cga       47
   Thr Ser Cys Pro Arg Pro Leu Gln Glu Gly Thr Pro Gly Ser Arg
   1               5                   10                  15 gct gcc cac gtc gtc tcc agg aag gga ccc ggg tcc acg agc tgc cca       95
Ala Ala His Val Val Ser Arg Lys Gly Pro Gly Ser Thr Ser Cys Pro
                20                  25                  30 cgt cct ctc cag gaa agg acc cgg gtc cac gag ctg gcc acg tcc tct     143
Arg Pro Leu Gln Glu Arg Thr Arg Val His Glu Leu Ala Thr Ser Ser
            35                  40                  45 gca gga agg gac ccc ggg tcc acg agc tgc cca cgt cct ctc cag gaa     191
Ala Gly Arg Asp Pro Gly Ser Thr Ser Cys Pro Arg Pro Leu Gln Glu
        50                  55                  60 ggg acc ccg ggt tca cga gct gcc cac gtc ctc tcc agg aag gga ccc     239
Gly Thr Pro Gly Ser Arg Ala Ala His Val Leu Ser Arg Lys Gly Pro
    65                  70                  75 cgg gtc cac gag ctg ccc acg tcc tct cca gga agg gac ccc ggg tcc     287
Arg Val His Glu Leu Pro Thr Ser Ser Pro Gly Arg Asp Pro Gly Ser
80                  85                  90                  95 acg aac tgc cca cgt cct ctc cag gaa ggg acc ccg ggt tca cga gct     335
Thr Asn Cys Pro Arg Pro Leu Gln Glu Gly Thr Pro Gly Ser Arg Ala
                100                 105                 110 gcc cac gtc ctc tcc agg agg gga cac cgg gtt cac gag ctg ccc acg     383
Ala His Val Leu Ser Arg Arg Gly His Arg Val His Glu Leu Pro Thr
            115                 120                 125 ccc tct cca gga agg gac ccc ggg ttc atg agc tgc cca cgt cct ctc     431
Pro Ser Pro Gly Arg Asp Pro Gly Phe Met Ser Cys Pro Arg Pro Leu
        130                 135                 140 cag gaa ggg acc cgg gtc cac gaa ctg ccc acg ccc tct cca gga ggg     479
Gln Glu Gly Thr Arg Val His Glu Leu Pro Thr Pro Ser Pro Gly Gly
    145                 150                 155 gac ccg ggt cca cga gct gcc cac gtc gtc aac ggg aag gga ccc ggg     527
Asp Pro Gly Pro Arg Ala Ala His Val Val Asn Gly Lys Gly Pro Gly
160                 165                 170                 175 tcc acg agc tgc cca cgt cct ctc cag gaa ggg acc cgg gtc cac gaa     575
Ser Thr Ser Cys Pro Arg Pro Leu Gln Glu Gly Thr Arg Val His Glu
                180                 185                 190 ctg ccc acg cgc tct cca gga ggg gac acc ggg ttc acg agc tgc cca     623
Leu Pro Thr Arg Ser Pro Gly Gly Asp Thr Gly Phe Thr Ser Cys Pro
            195                 200                 205 cgc cct ctc cag gaa ggg acc ccg ggt tca cga gct gcc cac gtc ctc     671
Arg Pro Leu Gln Glu Gly Thr Pro Gly Ser Arg Ala Ala His Val Leu
        210                 215                 220 tcc agg agg gga cac cgg gtt cac gag ctg ccc acg tcc tct cca gga     719
Ser Arg Arg Gly His Arg Val His Glu Leu Pro Thr Ser Ser Pro Gly
    225                 230                 235
```

```
ggg gac acc ggg ttc acg agc tgc cca cgc cct ctc cag gag ggg aca      767
Gly Asp Thr Gly Phe Thr Ser Cys Pro Arg Pro Leu Gln Glu Gly Thr
240             245                 250                 255 ccg ggt tca cga gct gcc cac gtc ctc tcc agg aag gga ccc ggg tcc      815
Pro Gly Ser Arg Ala Ala His Val Leu Ser Arg Lys Gly Pro Gly Ser
            260                 265                 270 acg agc tgc cca cgt cct ctc cag gag ggg aca ccg ggt tca cga gct      863
Thr Ser Cys Pro Arg Pro Leu Gln Glu Gly Thr Pro Gly Ser Arg Ala
        275                 280                 285 gcc cac gca ctt tcc agg aag gga ccc cgg gtt cag gtc tcc tgc cgg      911
Ala His Ala Leu Ser Arg Lys Gly Pro Arg Val Gln Val Ser Cys Arg
    290                 295                 300 ccc aca tcg tgc ctt tgt gta aat cag aag aaa gat gag gaa cag gcc      959
Pro Thr Ser Cys Leu Cys Val Asn Gln Lys Lys Asp Glu Glu Gln Ala
305                 310                 315 ctc ctc tct ctc cag gca ggc ttt ggt gga ggg gct gga tct cct gcc     1007
Leu Leu Ser Leu Gln Ala Gly Phe Gly Gly Gly Ala Gly Ser Pro Ala
320                 325                 330                 335 gca cct tcc ctg gca ggg cac cct gtg ctt gag ccc cag aac tgc agg     1055
Ala Pro Ser Leu Ala Gly His Pro Val Leu Glu Pro Gln Asn Cys Arg
                340                 345                 350 cgg ccg gca gag aag ggg tcc atg atg gcg cct cgg tgc gca gcc ttg     1103
Arg Pro Ala Glu Lys Gly Ser Met Met Ala Pro Arg Cys Ala Ala Leu
            355                 360                 365 gac ctg ccc cca tgg acc tgg gaa cct ccc ggc tct cca cac tcg gga     1151
Asp Leu Pro Pro Trp Thr Trp Glu Pro Pro Gly Ser Ser His Ser Gly
        370                 375                 380 aag gaa ggc tct ggg cat gga ggt cgg cca ggc ccc atc ccc gta ccc     1199
Lys Glu Gly Ser Gly His Gly Gly Arg Pro Gly Pro Ile Pro Val Pro
    385                 390                 395 tgg ccc ttc ttc ctg ctt cct gtt tgt cac tgc ccc ggg gcc ttt gca     1247
Trp Pro Phe Phe Leu Leu Pro Val Cys His Cys Pro Gly Ala Phe Ala
400                 405                 410                 415 cct gca ttc cct ctc tct gtg agt gtc ctg ggg ccc gtt acc cac gtc     1295
Pro Ala Phe Pro Leu Ser Val Ser Val Leu Gly Pro Val Thr His Val
                420                 425                 430 acc gtc cca gga tac ctt ttc ttt tct ttc tct ctc tcc agc ttt att     1343
Thr Val Pro Gly Tyr Leu Phe Phe Ser Phe Ser Leu Ser Ser Phe Ile
            435                 440                 445 gag gta tagttgacaa ttcaggacgg tgtgcactca aggtatgcag catcacaacc      1399
Glu Val tgacacacgt aggcattgtg aaatgagtcc cacaattggg ctaattaaca cacccatcac  1459
cttacatggt tacttctttc tgtggtgaga acactaaatt ttaaatagag gacacacagc  1519
ctgggcaaca tagtgagacc ctgtctctac aaatataaaa aaattatctg gacgtggtgg  1579
tgcacacctg tggtcccagc tacttgggaa gctgaggctg agaatcact tgagcctggg   1639 aggcggaggt tgcggtgcac tccagcctgg gcgacagagg gaggccctat ctcaaaataa  1699
ataaataaag gacacattct tatcaaaaaa aaaaaaaaaa aaaaa                  1744

<210> SEQ ID NO 11
<211> LENGTH: 449
<212> TYPE: PRT
<213> ORGANISM: Homo sapiens

<400> SEQUENCE: 11

Thr Ser Cys Pro Arg Pro Leu Gln Glu Gly Thr Pro Gly Ser Arg Ala
 1               5                  10                  15

Ala His Val Val Ser Arg Lys Gly Pro Gly Ser Thr Ser Cys Pro Arg
```

```
                    20                  25                  30
Pro Leu Gln Glu Arg Thr Arg Val His Glu Leu Ala Thr Ser Ser Ala
                35                  40                  45

Gly Arg Asp Pro Gly Ser Thr Ser Cys Pro Arg Pro Leu Gln Glu Gly
            50                  55                  60

Thr Pro Gly Ser Arg Ala Ala His Val Leu Ser Arg Lys Gly Pro Arg
65                  70                  75                  80

Val His Glu Leu Pro Thr Ser Ser Pro Gly Arg Asp Pro Gly Ser Thr
                85                  90                  95

Asn Cys Pro Arg Pro Leu Gln Glu Gly Thr Pro Gly Ser Arg Ala Ala
            100                 105                 110

His Val Leu Ser Arg Arg Gly His Arg Val His Glu Leu Pro Thr Pro
        115                 120                 125

Ser Pro Gly Arg Asp Pro Gly Phe Met Ser Cys Pro Arg Pro Leu Gln
    130                 135                 140

Glu Gly Thr Arg Val His Glu Leu Pro Thr Pro Ser Pro Gly Gly Asp
145                 150                 155                 160

Pro Gly Pro Arg Ala Ala His Val Val Asn Gly Lys Gly Pro Gly Ser
                165                 170                 175

Thr Ser Cys Pro Arg Pro Leu Gln Glu Gly Thr Arg Val His Glu Leu
            180                 185                 190

Pro Thr Arg Ser Pro Gly Gly Asp Thr Gly Phe Thr Ser Cys Pro Arg
        195                 200                 205

Pro Leu Gln Glu Gly Thr Pro Gly Ser Arg Ala Ala His Val Leu Ser
    210                 215                 220

Arg Arg Gly His Arg Val His Glu Leu Pro Thr Ser Ser Pro Gly Gly
225                 230                 235                 240

Asp Thr Gly Phe Thr Ser Cys Pro Arg Pro Leu Gln Glu Gly Thr Pro
                245                 250                 255

Gly Ser Arg Ala Ala His Val Leu Ser Arg Lys Gly Pro Gly Ser Thr
            260                 265                 270

Ser Cys Pro Arg Pro Leu Gln Glu Gly Thr Pro Gly Ser Arg Ala Ala
        275                 280                 285

His Ala Leu Ser Arg Lys Gly Pro Arg Val Gln Val Ser Cys Arg Pro
    290                 295                 300

Thr Ser Cys Leu Cys Val Asn Gln Lys Lys Asp Glu Glu Gln Ala Leu
305                 310                 315                 320

Leu Ser Leu Gln Ala Gly Phe Gly Gly Ala Gly Ser Pro Ala Ala
                325                 330                 335

Pro Ser Leu Ala Gly His Pro Val Leu Glu Pro Gln Asn Cys Arg Arg
            340                 345                 350

Pro Ala Glu Lys Gly Ser Met Met Ala Pro Arg Cys Ala Ala Leu Asp
        355                 360                 365

Leu Pro Pro Trp Thr Trp Glu Pro Pro Gly Ser His Ser Gly Lys
    370                 375                 380

Glu Gly Ser Gly His Gly Gly Arg Pro Gly Pro Ile Pro Val Pro Trp
385                 390                 395                 400

Pro Phe Phe Leu Leu Pro Val Cys His Cys Pro Gly Ala Phe Ala Pro
                405                 410                 415

Ala Phe Pro Leu Ser Val Ser Val Leu Gly Pro Val Thr His Val Thr
            420                 425                 430

Val Pro Gly Tyr Leu Phe Phe Ser Phe Ser Leu Ser Ser Phe Ile Glu
        435                 440                 445
```

Val

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 12
gtagtaacag aatggacttt ga                                        22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 13
agagaggaac agcatcaaag tc                                        22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 14
caaacagggt ccaccgtgga aa                                        22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 15
gtgtttcagc cacatttcca cg                                        22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 16
atccaccgct agaaacccac tc                                        22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 17
gaccatcaac tgatgagtgg gt                                        22

<210> SEQ ID NO 18
<211> LENGTH: 22
<212> TYPE: DNA
<213> ORGANISM: Artificial Sequence
<220> FEATURE:

<223> OTHER INFORMATION: Description of Artificial Primer

<400> SEQUENCE: 18
tcatgggggt gctttgacct tg    22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 19
tggcctcaaa ggctcaaggt ca    22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Primer

<400> SEQUENCE: 20
tgtaggacta tattgctc    18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Primer

<400> SEQUENCE: 21
cgacatttag gtgacact    18

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Synthetic adapter
    oligonucleotide

<400> SEQUENCE: 22
gtcttcacca cgggg    15

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Synthetic adapter
    oligonucleotide

<400> SEQUENCE: 23
gtggtgaaga c    11

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Primer

<400> SEQUENCE: 24
gcccttaggg agagcagc    18

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 25
ccacatcgtg cctttgtgta                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 26
cactgtgtta aaacgcctgg                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 27
gttgggatta caggcacgag                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 28
cagaagcaac ccacatgacc                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 29
actacaggtt tgcaccacca                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 30
atgctctcct gatggctcct                                                   20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Primer
```

<400> SEQUENCE: 31
agggaatgca ggtgcaaag                                                     19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 32
actcgggaaa ggaaggctct                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 33
cataccttga gtgcacaccg                                                    20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 34
gacagtctgc tccacatcca                                                    20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Primer

<400> SEQUENCE: 35
tggagatgaa gtcttgctct tg                                                 22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 36
atatgtttgc tggctttggg                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Primer

<400> SEQUENCE: 37
cccaggctgt gtgtcctcta                                                    20

<210> SEQ ID NO 38
<211> LENGTH: 1124
<212> TYPE: DNA

<213> ORGANISM: Homo sapiens

<400> SEQUENCE: 38

```
tcacgagctg cccacgtcct ctccaggaag ggaccccggg ttcacgagct gcccacgtcg      60
tctccaggaa gggacccggg tccacgagct gcccacgtcc tctccaggaa aggacccggg     120
tccacgagct ggccacgtcc tctgcaggaa gggaccccgg gtccacgagc tgcccacgtc     180
ctctccagga agggaccccg ggttcacgag ctgcccacgt cctctccagg aagggacccc     240
gggtccacga gctgcccacg tcctctccag gaagggaccc cgggtccacg aactgcccac     300
gtcctctcca ggaagggacc ccgggttcac gagctgccca cgtcctctcc aggaggggac     360
accgggttca cgagctgccc acgccctctc caggaaggga cccgggttc atgagctgcc      420
cacgtcctct ccaggaaggg acccgggtcc acgaactgcc cacgccctct ccaggagggg     480
acccgggtcc acgagctgcc cacgtcgtca cgggaaggg acccgggtcc acgagctgcc      540
cacgtcctct ccaggaaggg acccgggtcc acgaactgcc cacgcgctct ccaggagggg     600
acaccgggtt cacgagctgc ccacgccctc tccaggaagg gaccccgggt tcacgagctg     660
cccacgtcct ctccaggagg ggacaccggg ttcacgagct gcccacgtcc tctccaggag     720
gggacaccgg gttcacgagc tgcccacgcc ctctccagga ggggacaccg gttcacgag     780
ctgcccacgt cctctccagg aagggacccg gtccacgag ctgcccacgt cctctccagg      840
aggggacacc gggttcacga gctgcccacg cactttccag gaagggaccc cggttcagg      900
tctcctgccg gcccacatcg tgcctttgtg taaatcagaa gaaagatgag gaacaggccc     960
tcctctctct ccaggcaggc tttggtggag gggctggatc tcctgccgca ccttccctgg    1020
cagggcaccc tgtgcttgag ccccagaact gcaggcggcc ggcagagaag gggtccatga    1080
tggcgcctcg gtgcgcagcc ttggacctgc ccccatggac ctgg                     1124
```

<210> SEQ ID NO 39
<211> LENGTH: 289
<212> TYPE: DNA
<213> ORGANISM: Homo sapiens

<400> SEQUENCE: 39

```
agacagggtt tctcctcatt ggccaggctg gtctcgaact cctgacctca gacgatccac      60
ctgcctcagc ctcccgaagt gttgggatta caggcacgag ccactgtgcc cggccatcat     120
tcctttttac tgctgactaa tagtctgctg tgtgaatcca ccgctagaaa cccactcatc     180
agttgatggt catgtgggtt gcttctgcta ttcgcttatt atgaacagtg ctggaataaa     240
cgttcctgtg cactcttggg catacgccta ggagtggaac tgctgggtc                 289
```

<210> SEQ ID NO 40
<211> LENGTH: 139
<212> TYPE: DNA
<213> ORGANISM: Homo sapiens

<400> SEQUENCE: 40

```
gaacctcccg gctcttccca ctcgggaaag gaaggctctg gcatggagg tcggccaggc       60
cccatccccg taccctggcc cttcttcctg cttcctgttt gtcactgccc cggggccttt     120
gcacctgcat tccctctct                                                  139
```

<210> SEQ ID NO 41
<211> LENGTH: 49
<212> TYPE: DNA
<213> ORGANISM: Homo sapiens

<400> SEQUENCE: 41
gaacctcccg gctcttccca ctcgggaaag gaaggctctg ggcatggag        49

<210> SEQ ID NO 42
<211> LENGTH: 866
<212> TYPE: DNA
<213> ORGANISM: Homo sapiens

<400> SEQUENCE: 42
atgccagtga tgcctgaggt ctgcagggca gtgcatacgc tcaccgcctg gccgctcagg    60
agcctgtgct tgaccccccaa atccgcccccc caactccctg ttaccggctc actccttcca   120 tgagggggcct tccccaggga cagccgatgc tctcctgatg gctcctgccc ttgcagagtg   180
ctgcccccgc ctgcccacct ggcctggacc ctcgcctgag cccccctcagg gctctgcgcc   240 acctcaaccc aggcgtttgt tccgcaggaa cctcccggct cttcccactc gggaaaggaa   300
ggctctgggc atggaggtcg gccaggcccc atccccgtac cctggccctt cttcctgctt   360
cctgtttgtc actgccccgg ggcctttgca cctgcattcc ctctctctgt gagtgtcctg   420
gggcccgtta cccacgtcac cgtcccagga tacctttttct tttcttttctc tctctccagc  480 tttattgagg tatagttgac aattcaggac ggtgtgcact caaggtatgc agcatcacaa   540
cctgacacac gtaggcattg tgaaatgagt cccacaattg gctaattaa cacacccatc    600 accttacatg gttacttctt tctgtggtga gaacactaaa ttttaaatag aggacacaca   660
gcctgggcaa catagtgaga ccctgtctct acaaatataa aaaaattatc tggacgtggt   720
ggtgcacacc tgtggtccca gctacttggg aagctgaggc tggagaatca cttgagcctg   780
ggaggcggag gttgcggtgc actccagcct gggcgacaga gggaggccct atctcaaaat   840 aaataaaataa aggacacatt cttatc                                       866

<210> SEQ ID NO 43
<211> LENGTH: 387
<212> TYPE: DNA
<213> ORGANISM: Homo sapiens

<400> SEQUENCE: 43
ctttattgag gtatagttga caattcagga cggtgtgcac tcaaggtatg cagcatcaca    60
acctgacaca cgtaggcatt gtgaaatgag tcccacaatt gggctaatta acacacccat   120
caccttacat ggttacttct ttctgtggtg agaacactaa attttaaata gaggacacac   180
agcctgggca acatagtgag accctgtctc tacaaatata aaaaaattat ctggacgtgg   240
tggtgcacac ctgtggtccc agctacttgg gaagctgagg ctggagaatc acttgagcct   300
gggaggcgga ggttgcggtg cactccagcc tgggcgacag agggaggccc tatctcaaaa   360
taaataaata aaggacacat tcttatc                                       387

<210> SEQ ID NO 44
<211> LENGTH: 599
<212> TYPE: DNA
<213> ORGANISM: Homo sapiens

<400> SEQUENCE: 44
gaacctcccg gctcttccca ctcgggaaag gaaggctctg ggcatggagg tcggccaggc    60
cccatccccg tacctggccc ttcttcctg cttcctgttt gtcactgccc cggggccttt   120
gcacctgcat tccctctctc tgtgagtgtc ctggggcccg ttacccacgt caccgtccca   180 ggatacctt tctttctttc tctctctcc agctttattg aggtatagtt gacaattcag    240

```
gacggtgtgc actcaaggta tgcagcatca caacctgaca cacgtaggca ttgtgaaatg        300
agtcccacaa ttgggctaat taacacaccc atcaccttac atggttactt ctttctgtgg        360
tgagaacact aaattttaaa tagaggacac acagcctggg caacatagtg agaccctgtc        420
tctacaaata taaaaaaatt atctggacgt ggtggtgcac acctgtggtc ccagctactt        480
gggaagctga ggctggagaa tcacttgagc ctgggaggcg gaggttgcgg tgcactccag        540
cctgggcgac agagggaggc cctatctcaa aataaataaa taaaggacac attcttatc        599

<210> SEQ ID NO 45
<211> LENGTH: 1028
<212> TYPE: DNA
<213> ORGANISM: Homo sapiens
<220> FEATURE:
<221> NAME/KEY: modified_base
<222> LOCATION: (267)
<223> OTHER INFORMATION: a, t, c or g

<400> SEQUENCE: 45
cgggcgtgta tatctcttca tagagagcgc tcagacagcg tgcgttaatc tgcgtcgata         60
tatagagatc tttatcactg agtagataga acgtacatga atgtacgaac agtccagacg        120
agtaacttga ctaggataag atagacagta ccaactaatg agacaagaag agggaatcat        180
atagaatcat gtagtctgag tctagcgagt gtcgacatga tcacaagcga aatacagact        240
atgagaagag gtagaaataa taagtanact gagaagagag gtcatatgta catacaaatc        300
agtaaagcaa tagaaattga atacattata agccacagtt acagaattag cctaatttaa        360
caaccatggc aagcgagtta tatcaaacat agaagagtaa actctatcga ccatgggtag        420
gaacgaataa aggcgtcgag aagacaataa gaatgcgtgt taaacagcaa tacaagagaa        480
tagcaccact gaagcagacc aaaggcgtca ccggggaagt agggaagagg cacctcacaa        540
ggagaggaaa gggcagtcct gatttttgaaa atttcagtga aaagacagtg ttgttcccgg        600
aggcagctta gtgatcccgc atcgactctg aagaggaccc tgagggtagg ggattttttgg       660 gcctgaccgg cctatgctga acgcccaccg ggaattcagg gagaaacacg ggcccccggc        720
ttccaggaga gcagccaggc cacagccctg aggacgggca aacccaccc aggcacggtg        780 agagggaggc cgcccaggcc tggggcctgg cggcagggga tgaagtggac cagagccccg        840
caaatcctaa cgtgggtgag cagtgagcct gtgtggctgc gagtggctcc gttttggggc        900
tgtttgttcc tgcagcaaat gatgccagcc ctgacggaac cagtgcacgt ccaccacgag        960
ctgcccacgt cctctccagg aagggacccg ggtccacgag ctgcccacgt cctctccagg       1020
aagggacc                                                                1028

<210> SEQ ID NO 46
<211> LENGTH: 40
<212> TYPE: DNA
<213> ORGANISM: Homo sapiens

<400> SEQUENCE: 46
actacaggtt tgcaccacca tgtcctgcta atttttttt                                40

<210> SEQ ID NO 47
<211> LENGTH: 40
<212> TYPE: DNA
<213> ORGANISM: Homo sapiens

<400> SEQUENCE: 47
actacaggtt tgcaccaccg tgtcctgcta atttttttt                                40
```

```
<210> SEQ ID NO 48
<211> LENGTH: 39
<212> TYPE: DNA
<213> ORGANISM: Homo sapiens

<400> SEQUENCE: 48
tgtgcactct tgggcatacg cctaggagtg gaactgctg                                39

<210> SEQ ID NO 49
<211> LENGTH: 39
<212> TYPE: DNA
<213> ORGANISM: Homo sapiens

<400> SEQUENCE: 49
tgtgcactct tgggcatatg cctaggagtg gaactgctg                                39

<210> SEQ ID NO 50
<211> LENGTH: 39
<212> TYPE: DNA
<213> ORGANISM: Homo sapiens

<400> SEQUENCE: 50
gggctctgcg ccacctcaac ccaggcgttt gttccgcag                                39

<210> SEQ ID NO 51
<211> LENGTH: 39
<212> TYPE: DNA
<213> ORGANISM: Homo sapiens

<400> SEQUENCE: 51
gggctctgcg ccacctcaac tcaggcgttt gttccgcag                                39
```